(12) United States Patent
Becker et al.

(10) Patent No.: US 10,829,801 B2
(45) Date of Patent: Nov. 10, 2020

(54) INACTIVATABLE TARGET CAPTURE OLIGOMERS FOR USE IN THE SELECTIVE HYBRIDIZATION AND CAPTURE OF TARGET NUCLEIC ACID SEQUENCES

(71) Applicant: GEN-PROBE INCORPORATED, San Diego, CA (US)

(72) Inventors: Michael M. Becker, San Diego, CA (US); Kristin W. Livezey, Encinitas, CA (US); Wai-Chung Lam, Bonsall, CA (US)

(73) Assignee: GEN-PROBE INCORPORATED, San Diego, CA (US)

(*) Notice: Subject to any disclaimer, the term of this patent is extended or adjusted under 35 U.S.C. 154(b) by 172 days.

(21) Appl. No.: 15/708,039

(22) Filed: Sep. 18, 2017

(65) Prior Publication Data
US 2018/0010172 A1 Jan. 11, 2018

Related U.S. Application Data

(62) Division of application No. 12/465,323, filed on May 13, 2009, now Pat. No. 10,316,352.

(60) Provisional application No. 61/052,944, filed on May 13, 2008.

(51) Int. Cl.
| | | |
|---|---|---|
| *C12Q 1/68* | (2018.01) | |
| *C07H 21/00* | (2006.01) | |
| *C12Q 1/6816* | (2018.01) | |
| *C12Q 1/6832* | (2018.01) | |
| *C12Q 1/6834* | (2018.01) | |
| *C12Q 1/686* | (2018.01) | |

(52) U.S. Cl.
CPC .......... *C12Q 1/6816* (2013.01); *C12Q 1/686* (2013.01); *C12Q 1/6832* (2013.01); *C12Q 1/6834* (2013.01)

(58) Field of Classification Search
CPC ................ C12Q 1/68; C07H 21/00
See application file for complete search history.

(56) References Cited

U.S. PATENT DOCUMENTS

| | | | |
|---|---|---|---|
| 4,174,384 A | 11/1979 | Ullman et al. | |
| 4,486,539 A | 12/1984 | Ranki et al. | |
| 4,556,643 A | 12/1985 | Paau et al. | |
| 4,581,333 A | 4/1986 | Kourilsky et al. | |
| 4,725,536 A | 2/1988 | Fritsch et al. | |
| 4,752,566 A | 6/1988 | Collins et al. | |
| 4,766,062 A | 8/1988 | Diamond et al. | |
| 4,818,680 A | 4/1989 | Collins et al. | |
| 4,824,776 A | 4/1989 | Heller et al. | |
| 4,868,105 A | 9/1989 | Urdea et al. | |
| 4,894,325 A | 1/1990 | Englehardt et al. | |
| 5,118,801 A | 6/1992 | Lizardi et al. | |
| 5,124,246 A | 6/1992 | Urdea et al. | |
| 5,200,314 A | 4/1993 | Urdea | |
| 5,268,266 A | 12/1993 | Fritsch et al. | |
| 5,283,174 A | 2/1994 | Arnold, Jr. et al. | |
| 5,288,609 A | 2/1994 | Engelhardt et al. | |
| 5,312,728 A | 5/1994 | Lizardi et al. | |
| 5,367,066 A * | 11/1994 | Urdea ...................... | C07F 9/10 |
| | | | 435/6.1 |
| 5,439,793 A | 8/1995 | Rose et al. | |
| 5,445,933 A | 8/1995 | Eadie et al. | |
| 5,457,025 A | 10/1995 | Collins et al. | |
| 5,503,979 A | 4/1996 | Kramer et al. | |
| 5,512,478 A | 4/1996 | Orser et al. | |
| 5,514,546 A | 5/1996 | Kool | |
| 5,599,667 A | 2/1997 | Arnold | |
| 5,607,834 A | 3/1997 | Bagwell et al. | |
| 5,631,148 A | 5/1997 | Urdea et al. | |
| 5,635,352 A | 6/1997 | Urdea et al. | |
| 5,667,976 A | 9/1997 | Van Ness et al. | |
| 5,681,697 A | 10/1997 | Urdea et al. | |

(Continued)

FOREIGN PATENT DOCUMENTS

| | | |
|---|---|---|
| EP | 0 601 889 A2 | 6/1994 |
| EP | 1 288 313 A2 | 3/2003 |

(Continued)

OTHER PUBLICATIONS

"Viruses", Wikipedia.com, accessed Nov. 24, 2012. (Year: 2012).*

(Continued)

*Primary Examiner* — Ethan C Whisenant
(74) *Attorney, Agent, or Firm* — Alston & Bird LLP; Jeff Landes

(57) ABSTRACT

The present invention provides compositions, kits and methods for the selective hybridization and capture of a specific target nucleic acid. The specific target nucleic acid may be present in a heterogeneous mixture of nucleic acids. Selective hybridization and capture provides a target nucleic acid that is substantially free of non-target and/or contaminating nucleic acids. Target nucleic acids that have been selectively hybridized and captured using the current invention are then used in subsequent analysis, wherein the presence of non-target and/or contaminating nucleic acids that interfere with said subsequent analysis have been substantially reduced or eliminated, thereby providing improved analysis results. The invention offers the further advantage of requiring less stringent purification and/or sterility efforts than conventionally needed in order to ensure that enzymes and other reagents used in subsequent analysis, or present in the environment in which an assay is performed, are free of bacterial or other contaminating nucleic acids.

14 Claims, 22 Drawing Sheets

Specification includes a Sequence Listing.

(56) References Cited

U.S. PATENT DOCUMENTS

| | | | |
|---|---|---|---|
| 5,702,893 A | 12/1997 | Urdea et al. | |
| 5,702,896 A | 12/1997 | Collins et al. | |
| 5,714,380 A | 2/1998 | Neri et al. | |
| 5,723,591 A | 3/1998 | Livak et al. | |
| 5,731,148 A | 3/1998 | Becker et al. | |
| 5,759,777 A | 6/1998 | Kearney et al. | |
| 5,780,224 A | 7/1998 | Collins | |
| 5,780,273 A | 7/1998 | Burg | |
| 5,827,649 A | 10/1998 | Rose et al. | |
| 5,849,481 A | 12/1998 | Urdea et al. | |
| 5,866,336 A * | 2/1999 | Nazarenko | C12Q 1/6818 435/6.12 |
| 5,914,230 A | 6/1999 | Liu et al. | |
| 5,925,517 A | 7/1999 | Tyagi et al. | |
| 6,025,133 A | 2/2000 | Stull et al. | |
| 6,030,787 A | 2/2000 | Livak et al. | |
| 6,037,130 A * | 3/2000 | Tyagi | C12Q 1/6818 435/6.1 |
| 6,060,246 A | 5/2000 | Summerton et al. | |
| 6,110,678 A | 8/2000 | Weisburg et al. | |
| 6,150,097 A | 11/2000 | Tyagi et al. | |
| 6,156,501 A | 12/2000 | McGall et al. | |
| 6,221,581 B1 | 4/2001 | Engelhardt et al. | |
| 6,261,785 B1 | 7/2001 | Wood et al. | |
| 6,268,128 B1 | 7/2001 | Collins et al. | |
| 6,280,952 B1 | 8/2001 | Weisburg et al. | |
| 6,355,421 B1 | 3/2002 | Coull et al. | |
| 6,361,945 B1 | 3/2002 | Becker et al. | |
| 6,432,674 B1 | 8/2002 | Hirata | |
| 6,444,661 B1 | 9/2002 | Barton et al. | |
| 6,451,588 B1 | 9/2002 | Egholm et al. | |
| RE37,891 E | 10/2002 | Collins et al. | |
| 6,472,522 B1 | 10/2002 | Horn et al. | |
| 6,489,464 B1 | 12/2002 | Agrawal et al. | |
| 6,528,267 B1 | 3/2003 | Coull et al. | |
| 6,534,273 B2 | 3/2003 | Weisburg et al. | |
| 6,534,274 B2 | 3/2003 | Becker et al. | |
| 6,566,055 B1 | 5/2003 | Monforte et al. | |
| 6,576,419 B1 | 6/2003 | Wei et al. | |
| 6,835,542 B2 | 12/2004 | Becker et al. | |
| 6,849,412 B2 | 2/2005 | Becker et al. | |
| 6,903,206 B1 | 6/2005 | Becker et al. | |
| 7,220,544 B2 | 5/2007 | Inose | |
| 7,851,150 B2 | 12/2010 | Dahlberg et al. | |
| 10,316,352 B2 | 6/2019 | Becker et al. | |
| 2002/0114784 A1 | 8/2002 | Li et al. | |
| 2003/0049673 A1 | 3/2003 | Atkinson et al. | |
| 2003/0113781 A1 | 6/2003 | Bortolin et al. | |
| 2004/0048311 A1 | 11/2004 | Ault-Riche et al. | |
| 2005/0186591 A1 | 8/2005 | Bumcrot et al. | |
| 2005/0196785 A1 * | 9/2005 | Quake | C12Q 1/6832 435/6.11 |
| 2005/0214789 A1 * | 9/2005 | Moyle | B01L 3/50851 435/6.12 |
| 2005/0025147 A1 | 11/2005 | Macevicz | |
| 2006/0068417 A1 * | 3/2006 | Becker | C12Q 1/6834 435/6.11 |
| 2006/0115850 A1 * | 6/2006 | Schatz | C12P 19/34 435/6.14 |
| 2006/0223133 A1 | 10/2006 | Fogo et al. | |
| 2006/0223197 A1 | 10/2006 | Vielsack | |
| 2006/0234234 A1 | 10/2006 | Van Dongen et al. | |
| 2006/0246453 A1 | 11/2006 | Kato et al. | |
| 2006/0252085 A1 | 11/2006 | Pollner et al. | |
| 2006/0292616 A1 | 12/2006 | Neely et al. | |
| 2007/0281317 A1 | 6/2007 | Becker | |
| 2007/0155008 A1 | 7/2007 | Zhang et al. | |
| 2007/0269799 A9 | 11/2007 | Zhang | |
| 2007/0298974 A1 | 12/2007 | Gudkov | |
| 2008/0108055 A1 * | 5/2008 | Linnen | C12Q 1/701 435/5 |
| 2008/0286775 A1 | 11/2008 | Becker et al. | |
| 2008/0311658 A1 * | 12/2008 | Shanklin | C12N 15/111 435/375 |
| 2010/0075302 A1 * | 3/2010 | Perlin | C12Q 1/6827 435/6.14 |
| 2012/0288857 A1 * | 11/2012 | Livak | C12Q 1/6823 435/6.11 |
| 2013/0035248 A1 | 2/2013 | Icenhour | |
| 2013/0040344 A1 | 2/2013 | Ju | |
| 2013/0040843 A1 | 2/2013 | Von Toerne et al. | |
| 2013/0040847 A1 | 2/2013 | Thrippleton et al. | |

FOREIGN PATENT DOCUMENTS

| | | |
|---|---|---|
| WO | WO 1992/015708 A2 | 9/1992 |
| WO | WO 1997/008183 A1 | 6/1997 |
| WO | WO 2000/001850 A2 | 1/2000 |
| WO | WO 2001/094625 A2 | 12/2001 |
| WO | WO 2002/006531 A2 | 1/2002 |
| WO | WO 2004/081520 A2 | 9/2004 |
| WO | WO 2005/047468 A2 | 5/2005 |
| WO | WO 2007/146154 A1 | 12/2007 |
| WO | WO 2009/140374 A2 | 11/2009 |
| WO | WO 2009/1403714 A2 | 11/2019 |

OTHER PUBLICATIONS

"How many species of bacteria are there", wisegeek.com; accessed Jan. 21, 2014. (Year: 2014).*
"Fungi," Wikipedia.com; accessed Jun. 3, 2013. (Year: 2013).*
"Plant," Wikipedia.com; accessed Aug. 28, 2015 (Year: 2015).*
"Mammal," Wikipedia.com; accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
"Archaea," Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*
"List of sequenced bacterial genomes", Wikipedia.com; accessed Jan. 24, 2014. (Year: 2014).*
Yang et al., Hybrid Molecular Probe for Nucleic Acid Analysis in Biological Samples. JACS 128 : 9986-9987 (Year: 2006).*
Didenko et al., Biotin-Labeled Hairpin Oligonucleotides. American J. of Pathology 152(4) : 897 (Year: 1998).*
Takeshita et al., Oligodeoxynucleotides containing Synthetic Abasic sites. J. of Biological Chemistry 262(21) : 10171 (Year: 1987).*
Yang et al., Hybrid Molecular Probe for Nucleic Acid Analysis in Biological Samples. JACS 128(31) : 9986 (Year: 2006).*
"Algae," Wikipedia.com, accessed Mar. 4, 2016.
"Archaea," Wikipedia.com, accessed May 11, 2016.
"Fish," Wikipedia.com, accessed Nov. 2, 2014.
"Fungi," Wikipedia.com, accessed Jun. 3, 2013.
"How many species of bacteria are there," Wisegeek.com, accessed Jan. 21, 2014.
"List of sequenced animal genomes," Wikipedia.com, accessed Jan. 19, 2018.
"List of sequenced bacterial genomes," Wikipedia.com, accessed Jan. 24, 2014.
"Mammal," Wikipedia.com, accessed Sep. 22, 2011.
"Murinae," Wikipedia.com, accessed Mar. 18, 2013.
"Oligonucleotide definition," Merriam-Webster.com, accessed Aug. 23, 2017.
"Plant," Wikipedia.com, accessed Aug. 28, 2015.
"Protozoa," Wikipedia.com, accessed May 11, 2016.
"Viruses," Wikipedia.com, accessed Nov. 24, 2012.
Communication Under Rule 71(3) EPC, EPO Application No. 09747458.9, dated Dec. 12, 2011.
Examiner's First Report, Australian Application No. 2009246363, dated Apr. 27, 2012.
Extended European Search Report, European Application No. 12163343.2-1222, dated Jun. 26, 2012.
Grady et al., "Deoxyribonucleic Acid Hybridization Analysis of the Defective Bacteriophage Carried by Strain 15 of *Escherichia coli*," J. Virol., 1971, 8(6): 850-855, American Society for Microbiology, Washington D.C., USA.
Grunstein et al., "Colony hybridization: A method for the isolation of cloned DNAs that contain a specific gene," Proc. Nat. Acad. Sci. USA, 1975, 72(10): 3961-3965, National Academy of Sciences, Washington D.C., USA.

(56) References Cited

OTHER PUBLICATIONS

Ikuta et al., "Dissociation kinetics of 19 base paired oligonucleotide-DNA duplexes containing different single mismatched base pairs," Nucleic Acids Res., 1987, 15(2): 797-811, IRL Press Limited, Oxford, England.

Livak et al., "Oligonucleotides With Fluorescent Dyes at Opposite Ends Provide a Quenched Probe System Useful for Detecting PCR Product and Nucleic Acid Hybridization," PCR Methods and Applications, Jun. 1995, pp. 357-362, vol. 4(6), Cold Spring Harbor La.

Lubini et al., "Stabilizing Effects of the RNA 2'-Substituent: Crystal Structure of an Oligodeozynucleotide Duplex Containing 2'-O-Methylated Adenosines," Chem. & Biol., 1994, pp. 39-45, vol. 14, Elsevier Trends Journal, Cambridge, GB.

Marras et al., "Multi-Plex Detection of Single-Nucleotide Variations Using Molecular Beacons," Genetic Analysis Biomolecular Engineering, 1999, pp. 151-156, vol. 14, Elsevier Trends Journal, Cambridge, GB.

Mergny et al., "Fluorescence Energy Transfer as a Probe for Nucleic Acid Structures and Sequences," Nucleic Acids Research, Mar. 1994, pp. 920-928, vol. 22(6), Oxford University Press, Oxford, GB.

Morrison et al., Sensitive Fluorescence-Based Thermodynamic and Kinetic Measurements of DNA Hybridization in Solution, Mar. 1993, pp. 3095-3104, vol. 32(2), American Chemical Society, USA.

Morrison et al., "Solution-Phase Detection of Polynucleotides Using Interacting Fluorescent Labels and Competitive Hybridization," Analytical Biochemistry, Dec. 1989, pp. 231-244, vol. 183(2), Academic Press, Inc., USA.

Notice of Reasons for Rejection, Japanese Patent Application No. 2011-509650, dated Nov. 29, 2013.

Ortiz et al., "PNA Molecular Beacons for Rapid Detection of PCR Amplicons," Molecular and Cellular Probes, Aug. 1998, pp. 219-226, vol. 12(4), Academic Press, Inc., GB.

Peng et al., "Reverse DNA Translocation Through a Solid-State Nanopore by Magnetic Tweezers," Nanotechnology, Feb. 2009, pp. 185101-185108, vol. 20, IOP Publishing Ltd., Bristol, UK.

Piatek et al., "Molecular Beacon Sequence Analysis for Detecting Drug Resistance in *Mycobacterium tuberculosis*" Nature Biotechnology, Apr. 1998, pp. 359-363, vol. 16(4), Nature Publishing Company, USA.

Refregiers et al., "Fluorescence Resonance Energy Transfer Analysis of the Degradation of an Oligonucleotide Protected by a Very Stable Hairpin," J. Biom. Struct. Dyn., 1996, pp. 365-371, vol. 14(3), Adenine Press, USA.

Sommer, et al., "Minimal homology requiements for PCR Primers," Nucleic Acids Research, vol. 17, No. 16, p. 6749, (1989).

Strachan et al., "Nucleic acid hybridization assays," in Human Molecular Genetics 2nd edt., NCBI Bookshelf, 1999, pp. 1-38, Wiley-Liss, New York, USA.

Tang et al., "Self-Stabilized Antisense Oligodeoxynucleotide Phosphorothioates: Properties and Anti-HIV Activity," Nucleic Acids Research, 1993, pp. 2729-2735, vol. 21(11), Oxford University Press, Oxford, GB.

Tyagi et al., "Molecular Beacons: Probes that fluoresce upon hybridization" Nature Biotechnology, Mar. 1996, pp. 303-308, vol. 14(3), Nature Publishing Company, USA.

U.S. Appl. No. 12/465,323 Final Office Action dated Jan. 29, 2015.
U.S. Appl. No. 12/465,323 Final Office Action dated Mar. 9, 2012.
U.S. Appl. No. 12/465,323 Final Office Action dated Sep. 12, 2017.
U.S. Appl. No. 12/465,323, Non-Final Office Action dated Jun. 3, 2014.
U.S. Appl. No. 12/465,323, Non-Final Office Action dated Sep. 12, 2018.
U.S. Appl. No. 12/465,323, Non-Final Office Action dated Sep. 23, 2011.
U.S. Appl. No. 12/465,323, Non-Final Office Action dated Oct. 16, 2015.
U.S. Appl. No. 12/465,323, Notice of Allowance dated Jan. 25, 2019.
U.S. Appl. No. 12/465,323, Requirement for Restriction/Election dated Jun. 3, 2011.

Varani et al., "Exceptionally Stable Nucleic Acid Hairpins," Annu. Rev. Biophys. Biomol. Struct., 1995, pp. 379-404, vol. 24, Annual Reviews, Inc., USA.

* cited by examiner

INACTIVATABLE TARGET CAPTURE OLIGOMERS FOR USE IN THE SELECTIVE HYBRIDIZATION AND CAPTURE OF TARGET NUCLEIC ACID SEQUENCES

CROSS REFERENCE TO RELATED APPLICATIONS

This application is a divisional application of U.S. application Ser. No. 12/465,323, which was filed on May 13, 2009, pending, and claims priority under 35 U.S.C. § 119(e) to U.S. provisional application Ser. No. 61/052,944, filed May 13, 2008; the contents of each are hereby incorporated by reference.

REFERENCE TO SEQUENCE LISTING

This application includes an electronic sequence listing in a file named "498228_SEQLST.txt," created Sep. 18, 2017 and containing 11, 961 bytes, which is hereby incorporated by reference in its entirety for all purposes.

FIELD OF THE INVENTION

This invention relates to methods, compositions, reaction mixtures and kits for the selective hybridization of multiple copies of a specific target nucleic acid sequence, which may be present either alone or as a component of a homogeneous or heterogeneous mixture of nucleic acids. Selectively hybridized target sequences are isolated for subsequent processing, such as analysis and/or storage of said target sequence. Analysis preferably includes amplification and detection of the target nucleic acid.

DESCRIPTION OF THE RELATED ART

The isolation and purification of nucleic acid molecules is an important step for a variety of downstream procedures such as nucleic analysis, nucleic acid reagent preparation, bulk drug substance preparation and the like. Desired for the isolation step is a bias of the selection medium towards the desired nucleic acid and away from contaminating nucleic acids. The objective is to maximize recovery of the desired nucleic acid and minimize the presence of contaminating nucleic acids. Nucleic acid isolation is currently performed using a variety of techniques, including attachment to solid supports.

Attachment of nucleic acid molecules to solid supports is generally known in that art. In U.S. Pat. No. 5,599,667, Arnold et al. describe the use of polycationic solid supports for selective capture and immobilization of large nucleic acids from mixtures of large and small nucleic acids. The immobilized nucleic acids are then detected. Similarly, U.S. Pub. No. 2008-0319182 describes a method for binding nucleic acids to a solid support in the presence of imidizoles and guanidiniums. See also, U.S. Pub. No. 2006-0252085.

In U.S. Pat. No. 6,110,678, Weisberg et al. describe a two-step hybridization and capture of polynucleotides in a sample using immobilized probes attached to solid supports. In a first step, a target capture probe is hybridized with a target nucleic acid. In a second step, the target nucleic acid and target capture probe complex are hybridized to the immobilized probe of the solid support. Weisburg's two-step hybridization is a target specific method in that a select target is captured by the target capture probe but the unwanted other nucleic acids in the sample are not. Weisburg's target capture probe comprises a first nucleic acid region that is configured to be substantially complementary to a desired target nucleic acid and to specifically hybridize to that target nucleic acid and not to other contaminating nucleic acids suspected of being in a sample.

Capture probes and solid supports are used to isolate nucleic acids from samples for a variety of subsequent downstream analysis procedures. (See, for example, U.S. Pub. No. 2008-0199863 by Luo et al.; U.S. Pub. No. 2007-0003937 by Wang, U.S. Pub. No. 2005-0059024 by Conrad, U.S. Pub. No. 2006-0263769 by Haake et al, and U.S. Pat. No. 2008-0300142 by Getts et al.) Once isolated, a target nucleic acid is then useful for a variety of downstream analyses, such as, characterization of a target nucleic acid molecule isolated from a cellular lysate or amplification and detection of a target nucleic acid isolated from a diagnostic sample.

Detection and/or quantitation of specific nucleic acid sequences is an important technique for identifying and classifying microorganisms, diagnosing infectious diseases, measuring response to various types of treatment, and the like. Such procedures are also useful in detecting and quantitating microorganisms in foodstuffs, water, beverages, industrial and environmental samples, seed stocks, and other types of material where the presence of specific microorganisms may need to be monitored. Numerous amplification-based methods for the detection and quantitation of target nucleic acids are well known and established in the art. PCR uses multiple cycles of denaturation, annealing of primer pairs to opposite strands, and primer extension to exponentially increase copy numbers of the target sequence (e.g., Mullis et al., U.S. Pat. Nos. 4,683,195 and 4,800,159; Mullis, U.S. Pat. No. 4,683,202; Gelfand et al., U.S. Pat. No. 5,804,375; Mullis et al. (1987) Meth. Enzymol. 155, 335-350; and Murakawa et al. (1988) DNA 7, 287-295). In RT-PCR, reverse transcriptase makes a complementary DNA (cDNA) from RNA, and the cDNA is then amplified by PCR to produce multiple copies of DNA (Gelfand et al., U.S. Pat. Nos. 5,322,770 and 5,310,652). Other well-known amplification methods include strand displacement amplification, (SDA), (e.g., Walker, et al. (1992), Proc. Natl. Acad. Sci. USA 89, 392-396; Walker et al., U.S. Pat. No. 5,270, 184; Walker, U.S. Pat. No. 5,455,166; and Walker et al. (1992) Nucleic Acids Research 20, 1691-1696); thermophilic SDA (tSDA), using thermophilic endonucleases and polymerases at higher temperatures in essentially the same method as SDA (European Pat. No. 0 684 315); rolling circle amplification (RCA) (e.g., Lizardi, U.S. Pat. No. 5,854,033); helicase dependent amplification (HDA) (e.g., Kong et al., U.S. Pub. No. US 2004-0058378 A1); loop-mediated isothermal amplification (LAMP) (e.g., Notomi et al., U.S. Pat. No. 6,410,278); and transcription-based amplification methods (e.g., Kwoh, D. et al. (1989) Proc. Natl. Acad. Sci. USA 86, 1173-1177), for example, NASBA (e.g., Malek et al., U.S. Pat. No. 5,130,238), Q.beta. replicase (e.g., Lizardi, P. et al. (1988) BioTechnol. 6, 1197-1202), self-sustained sequence replication (e.g., Guatelli, J. et al. (1990) Proc. Natl. Acad. Sci. USA 87, 1874-1878; Landgren (1993) Trends in Genetics 9, 199-202; and Helen H. Lee et al., Nucleic Acid Amplification Technologies (1997)), and transcription-mediated amplification, (TMA) (e.g., Kacian et al., U.S. Pat. Nos. 5,480,784 and 5,399,491). TMA synthesizes multiple copies of a target nucleic acid sequence autocatalytically under conditions of substantially constant temperature, ionic strength, and pH, in which multiple RNA copies of the target sequence autocatalytically generate additional copies. TMA is a robust and highly sensitive amplification system with demonstrated efficacy, and which overcomes many of the problems associated with PCR-based amplification systems. In particular, temperature cycling is not required.

Amplification assays are particularly well suited for the detection of microorganisms in the context of clinical laboratory testing, bioprocess monitoring, or any other setting in which the detection of microorganisms in a particular sample type is desired, by offering high sensitivity and rapid time-to-result relative to conventional microbiological techniques. In addition, amplification methods can be used in the detection of the vast number of microorganisms that are difficult or impossible to culture on synthetic media. Nevertheless, there are certain limitations associated with first-generation amplification assays that have limited their acceptance in certain settings, such as clinical microbiological laboratories. One inherent problem associated with the high sensitivity of nucleic acid amplification systems is that contaminating nucleic acid introduced into the amplification system (e.g., from one or more reagents used during amplification, from the technician performing the assay, from the environment in which the amplification is performed, etc.) can result in false positive results. For example, even extremely small amounts of nucleic acid contamination present in reagents and/or enzymes used in an amplification reaction, or in the environment in which the amplification reaction is performed, can give rise to a positive amplification signal despite the fact that the sequence of interest is not present in the nucleic acid sample being tested. This requires that significant effort be expended in sample preparation, purification, sterilization, etc., of the reagents used in amplification reactions to avoid or minimize false positive results.

Accordingly, there is a need in the art for compositions and methods for isolating a target nucleic acid compound while minimizing the presence of contaminating nucleic acids. There is also a need in the art for compositions and methods allowing for a robust nucleic acid amplification that selectively amplifies target nucleic acid sequences of interest while reducing or eliminating false positive results arising as a result of contaminating biological material, such as contaminating nucleic acid. There also remains a need for amplification systems that have reduced reagent purification and/or sterility requirements. As described further herein, the present invention meets these needs and offers other related advantages.

SUMMARY OF THE INVENTION

This invention relates to compositions, kits and methods for the selective hybridization of multiple copies of a specific target nucleic acid sequence, which may be present either alone or as a component of a homogeneous or heterogeneous mixture of nucleic acids. The inactivatable target capture oligomers of the current invention comprise at least three nucleic acid sequence regions: namely a target hybridization region; a tag-closing region; and a binding pair member region. Preferably, the binding pair member is a substantially homopolymeric nucleic acid sequence. Preferably, the tag-closing region is complementary to a portion of the target hybridization region such that the tag-closing region and target hybridization region will hybridize together under a set of conditions, thereby forming a hairpin structure as illustrated in the FIGS. and described herein. These inactivatable target capture oligomers selectively hybridized to target nucleic acid sequences, which are then isolated for subsequent processing, such as analysis and/or storage of said target sequence. Analysis preferably includes amplification and detection. These inactivatable target capture oligomers are capable of an active and an inactive configuration. In the active configuration and under a first set of conditions, the inactivatable target capture oligomers hybridize to a desired target nucleic acid. A second set of conditions is then met in the reaction mixture to inactivate the inactivatable target capture oligomer. By placing the inactivatable target capture oligomer into its inactive configuration its target hybridization region is blocked from further hybridization. Thus, the inactive configuration substantially reduces non-specific hybridization of the inactivatable target capture oligomer to a nucleic acid in the reaction mixture caused by, e.g., changes in the stringency conditions within the reaction mixture, time, size of the target hybridization region sequence, nucleic acid sequence similarity between the desired target nucleic acid and other non-targeted or contaminating nucleic acids in the mixture, and/or other events known to result in non-specific hybridization. Once a target nucleic acid is selectively hybridized to an inactivatable target capture oligomer of the current invention, the target can be captured using a solid support comprising a complementary binding pair member. Capture and wash techniques are well known in the art. (Weisburg et al., U.S. Pat. No. 6,534,273). Selectively hybridized and captured target nucleic acids can then be used in downstream analyses.

Thus, according to one embodiment of the present invention, there are provided compositions and methods for the selective hybridization of an inactivatable target capture oligomer to a target nucleic acid, wherein said target nucleic acids is a DNA sequence or an RNA sequence; the method comprises the steps of: (1) treating a target nucleic acid sequence in a nucleic acid sample with an inactivatable target capture oligomer in an active configuration, e.g., the tag-closing region and target hybridizing region are not stably hybridized one to the other, and under a first set of conditions for stably hybridizing the target hybridization region to a target nucleic acid sequence; and (2) inactivating any unhybridized inactivatable target capture oligomers by applying a second set of conditions for stably hybridizing the target hybridization region and tag-closing region of the unhybridized inactivatable target capture oligomer. The method can further comprise the step of capturing said selectively hybridized target nucleic acid. Preferably, the capture step comprises using a solid support comprising a second binding pair member complementary to the binding pair member of the inactivatable capture probe is introduced, thereby complexing with the inactivatable target capture oligomer. Preferably, the first and second binding pair members are complementary and substantially homopolymeric nucleotides sequences. Preferably, said solid support is a magnetic bead.

The present invention substantially reduces target capture of non-target and contaminating nucleic acids. The term "non-target nucleic acid" is generally used herein to refer to nucleic acids, other than the target nucleic acid, that are naturally present within the sample source, whereas the term "contaminating nucleic acids" is generally used herein to refer to nucleic acids, other than the target nucleic acid, that are introduced into a reaction mixture from a source external to the sample. Contaminating nucleic acids include, but are not limited to, nucleic acid that may be present in one or more reagents, components or materials that are used in an amplification reaction or that are present in the environment in which an amplification reaction is performed as well as nucleic acids from the sample source. The invention offers the advantage of requiring less stringent reagent purification and/or sterility efforts than those conventionally used to ensure that enzymes and other reagents and components used in amplification reactions are free of bacterial and other nucleic acid contaminants that may yield false positive results. Such reagents or components include, but are not limited to, water, buffers, salts, solid supports (e.g., magnetically charged particles or beads), and receptacles (e.g., glassware or plasticware).

A mixture of nucleic acids may be those found in a sample, such as a clinical sample taken for diagnostic testing and screening of blood products; sterility testing; seed stock testing; microbiological detection from a food source, water source, beverage source, industrial source or environmental source; research studies; whole cell lysates; reagent preparation and QC testing; or materials for other processes such as cloning, or for other purposes where the presence of a target nucleic acid may need to be detected and/or monitored. The selective amplification of specific nucleic acid sequences, as described herein, is of particular value in any of a variety of detection assays for increasing the accuracy and reliability of such assays while at the same time reducing the preparation, purification and/or sterilization requirements for reagents used in the assays. The compositions, methods and reaction mixtures of the invention have particular advantages for the testing raw materials used in the production of products for the biotech, pharma, cosmetics and beverage industries, for release testing of final products, and for sterility screening to test for a class of organisms or total viable organisms in a material of interest (bacterial, fungal or both). In the clinical setting, the methods and reaction mixtures of the invention would be particularly useful for sepsis testing, especially septicemia, which is caused by pathogenic organisms and/or their toxins in the bloodstream.

Methods using the inactivatable target capture oligomers of the current invention can comprise an initial step of selectively hybridizing and capturing a target nucleic acid followed by a subsequent nucleic acid analysis of said target nucleic acid. By way of example only, a common nucleic acid analysis is an amplification and detection assay. One exemplary amplification reaction comprises using an amplification oligomer to introduce a tag sequence into the first amplification product, and an additional amplification oligomer that hybridizes to said tag sequence (or complement thereof) to generate secondary amplification products. Such is only an exemplary method, and any type of downstream nucleic acid analysis, including amplification assays as well as other types of assays, can be performed on selectively hybridized and captured target nucleic acids. For the exemplary amplification reaction, following selective hybridization and capture of a target nucleic acid under a first set of conditions and then inactivation of unhybridized inactivatable target capture oligomers under a second set of conditions, a heterologous amplification oligomer comprising first and second regions is used in a first amplification reaction to introduced a tag sequence into the target nucleic acid sequence. Thus, said first region of said heterologous amplification oligomer comprises a target hybridizing sequence which hybridizes to a 3'-end of the target nucleic acid sequence and said second region comprising a tag sequence situated 5' to said target hybridizing sequence, and where said tag sequence does not stably hybridize to a target nucleic acid containing the target nucleic acid sequence. Using this heterologous amplification oligomer in a first amplification reaction, the first primer extension product introduces this tag sequence into the target nucleic acid sequence, providing a sequence that is later targeted by a subsequent amplification oligomers. In one alternative aspect, this tag sequence is provided by incorporation of the tag-closing region of the inactivatable target capture oligomer. This aspect is accomplished, for example, by providing an inactivatable target capture oligomer that also serves as a primer for a first synthesis of a complementary strand of the target nucleic acid sequence. Here, the inactivatable target capture oligomer comprises a tag sequence, which can be either a forth region of the inactivatable target capture oligomer, can be a region that contains all or part of the tag-closing region or it can be the tag-closing sequence. Subsequent amplification then utilizes an amplification oligomer member that hybridizes with the tag region. Preferably, a wash step is included following hybridization of the inactivatable target capture oligomer or, in embodiments using a heterologous amplification oligomer comprising a tag sequence, the wash step follows the hybridization of the inactivatable target capture oligomer and the heterologous amplification oligomer. The wash step will remove inactivated and unhybridized inactivatable target capture oligomers and other nucleic acid components in the reaction mixture. The first synthesis of a complementary strand then takes place without the presence of these other nucleic acids in the reaction mixture. Subsequently introduced contaminants are not amplified because these contaminants were neither captured nor do they have the tag sequence introduced into their sequences.

Embodiments wherein said target nucleic acid is modified to include a tag sequence for subsequent hybridization by a heterologous amplification oligomer, said tag sequence can be introduced by using the inactivatable target capture oligomer for a primer-based reaction, thus incorporating the tag sequence into the amplification product, or, preferably, using a heterologous amplification oligomer in a primer-based reaction to similarly incorporate the tag sequence into an amplification product. In a preferred embodiment, a heterologous amplification oligomer comprising a tag sequence and a target hybridizing sequence is hybridized to said target nucleic acid. Preferably, following hybridization of said heterologous amplification oligomer to said target nucleic acid, the target nucleic acid, target capture oligomer and heterologous amplification oligomer complex is captured and the remaining components in the mix are washed away; including uncaptured and inactive inactivatable target capture oligomer, unhybridized heterologous amplification oligomer and non-target nucleic acids. A polymerase is then added to make a complementary target nucleic acid sequence from said heterologous amplification oligomer. The resulting complementary target nucleic acid sequence has said tag sequence incorporated therein. The presence of non-target nucleic acids was substantially reduced or eliminated in the wash step. The presence of unhybridized heterologous amplification oligomer was substantially reduced or eliminated in the wash step. The presence of inactive and unhybridized inactivatable target capture oligomer was substantially reduced or eliminated in the wash step. Amplification of subsequently introduced contaminant is thusly substantially reduced or eliminated, too, because of a lack of these reagents.

Preferably, following said step of making a complementary target nucleic acid sequence from said heterologous amplification oligomer, an amplification reaction is performed using at least two amplification oligomers, one of which is complementary to said incorporated tag sequence. In this way, the amplification of subsequently introduced contaminants is substantially reduced or eliminated because the amplification reaction is directed towards nucleic acids containing said tag sequence. These subsequently used amplification oligomers include primer oligomers and promoter-based oligomers, such as a promoter primer or a promoter provider. Exemplary amplification reactions are as follows:

A first amplification method comprises the steps of: (a) treating a target nucleic acid complex immobilized on a solid support, with a heterologous amplification oligomer comprising a tag sequence to produce a heterologous amplification oligomer:target nucleic acid complex; (b) reducing in said sample the effective concentration of heterologous amplification oligomer sequences that have not formed part of said complex; and (c) subjecting said target nucleic acid sequence to reagents and conditions sufficient for incorporation of said tag sequence into said target nucleic acid sequence and then for detectable amplification of the target nucleic acid sequence, where the subjecting step exposes the sample to a known contaminating source of the target nucleic acid sequence after step (b), and where detectable amplification of the target nucleic acid sequence is substantially limited to amplification of target nucleic acid sequence contributed by the tag sequence of step (a) and not by the known contaminating source.

In one aspect of this embodiment, one or more reagents used in the methods, such as nucleic acid polymerases, are produced using a microorganism containing the contaminating nucleic acid sequence. In a further aspect, components used in the methods, such as reaction vessels, pipette tips and solid supports for binding complexes comprising the captured target nucleic acid sequences, may be a known contaminating source of the target nucleic acid sequence. In a further aspect, the methods are useful where the environmental conditions in which amplification is performed include a known contaminating source of a nucleic acid sequence, such as the ambient air, operator or analytical instrumentation.

In a further aspect of this embodiment, the captured target nucleic acid sequence is immobilized on a solid support during step (b). Preferably, the target nucleic acid sequence and inactivatable target capture oligomer complex is immobilized on a solid support during step (b). More preferably, the target nucleic acid sequence, inactivatable target capture oligomer and heterologous amplification oligomer complex is immobilized on a solid support during step (b).

In further aspect, step (b) comprises diluting or removing inactivatable target capture oligomers that have not hybridized to target nucleic acid sequences. Preferably, step (b) comprises diluting or removing inactivatable target capture oligomers and heterologous target amplification oligomers that have not hybridized to target nucleic acid sequences.

In an alternative aspect, an inactivatable target capture oligomer may be inactivated by blocking its ability to complex with a target nucleic acid sequence by using an enzyme to digest a component or cleave a site of a portion of its nucleic acid sequence, chemically altering the sequence, or altering by other means the ability of the target hybridization sequence to complex with a nucleic acid sequence in a reaction mixture.

In yet another aspect, the target hybridizing sequence of said inactivatable target capture oligomer, in certain aspects, is a universal oligonucleotide, such as a universal bacterial or fungal oligonucleotide. In yet another aspect, the target hybridizing sequence of said heterologous amplification oligomer, in certain aspects, is a universal oligonucleotide, such as a universal bacterial or fungal oligonucleotide. In yet another aspect, the target hybridizing sequence of said inactivatable target capture oligomer and the target hybridizing sequence of said heterologous amplification oligomer are both universal oligonucleotide sequences, such as a universal bacterial or fungal oligonucleotide.

Step (c) comprises producing amplification products in a nucleic acid amplification reaction, wherein a complement of said target nucleic acid is made using the heterologous amplification oligomer thus resulting incorporating therein the tag sequence, and then using first and second amplification oligonucleotides, wherein the first oligonucleotide comprises a sequence which hybridizes to a 3'-end of the incorporated tag sequence but which does not stably hybridize to the target nucleic acid sequence or the complement of the target nucleic acid sequence and a second oligonucleotide comprising, wherein each of the amplification products comprises a base sequence which is substantially identical or complementary to the base sequence of the target nucleic acid sequence and all or a portion of the tag sequence.

Various amplification methods are suitable for use in the present invention. For example, in one aspect, the amplification reaction is a PCR reaction. In another aspect, the target nucleic acid sequence is amplified by a transcription-based amplification reaction, preferably a TMA reaction, performed under isothermal conditions.

The target nucleic acid sequence amplified according to the methods can be any target nucleic acid sequence of interest, but will generally be a nucleic acid sequence obtained from a microorganism. Further, the method can be selective for the amplification of a target nucleic acid sequence contained in the nucleic acid of a single strain or species of microorganisms or in multiple species of microorganisms. Alternatively, the method can be selective for the amplification of multiple target nucleic acid sequences contained in the nucleic acid of multiple species of microorganisms, where, for example, the target hybridizing sequence of an inactivatable target capture oligomer hybridizes to a target region present in each of the multiple target nucleic acid sequences in step (a).

For example, in a particular aspect, the method is selective for the amplification of a target nucleic acid sequence contained in each of a plurality of target nucleic acids, and wherein the heterologous tag sequence produces a tagged target nucleic acid sequence with the target nucleic acid sequence of each of the plurality of target nucleic acids present in the nucleic acid sample in step (a). In a more particular aspect, the target nucleic acid sequence contained in each of the plurality of target nucleic acids is the same nucleic acid sequence.

In another particular aspect, the method is selective for the amplification of multiple bacterial or fungal target nucleic acid sequences, e.g., wherein the multiple bacterial or fungal target nucleic acid sequences are ribosomal nucleic acid sequences. In another particular aspect, the method is selective for the amplification of target nucleic acid sequences obtained from members of a group of bacterial species. In another aspect, the method is selective for the amplification of target nucleic acid sequences obtained from members of a group of fungal species. In another particular aspect, the method is selective for the microorganisms that would be detected in a sepsis test. In yet another aspect, at least a portion of a nucleic acid sample used in the methods is obtained from a clinical, water, industrial, environmental, seed, beverage or food source. The methods are particularly well suited, in certain aspects, for use in sterility testing or diagnostic testing for sepsis.

A further amplification method comprises the steps of: (a) treating a nucleic acid sample comprising a target nucleic acid sequence with an inactivatable target capture oligomer and a heterologous amplification oligomer under a set of conditions for selective hybridization of the inactivatable target capture oligomer and a heterologous amplification oligomer to the target nucleic acid; (b) reducing in said nucleic acid sample the effective concentration of unhybridized inactivatable target capture oligomer having an active form in which a target hybridizing sequence of said unhybridized inactivatable target capture oligomer is available for hybridization to said a non-target and/or contaminating nucleic acid sequence; and (c) producing amplification products in a nucleic acid amplification reaction using the heterologous amplification oligomer to incorporate a tag sequence into the complementary target nucleic acid sequence then using first and second oligonucleotides to amplify the target nucleic acid, where the first oligonucleotide comprises a hybridizing sequence which hybridizes to a 3'-end of the complement of the target nucleic acid sequence and the second oligonucleotide comprises a hybridizing sequence which hybridizes to the complement of the tag sequence, but does not stably hybridize to the target nucleic acid, and where the amplification products comprises a base sequence which is substantially identical to or complementary to the base sequence of the target nucleic acid sequence and all or a portion of the tag sequence.

In one aspect of the above methods, at least one target nucleic acid sequence is immobilized on a solid support during step (b). In another aspect, step (b) does not include the use of an enzyme having a nuclease activity.

The effective concentration of unhybridized inactivatable target capture oligomer in an active form prior to amplification is preferably reduced by diluting the nucleic acid sample or by inactivating and/or removing the unhybridized inactivatable target capture oligomer. In one aspect, step (b) comprises inactivating unhybridized inactivatable target capture oligomer so that it does not stably hybridize to any nucleic acid sequence during step (c). In one example of inactivation, an inactivatable target capture oligomer has an active form during step (a) which permits the target hybridizing sequence to hybridize to the target nucleic acid sequence, and where unhybridized inactivatable target capture oligomer is converted to an inactive form in step (b) which blocks or prevents its hybridizing to the target nucleic acid sequence during step (c). In a related embodiment, the conditions of steps (b) and (c) are less stringent than the conditions of step (a). In another related embodiment, the temperature of the nucleic acid sample is lowered between steps (a) and (b).

In another alternative example, unhybridized inactivatable target capture oligomer from step (a) is converted from a single-stranded form to a duplexed form in step (b). The duplexed form may be a hairpin molecule comprising a tag-closing sequence, where the tag-closing sequence hybridizes to the target hybridizing sequence under the conditions of step (b), thereby blocking hybridization of unhybridized inactivatable target capture oligomer from step (a) to the target nucleic acid sequence in steps (b) and (c). In another aspect, the tag-closing sequence is joined to the inactivatable target capture oligomer by a non-nucleotide linker. In orientations of the inactivatable target capture oligomer wherein a terminal 3' residue is available for primer based nucleic acid extension and such extension is not desired, then the 3' terminal residue can be blocked using a blocking moiety.

In still another aspect, the target hybridizing sequence is hybridized to a tag-closing oligonucleotide in step (b), the inactivatable target capture oligonucleotide and the tag-closing oligonucleotide being distinct molecules. The tag-closing oligonucleotide may be modified, if desired, to prevent the initiation of DNA synthesis therefrom.

Further, in certain aspects, a 3'-terminal base of the target hybridizing sequence is hybridized to a 5'-terminal base of the tag-closing oligonucleotide.

As noted above, the methods of the invention can employ any of a variety of amplification techniques. In certain instances it may be preferred that an isothermal amplification reaction is used, such as a transcription-based amplification reaction, preferably TMA or real-time TMA.

In a particular aspect, the first amplification oligonucleotide comprises a promoter sequence for an RNA polymerase the promoter sequence being situated 5' to the target hybridizing sequence. In another aspect, the second oligonucleotide comprises a promoter sequence for an RNA polymerase, the promoter sequence being situated 5' to the target hybridizing sequence. In a further aspect, one or both of the first or second amplification oligomers comprises a target hybridizing region, a tag sequence region and a promoter sequence region for an RNA polymerase, wherein the promoter sequence is situated 5' to the tag sequence region.

The nucleic acid sample is often exposed to a known contaminating source after step (b), and, accordingly, the described methods provide that the production of amplification products is substantially limited to amplification of target nucleic acid sequence contributed by the nucleic acid sample and not by the contaminating nucleic acid sequence. For example, one or more reagents or components used in the amplification reaction comprise a known contaminating source. Alternatively, or in addition, one or more reagents are produced with a material known to be a contaminating source; such as nucleic acid polymerases produced using microorganisms known to contain the target nucleic acid sequence. Further, the environmental conditions in which the method is performed may include a known contaminating source. In a particular aspect, at least a portion of said nucleic acid is obtained from clinical, water, industrial, environmental, seed, beverage or food sources.

According to a third exemplary amplification method, the target nucleic acid sequence is an RNA target sequence, and step (c) comprises: extending the heterologous amplification oligomer hybridized to the target nucleic acid sequence in a primer extension reaction with a DNA polymerase to produce an extension product comprising a region complementary to the target nucleic acid sequence and a tag sequence; separating the extension product from the target nucleic acid using an enzyme which selectively degrades that portion of the target nucleic acid hybridized to the extension product; treating the extension product with a first amplification oligonucleotide, the first amplification oligonucleotide being a promoter oligonucleotide comprising a hybridizing sequence which hybridizes to a region of the extension product that is complementary to a 5'-end of the target nucleic acid sequence to form a promoter oligonucleotide: extension product hybrid, and comprising a promoter sequence for an RNA polymerase, the promoter sequence being situated 5' to the target hybridizing region; transcribing with an RNA polymerase using as a template the promoter oligonucleotide:extension product complex multiple copies of a first RNA product complementary to at least a portion of the extension product and incorporated tag sequence; treating the first RNA product with the second amplification oligonucleotide that hybridizes to the complement of the tag sequence to form a second amplification oligonucleotide:first RNA product complex such that a primer extension reaction can be initiated from the second amplification oligonucleotide; extending the second amplification oligonucleotide in a primer extension reaction with a DNA polymerase to produce a second primer extension product complementary to the first RNA product, the second primer extension product having a 3'-end which is complementary to a 5'-end of the first RNA product; separating the second primer extension product from the first RNA product using an enzyme which selectively degrades said first RNA product; treating the second primer extension product with the promoter oligonucleotide to form a promoter oligonucleotide:second primer extension product complex; extending a 3'-end of the second primer extension product in the promoter oligonucleotide:second primer extension product complex to add a sequence complementary to the second region of the promoter oligonucleotide; and transcribing from the promoter oligonucleotide:second primer extension product hybrid multiple copies of a second RNA product complementary to the second primer extension product using the RNA polymerase.

In another aspect of this embodiment of the invention, step (a) further comprises treating the nucleic acid sample with a binding molecule which binds to the target nucleic acid adjacent to or near a 5'-end of the target nucleic acid sequence, and where the first primer extension product has a 3'-end which is determined by the binding molecule and which is complementary to the 5'-end of the target nucleic acid sequence.

In another aspect, step (c) of the above embodiment further comprises extending a 3'-end of the first primer extension product in the promoter oligonucleotide:first primer extension product hybrid to add a sequence complementary to the promoter. In yet another aspect, the promoter oligonucleotide is modified to prevent the initiation of DNA synthesis therefrom.

The promoter oligonucleotide hybridized to the first primer extension product is extended with a DNA polymerase to produce a primer extension product complementary to the first primer extension product; and the promoter oligonucleotide hybridized to said second primer extension product is extended with a DNA polymerase to produce a primer extension product complementary to the second primer extension product.

The separating steps of the described methods may be performed with a ribonuclease activity provided by the DNA polymerase. Alternatively, the separating steps are performed with a ribonuclease activity provided by an enzyme other than said DNA polymerase.

According to a forth amplification method, the target nucleic acid sequence is an RNA target sequence, and step (c) comprises: extending the heterologous amplification oligomer hybridized to the target nucleic acid sequence in a primer extension reaction with a DNA polymerase to produce a first primer extension product comprising a region complementary to the target nucleic acid sequence and a tag sequence, where the heterologous amplification oligonucleotide further comprises a third region situated 5' to the tag sequence, the third region comprising a promoter for an RNA polymerase; separating the first primer extension product from the target nucleic acid using an enzyme which selectively degrades that portion of the target nucleic acid hybridized to the first primer extension product; treating the first primer extension product with a first amplification oligonucleotide, the first amplification oligonucleotide being a priming oligonucleotide which hybridizes to a region of the first primer extension product that is complementary to a 5'-end of the target nucleic acid sequence to form a first amplification oligonucleotide:first primer extension product complex such that a primer extension reaction can be initiated from the first amplification oligonucleotide; extending the first amplification oligonucleotide in a primer extension reaction with a DNA polymerase to produce a second primer extension product complementary to the first primer extension product; and using the second primer extension product as a template to transcribe multiple copies of a first RNA product complementary to at least a portion of the second primer extension product using an RNA polymerase which recognizes the promoter and initiates transcription therefrom, where the base sequence of the first RNA product is substantially identical to the base sequence of the tag sequence and the complement of the target nucleic acid sequence.

In another aspect of this embodiment, step (c) further comprises: treating the first RNA product with the second amplification oligonucleotide to form a priming oligonucleotide: first RNA product complex such that a primer extension reaction can be initiated from the second amplification oligonucleotide; extending the priming oligonucleotide in a primer extension reaction with a DNA polymerase to produce a third primer extension product complementary to the first RNA product, the third primer extension product having a 3'-end which is complementary to a 5'-end of the first RNA product; separating the third primer extension product from the first RNA product using an enzyme which selectively degrades the first RNA product; treating the third primer extension product with the second oligonucleotide, the second oligonucleotide being a promoter oligonucleotide comprising first and second regions, the first region comprising a hybridizing sequence which hybridizes to the complement of the tag sequence to form a promoter oligonucleotide:third primer extension product hybrid such that a primer extension reaction can be initiated from the promoter oligonucleotide, and the second region comprising a promoter for an RNA polymerase which is situated 5' to the first region; extending the promoter oligonucleotide in a primer extension reaction with the DNA polymerase to produce a fourth primer extension product complementary to the third primer extension product; extending the third primer extension product to add a sequence complementary to the promoter; transcribing from the promoter oligonucleotide:third primer extension product hybrid multiple copies of a second RNA product complementary to the third primer extension product using an RNA polymerase which recognizes the promoter and initiates transcription therefrom, where the base sequence of the second RNA product is substantially identical to the base sequence of the tag sequence and the complement of the target nucleic acid sequence.

In another aspect of this embodiment, the separating steps are performed with a ribonuclease activity provided by the DNA polymerase. Alternatively, the separating steps are performed with a ribonuclease activity provided by an enzyme other than the DNA polymerase.

According to fifth amplification method, the target nucleic acid sequence is a DNA target sequence, and step (c) comprises: extending the heterologous amplification oligomer hybridized to the target nucleic acid sequence in a primer extension reaction with a DNA polymerase to produce a first primer extension product comprising a region complementary to the target nucleic acid sequence a the tag sequence; treating the first primer extension product with the first amplification oligonucleotide, the first amplification oligonucleotide being a promoter oligonucleotide comprising a target hybridizing sequence which hybridizes to a region of the first primer extension product that is complementary to a 5'-end of the target nucleic acid sequence to form a promoter oligonucleotide:first primer extension product hybrid, and the second region being a promoter for an RNA polymerase which is situated 5' to the first region; transcribing from the promoter oligonucleotide:first primer extension product complex multiple copies of a first RNA product complementary to at least a portion of the first primer extension product using an RNA polymerase that recognizes the promoter and initiates transcription therefrom, where the base sequence of the first RNA product is substantially identical to the base sequence of the target nucleic acid sequence and the complement of the tag sequence; treating the first RNA product with the second amplification oligonucleotide, the second amplification oligonucleotide being a priming oligonucleotide which hybridizes to the complement of the tag sequence to form a priming oligonucleotide:first RNA product hybrid such that a primer extension reaction can be initiated from the priming oligonucleotide; extending the priming oligonucleotide in a primer extension reaction with a DNA polymerase to give a second primer extension product comprising the complement of the first RNA product, the second primer extension product having a 3'-end which is complementary to a 5'-end of the first RNA product; separating the second primer extension product from the first RNA product using an enzyme which selectively degrades the first RNA product; treating the second primer extension product with the promoter oligonucleotide to form a promoter oligonucleotide:second primer extension product hybrid; extending a 3'-end of the second primer extension product in the promoter oligonucleotide:second primer extension product hybrid to add a sequence complementary to the promoter; and transcribing from the promoter oligonucleotide:second primer extension product hybrid multiple copies of a second RNA product complementary to the second primer extension product using the RNA polymerase, where the base sequence of the second RNA product is substantially identical to the base sequence of the target nucleic acid sequence and the complement of the tag sequence.

In one aspect of this embodiment, the promoter oligonucleotide is modified to prevent the initiation of DNA synthesis therefrom.

In another aspect, step (a) further comprises: treating the nucleic acid sample with a displacer oligonucleotide which hybridizes to the target nucleic acid upstream from the heterologous amplification oligonucleotide such that a primer extension reaction can be initiated from the displacer oligonucleotide; and extending the displacer oligonucleotide in a primer extension reaction with a DNA polymerase to produce a third primer extension product that displaces said first primer extension product from the target nucleic acid.

In yet another embodiment, step (a) further comprises treating the nucleic acid sample with a binding molecule which binds to the target nucleic acid adjacent to or near a 5'-end of the target nucleic acid sequence, where the first primer extension product has a 3'-end which is determined by said binding molecule and which is complementary to the 5'-end of the target nucleic acid sequence.

In a more particular aspect, step (c) further comprises extending a 3'-end of the first primer extension product in the promoter oligonucleotide: first primer extension product complex to add a sequence complementary to the promoter sequence.

In another particular aspect, step (c) further comprises: extending the promoter oligonucleotide hybridized to the first primer extension product with a DNA polymerase to produce a primer extension product complementary to the first primer extension product; and extending the promoter oligonucleotide hybridized to the second primer extension product with a DNA polymerase to produce a primer extension product complementary to the second primer extension product.

The separating steps, in one embodiment, are performed by a ribonuclease activity provided by said DNA polymerase. Alternatively, the separating steps are performed by a ribonuclease activity provided by an enzyme other than said DNA polymerase.

Another embodiment of the present invention provides a kit for use in the selective hybridization of at least one inactivatable target capture oligomer to at least one target nucleic acid sequence from a nucleic acid sample, the kit comprising: an inactivatable target capture oligomer comprising a first region comprising a target hybridizing sequence which hybridizes to a target nucleic acid sequence under a first set of conditions, a second region comprising a tag-closing sequence situated, preferably, 3' to the first region, where the second region does not stably hybridize to a target nucleic acid under the first set of conditions and third region comprising a binding pair member situated, preferably, 3' to the second region. In one aspect, said kit further comprises a solid support comprising a second binding pair member that is complementary to the binding pair member of the inactivatable target capture oligomer. In a further aspect, the solid support is a magnetic bead. In a further aspect, the first binding pair member of the inactivatable target capture oligomer and the second binding pair member of the solid support are complementary nucleic acid sequences, preferably said sequences are substantially homopolymeric.

In a further embodiment, said kit comprises a heterologous amplification oligomer comprising a target hybridizing region that hybridizes to target nucleic acid sequence and a tag sequence that doe not stably hybridize to the target nucleic acid sequence. In a further embodiment, the kit comprises at least two amplification oligomers, one of which is hybridizes to the tag sequence, or complement thereof. Amplification oligomers include primers, promoter-based amplification oligomer and heterologous amplification oligomers. In a further embodiment, the kit comprises a terminating oligomer.

In yet another aspect, the tag-closing sequence includes a moiety for stabilizing a duplex formed between the tag-closing sequence and the target hybridizing sequence when the target hybridizing sequence is not hybridized to the target nucleic acid sequence under the second set of conditions.

In another and alternative aspect, the inactivatable target capture oligonucleotide comprises a tag-closing sequence that constitutes a distinct molecule from the molecule comprising the target hybridizing sequence and the binding pair member.

The tag-closing sequence may be joined to the target hybridizing region by a non-nucleotide linker, for example a non-nucleotide linker comprising at least one of abasic nucleotides and polyethylene glycol. In another aspect, a 3'-end of the tag-closing sequence is joined to a 5'-end of the target hybridizing region. Alternatively, a 5'-end of the tag-closing sequence is joined to a 5'-end of the target hybridizing region. Alternatively, the tag-closing region and the target hybridizing region are joined in a 5'-to '5' or 3' to '3' orientation using a non-nucleotide linker. In yet another aspect, the tag-closing sequence hybridizes to the target hybridizing sequence to form an antiparallel duplex when the target hybridizing sequence is not hybridized to the target nucleic acid sequence under the second set of conditions. In other aspects wherein the orientation and/or arrangement of the regions of the inactivatable target capture oligomer provides a terminal 3' end that can be extended by a polymerase in a priming event and wherein such extension is not desired, the 3' terminal nucleotide of a sequence is modified to prevent the initiation of DNA synthesis therefrom, for example by including a blocking moiety situated at its 3'-terminus.

In another aspect, the tag-closing sequence hybridizes to the target hybridizing sequence to form a parallel duplex when the target hybridizing sequence is not hybridized to the target nucleic acid sequence under the second set of conditions.

In yet another aspect, the duplex comprises a 3'-terminal base of the target hybridizing sequence hybridized to a 3'-terminal base of the tag-closing sequence. In another aspect of this embodiment, the first priming oligonucleotide does stably hybridize to the target nucleic acid and, thereby, participates in detectable amplification of the target nucleic acid sequence under the second set of conditions. In another aspect, the kit further comprises a second priming oligonucleotide which hybridizes to the complement of a 5'-end of the target nucleic acid sequence under the second set of conditions so that the second priming oligonucleotide can be extended in a template-dependent manner in the presence of a DNA polymerase. In yet another aspect, a kit of the invention further comprises a promoter oligonucleotide comprising first and second regions, the first region comprising a hybridizing sequence which hybridizes to the complement of a 5'-end of the target nucleic acid sequence under the second set of conditions, and the second region comprising a promoter for an RNA polymerase which is situated 5' to the first region. The promoter oligonucleotide, in this aspect, may be modified to prevent the initiation of DNA synthesis therefrom, for example by including a blocking moiety situated at its 3'-terminus. In yet another aspect, the promoter oligonucleotide can be extended in a template-dependent manner in the presence of a DNA polymerase when the hybridizing sequence is hybridized to the complement of the 5'-end of the target nucleic acid sequence under the second set of conditions.

The kits of the invention, in certain aspects, may also further comprise one or more reagents or components selected from any one or more of a DNA polymerase (such as a reverse transcriptase), an RNA polymerase, nucleoside triphosphates, a solid support for binding a complex comprising the target nucleic acid and the inactivatable target capture oligonucleotide. In another aspect, the inactivatable target capture is free in solution. In another aspect, the kit does not include a restriction enzyme capable of cleaving a duplex formed between the tag-closing sequence and the target hybridizing sequence under the second set of conditions. In yet another aspect, the target hybridizing sequence hybridizes to a 3'-end of multiple target nucleic acid sequences under the first set of conditions.

According to another embodiment of the invention, there is provided a preannealing reaction mixture for stably hybridizing an active inactivatable target capture oligomer to target nucleic acid sequence under a first set of conditions. In another embodiment, there is provided a preannealing reaction mixture for stably hybridizing an active inactivatable target capture oligomer and a heterologous amplification oligomer to target nucleic acid sequence under a first set of conditions. In another embodiment there is provided a preannealing reaction mixture for stably hybridizing an active inactivatable target capture oligomer and, optionally, a heterologous amplification oligomer to target nucleic acid sequence under a first set of conditions, and for inactivating unhybridized and active inactivatable target capture oligomer under a second set of conditions. In another embodiment there is provided a preannealing reaction mixture for stably hybridizing an active inactivatable target capture oligomer and a heterologous amplification oligomer to target nucleic acid sequence under a first set of conditions, for inactivating unhybridized and active inactivatable target capture oligomer under a second set of conditions, and for reducing or eliminating non-target nucleic acid, inactivated target capture oligomer and heterologous amplification oligomer from the reaction mixture. In another embodiment there is provided a preannealing reaction mixture for stably hybridizing an active inactivatable target capture oligomer and a heterologous amplification oligomer to target nucleic acid sequence under a first set of conditions, for inactivating unhybridized and active inactivatable target capture oligomer under a second set of conditions, and for reducing or eliminating non-target nucleic acid, inactivated target capture oligomer and heterologous amplification oligomer from the reaction mixture, wherein said target nucleic acid is subsequently used in a nucleic acid analysis assay. In another embodiment there is provided a preannealing reaction mixture for stably hybridizing an active inactivatable target capture oligomer and a heterologous amplification oligomer to a target nucleic acid sequence under a first set of conditions, for inactivating unhybridized and active inactivatable target capture oligomer under a second set of conditions, and for reducing or eliminating non-target nucleic acid, inactivated target capture oligomer and heterologous amplification oligomer from the reaction mixture, wherein said heterologous amplification oligomer is used to make a complementary copy of the target nucleic acid containing the tag sequence.

In yet another aspect, the inactivatable target capture oligonucleotide is not attached to a solid support.

Certain other embodiments of the invention relate to the use of the methods described herein as a means for monitoring bioprocess samples, streams, and the like. In one embodiment, for example, there is provided a method for monitoring a bioprocess for the presence of contaminating nucleic acid comprising the steps of (a) treating a first bioprocess sample with inactivatable target capture oligomer and, optionally, a heterologous amplification oligomer under conditions wherein the inactivatable target capture oligomer and the heterologous amplification oligomer, if present, stably hybridize to the target nucleic acid sequence present in said first sample; (b) removing or inactivating unhybridized inactivatable target capture oligomer from the first bioprocess sample; and (c) exposing a second bioprocess sample, the second bioprocess sample comprising the first bioprocess sample and further comprising additional bioprocess samples, to amplification reagents and conditions sufficient for amplification of the target nucleic acid sequence using an amplification reaction generally as described or referenced herein.

In another embodiment, the present invention provides a method for monitoring a bioprocess for the presence of contaminating nucleic acid comprising the steps of (a) treating a first bioprocess sample with a first inactivatable target capture oligomer and, optionally, a first heterologous amplification oligomer under conditions where the first inactivatable target capture oligomer and the first heterologous amplification oligomer, if present, stably hybridize to the target nucleic acid sequence present in said first sample; (b) treating a second bioprocess sample with a second inactivatable target capture oligomer and, optionally, a second heterologous amplification oligomer; under conditions where the second inactivatable target capture oligomer and the second heterologous amplification oligomer, if present, stably hybridize to the target nucleic acid sequence present in the second sample; and (c) performing a nucleic acid amplification reaction on a third bioprocess sample, the third bioprocess sample comprising the first and the second bioprocess samples, using: (i) a first amplification oligonucleotide which hybridizes to a complement of the first tag sequence; (ii) a second amplification oligonucleotide sequence which hybridizes to a complement of the second tag sequence; and (iii) a third amplification oligonucleotide which hybridizes to a complement of the target nucleic acid sequence; where the detection of amplification product resulting from the first and third amplification oligonucleotides is indicative of the presence of the target nucleic acid sequence of the organism of interest in the first bioprocess sample, and where detection of amplification product resulting from the second and third oligonucleotides is indicative of the presence of the target nucleic acid sequence of the organism of interest in the second bioprocess sample.

In a further embodiment of the invention, a pre-amplification reaction mixture is provided for the selective amplification of one or more target nucleic acid sequences, where the reaction mixture comprises: an inactivatable target capture oligomer hybridized to a target nucleic acid and a heterologous amplification oligomer hybridized to a target region contained at a 3'-end of one or more target nucleic acid sequences present in the reaction mixture; a first amplification oligonucleotide comprising a target hybridizing sequence which hybridizes to a 3'-end of the complement of one or more of the target nucleic acid sequences; and a second amplification oligonucleotide comprising a hybridizing sequence which hybridizes to the complement of the tag sequence, where the second amplification oligonucleotide preferably does not stably hybridize to a target nucleic acid, where the reaction mixture is substantially free of an active form of the inactivatable target capture oligomer oligomer, and where the reaction mixture does not include a nucleic acid polymerase capable of extending any of the oligonucleotides in a template-dependent manner. The "non-target" nucleic acid is from a source outside of the reaction mixture and may contain a sequence identical to that of the target nucleic acid sequence. The source of the non-target nucleic acid may be environmental or it may be a component or reagent added to the reaction mixture, such a nucleic acid polymerase. Each one of the heterologous amplification oligomer, first amplification oligomer or second amplification oligomer can be a priming oligonucleotide or a promoter-based oligonucleotide.

In one embodiment, inactivatable target capture oligomers that have not hybridized to the target region of at least one target nucleic acid sequence remain "free" in the reaction mixture (i.e., the inactivatable target capture oligomers do not form hybrid duplexes other than through self-hybridization). Self-hybridized inactivatable target capture oligomers are referred to as "hairpin tag molecules," which are the inactive forms of the molecule that prevents it from hybridizing to any complementary nucleic acids that are subsequently added to the reaction mixture, such as through a contaminated enzyme preparation or reagent containing non-target nucleic acids. In still another aspect of this embodiment, substantially all of the inactivatable target capture oligomers in the reaction mixture are in a hybridized state (hybridized either to the target region of a target nucleic acid sequence or to themselves in the form of hairpin tag molecules). At least a portion of the tag molecules which have not hybridized to the target region of a target nucleic acid sequence (i.e., hairpin tag molecules) are removed from the reaction mixture by, for example, subjecting the reaction mixture to a target capture and washing procedure.

In a still further aspect of this embodiment, there are substantially no inactivatable target capture oligomers that exist in an unhybridized state when the reaction mixture is exposed to an enzyme preparation for amplifying the one or more target nucleic acid sequences. Thus, in this aspect, the reaction mixture is substantially depleted of unhybridized inactivatable target capture oligomers specific for the one or more target nucleic acid sequences provided by the sample of interest. More preferably, the reaction mixture is further substantially depleted of self-hybridized (inactivated) inactivatable target capture oligonucleotides. This may be accomplished with, for example, a target capture, reaction mixture conditions and washing procedure that separate hybridized inactivatable target capture oligonucleotides from unhybridized inactivatable target capture oligonucleotides, and then selectively removes the unhybridized inactivatable target capture oligonucleotides from the reaction mixture.

In some embodiments a probe-based detection assay is performed for detecting target nucleic acid sequences. Thus in one aspect, a probe is included for detecting an amplification product synthesized in an in vitro reaction that involves enzymatic synthesis of a target nucleic acid sequence. In other aspects, a target nucleic acid sequence is captured using the compositions and methods of the current invention and the captures target nucleic acid is detected by direct hybridization of a probe molecule. Amplification products include nucleic acid copies of one or more of the target nucleic acid sequences and/or their complements.

In yet another embodiment, a reaction mixture is provided for the selective amplification of one or more target nucleic acid sequences, where the reaction mixture comprises: inactivatable target capture oligomer; a heterologous amplification oligomer; a first amplification oligonucleotide comprising a hybridizing sequence which hybridizes to a 3'-end of the complement of the target nucleic acid sequence; and a second amplification oligonucleotide comprising a hybridizing sequence which hybridizes to the complement of the tag sequence, where the second amplification oligonucleotide preferably does not stably hybridize to a target nucleic acid containing the target nucleic acid sequence, and where substantially all unhybridized inactivatable target capture oligomer in the reaction mixture has an inactive form which blocks or prevents said unhybridized inactivatable target capture from hybridizing to the target nucleic acid sequence.

The inactive form of the inactivatable target capture oligomer can comprise a tag-closing sequence hybridized to the target hybridizing sequence. The tag-closing sequence can be a distinct molecule when not hybridized to the target hybridizing sequence or it can be an integral part of the inactivatable target capture oligomer sequence. An integral tag-closing sequence can be a continuous nucleotide sequence along with the target hybridizing region or it can be joined to the target hybridizing region using a non-nucleotide linker (i.e., the constituents of the linker cannot be copied by a nucleic acid polymerase). The inactivatable target capture oligomer may or may not be joined to a solid support and is preferably not directly attached to solid support (e.g., particles or beads). If joined to a solid support, either directly or indirectly, the inactivatable target capture oligomer may further function as a capture probe for binding and immobilizing a target nucleic acid sequence.

The inactivatable target capture oligomer of the above reaction mixture embodiments may possess the characterizing features of any of the various inactivatable target capture oligomer embodiments described infra. And, unless specifically excluded, the reaction mixtures may further include the reagents and components needed to conduct an amplification reaction.

These and other features and advantages of the present invention will become apparent upon reference to the following detailed description, the attached drawings and the claims. All references disclosed herein are hereby incorporated by reference in their entirety as if each was incorporated individually.

BRIEF DESCRIPTION OF THE DRAWINGS

FIGS. 1 through 16 illustrate exemplary amplification analysis reactions that can be performed using target nucleic acids that have been captured using the inactivatable target capture oligomers of the current invention.

FIG. 1 illustrates the steps of a transcription-based amplification reaction initiated with a tagged priming oligonucleotide (e.g., a heterologous amplification oligomer) that hybridizes to a 3'-end of an RNA target sequence. A first extension product formed with the tagged priming oligonucleotide has a 3'-end which is determined by a terminating oligonucleotide hybridized adjacent to or near the 5'-end of the RNA target sequence. A blocked promoter oligonucleotide hybridizes to a 3'-end of the first extension product and is used to generate RNA transcripts that are cycled into the amplification reaction.

FIG. 2 illustrates the use of a tag-closing sequence to form a hairpin tagged priming oligomer molecule in the amplification reaction of FIG. 1.

FIG. 4 illustrates the use of a tag-closing sequence to form a hairpin tagged promoter oligonucleotide in the amplification reaction of FIGS. 3A and 3B.

FIG. 5 illustrates the steps of a transcription-based amplification reaction initiated with a heterologous amplification oligomer that is a tagged priming oligonucleotide that hybridizes to a 3'-end of a single-stranded DNA target sequence. A first extension product formed with the tagged priming oligonucleotide has a 3'-end which is determined by a terminating oligonucleotide hybridized adjacent to or near the 5'-end of the DNA target sequence. A displacer oligonucleotide hybridized 5' to the tagged priming oligonucleotide is extended to form a second extension product which displaces the first extension product from the DNA target sequence. A blocked promoter oligonucleotide hybridizes to a 3'-end of the first extension product and is used to generate RNA transcripts that are cycled into the amplification reaction.

FIG. 6 illustrates the use of a tag-closing sequence to form a hairpin tagged priming molecule in the amplification reaction of FIG. 5.

FIG. 7 illustrates the steps of a polymerase chain reaction that is initiated with a heterologous amplification oligomer that is a tagged priming oligonucleotide that hybridizes to a DNA target sequence.

FIG. 8 illustrates the use of a tag-closing sequence to form a hairpin tagged priming molecule in the amplification reaction of FIG. 7.

FIG. 9 illustrates the steps of a reverse transcription polymerase chain reaction initiated with a heterologous amplification oligomer that is a tagged priming oligonucleotide that hybridizes to an RNA target sequence.

FIG. 10 illustrates the use of a tag-closing sequence to form a hairpin tagged priming molecule in the amplification reaction of FIG. 9.

FIG. 11 illustrates a discrete, 3' blocked tag-closing sequence hybridized in an antiparallel fashion to the 3'-end of a tagged priming oligonucleotide, thereby blocking hybridization of the tagged priming oligonucleotide to a target nucleic acid sequence.

FIG. 12 illustrates a discrete, 3' blocked tag-closing sequence hybridized in an antiparallel fashion to the 3'-end of a tagged promoter oligonucleotide, thereby blocking hybridization of the tagged promoter oligonucleotide to a target nucleic acid sequence.

FIG. 13 illustrates a hairpin tag molecule that includes a 3' blocked tag-closing sequence hybridized in a parallel fashion to the 3'-end of a heterologous amplification oligomer that is a tagged priming oligonucleotide, thereby blocking hybridization of the tagged priming oligonucleotide to a target nucleic acid sequence. The 5'-end of the tag-closing sequence is joined by a non-nucleotide linker to the 5'-end of a tag sequence of the tagged priming oligonucleotide.

FIG. 14 illustrates a hairpin tag molecule that includes a 3' blocked tag-closing sequence hybridized in a parallel fashion to the 3'-end of a heterologous amplification oligomer that is a tagged promoter oligonucleotide, thereby blocking hybridization of the tagged promoter oligonucleotide to a target nucleic acid sequence. The 5'-end of the tag-closing sequence is joined by a non-nucleotide linker to the 5'-end of a promoter sequence of the tagged promoter oligonucleotide.

FIG. 15 illustrates a hairpin tag molecule that includes a 3' blocked tag-closing sequence hybridized in an antiparallel fashion to the 3'-end of a heterologous amplification oligomer that is a tagged priming oligonucleotide, thereby blocking hybridization of the tagged priming oligonucleotide to a target nucleic acid sequence. The 5'-end of the tag-closing sequence is joined by a non-nucleotide linker to the 5'-end of a tag sequence of the tagged priming oligonucleotide.

FIG. 16 illustrates a hairpin tag molecule that includes a 3' blocked tag-closing sequence hybridized in an antiparallel fashion to the 3'-end of a heterologous amplification oligomer that is a tagged promoter oligonucleotide, thereby blocking hybridization of the tagged promoter oligonucleotide to a target nucleic acid sequence. The 5'-end of the tag-closing sequence is joined by a non-nucleotide linker to the 5'-end of a promoter sequence of the tagged promoter oligonucleotide.

FIG. 17 shows the raw curves for HCV amplifications in which no target was spiked into the amplification reagent. There was no detectable amplification when the HCV transcript was not spiked into the target capture or amplification reagents, while the average TTime for reactions containing $1 \times 10^6$ copies of the HCV transcript in the target capture reagent was 6.3 minutes.

FIG. 18 shows the raw curves for HCV amplifications in which target was spiked into the amplification reagent. There was no detectable amplification when the HCV transcript was spiked into the amplification reagent, while the average TTime for reactions containing $1 \times 10^6$ copies of the HCV transcript in the target capture reagent was 6.3 minutes. The zero samples in target capture did not amplify, even with 1 million copies HCV 1a spiked into the amplification reagent.

FIG. 19 shows the raw curves for HCV amplifications in which target and tagged nonT7 primer were spiked into the amplification reagent. The Average TTime for 1 million copies HCV 1a target present only in the target capture step with tagged nonT7 primer & terminating oligonucleotide spiked into the amplification reagent was 7.2 minutes. The zero samples in target capture with target, terminating oligonucleotide & tagged nonT7 primer spiked into the amplification reagent also produced robust amplification with an Average TTime=8.6 minutes.

FIG. 20 is graph that shows the results from time-dependent monitoring of nucleic acid amplification reactions that included either 0 or $10^6$ copies of a synthetic *E. coli* rRNA template. The thin broken line shows the results for the reaction conducted using 0 copies of template. The heavy solid line shows the results for the reaction conducted using $10^6$ copies of template.

FIG. 21 is graph that shows the results from time-dependent monitoring of nucleic acid amplification reactions that included 0, $10^3$ or $10^5$ copies of a synthetic *E. coli* rRNA template.

FIG. 22 is an exemplary illustration of inactivatable target capture oligomers wherein the tag-closing sequence is a separate molecule. As is discussed herein, inactivatable target capture oligomers can comprise tail regions and target hybridizing regions in the 5' to 3' orientation or in the 3' to 5' orientation. In an orientation wherein a target hybridizing region comprises a terminal 3' residue, then that residue could be used for primer based extension by a polymerase. If such extension is not desired, then the 3' residue can be blocked. The orientation of the separate tag-closing sequence is determined by the orientation of the target hybridizing region.

FIG. 23 is an exemplary illustration of inactivatable target capture oligomers wherein the tag-closing sequence is joined to the target hybridization region by a non-nucleotide linker. As is discussed herein, inactivatable target capture oligomers can comprise tail regions and target hybridizing regions in the 5' to 3' orientation or in the 3' to 5' orientation. In an orientation wherein a target hybridizing region comprises a terminal 3' residue, then that residue could be used for primer based extension by a polymerase. If such extension is not desired, then the 3' residue can be blocked.

FIGS. 24 and 25 are two exemplary illustrations of inactivatable target capture oligomers wherein the tag-closing sequence is an integral sequence of the target capture oligomer. In FIG. 24, the binding pair member region is joined to the tag-closing region via a non-nucleotide linker. As is discussed herein, inactivatable target capture oligomers can comprise target hybridizing, tag-closing, and binding pair member, if a nucleic acid sequence, that are in either of the 5' to 3' orientation or the 3' to 5' orientation. In an orientation wherein a target hybridizing region comprises a terminal 3' residue, then that residue could be used for primer based extension by a polymerase. If such extension is not desired, then the 3' residue can be blocked.

FIG. 26 illustrates the selective hybridization of an inactivatable target capture oligomer to a target nucleic acid sequence. Selectively hybridized target nucleic acid sequences can be used for any of a number of downstream purposes, as discussed herein. In this illustration the downstream purpose is an amplification reaction. So, the target nucleic acid is optionally hybridized with an amplification oligomer and a blocker. The number of oligomers and target in a reaction will not necessarily be 1:1, thus at each of parts c and d, the point is made that following selective hybridization one or more of the target of nucleic acid reagents can be in excess; denoted by m-o and n-o wherein m, n and o are numbers. The active form of the inactivatable target capture oligomer is illustrated in parts b and c. The hybridized form on the inactivatable capture probe is shown in parts c and d. The inactive form of the inactivatable target capture oligomer is illustrated in part d. The primer and terminating oligomer present in the figure are not required for the selective hybridization and capture of a target nucleic acid. These optional oligomers are illustrated merely for showing the embodiments wherein captures target nucleic acid is subsequently analyzed in an amplification assay.

FIG. 27 illustrates capture of the selectively hybridized target nucleic acid. Following capture, the excess target and/or nucleic acid reagents are removed by a wash. The selectively captured target nucleic acid can then be used in a variety of downstream application, as described herein or as known in the art. In the FIG. 27, the selectively captured target nucleic acid is illustrated as being useful for a downstream amplification reaction in that a primer is additionally hybridized to the target. The primer and terminating oligomer present in the figure are not required for the selective hybridization and capture of a target nucleic acid. These optional oligomers are illustrated merely for showing the embodiments wherein captures target nucleic acid is subsequently analyzed in an amplification assay.

DETAILED DESCRIPTION OF THE INVENTION

Figure 1:
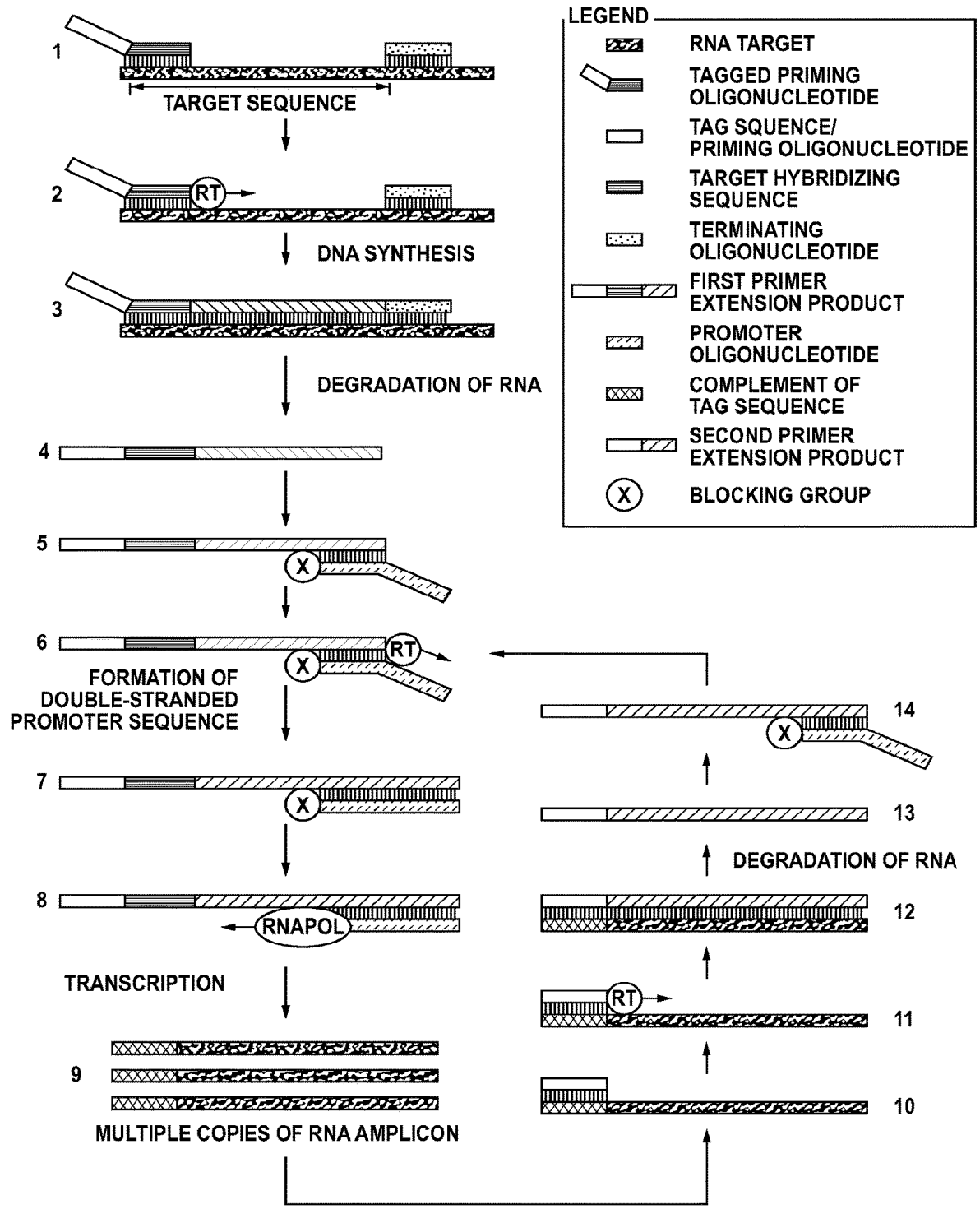
Figure 2:
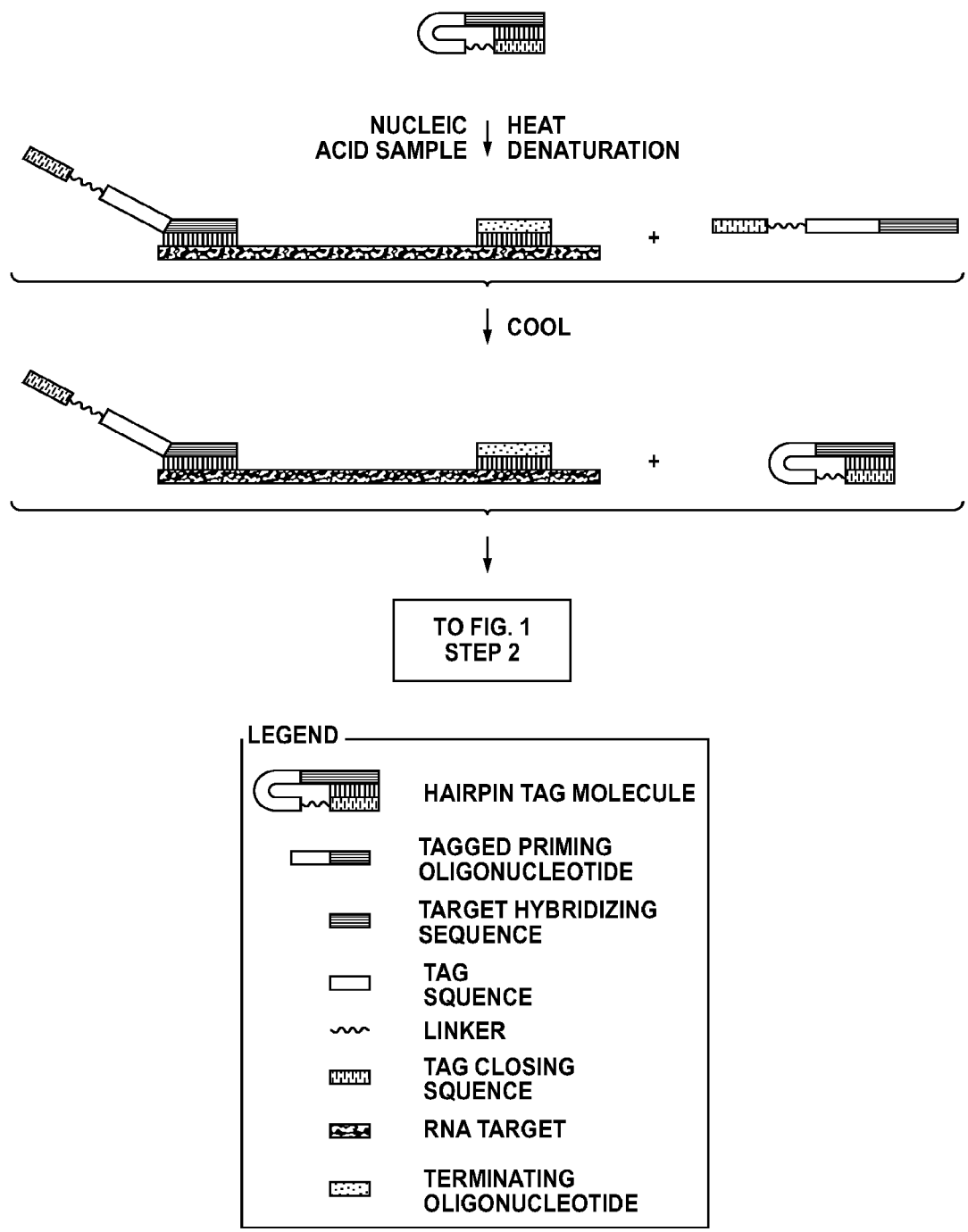

In accordance with the present invention, compositions, kits and methods are provided for the selective hybridization and capture of a target nucleic acid, wherein these compositions, kits and methods desirably reduce or eliminate the hybridization and capture of non-target nucleic acids and/or contaminating nucleic acids. Selectively hybridized and captured target nucleic acids are then used in any of a variety of downstream applications. One such downstream application is a nucleic acid amplification and detection assay. Using the compositions and methods for selective target hybridization and capture of a target nucleic acid followed by an amplification reaction, the false positive amplification signals resulting from contaminating biological material that may be present in a reagent or component of an amplification reaction are substantially reduced or eliminated compared to assays that do not use the invention compositions and methods. The provided compositions and methods also allow for less stringent purification and/or sterility efforts than have been conventionally needed in order to ensure that enzymes and other reagents or components used in amplification reactions, and the environment in which amplification reactions or other analyses are performed, are free of contamination by microorganisms or components thereof, that may yield false positive results.

The practice of the present invention will employ, unless otherwise indicated, conventional techniques of molecular biology, recombinant DNA, and chemistry, which are within the skill of the art. Such techniques are explained fully in the literature. See, e.g., Molecular Cloning A Laboratory Manual, 2nd Ed., Sambrook et al., ed., Cold Spring Harbor Laboratory Press: (1989); DNA Cloning, Volumes I and II (D. N. Glover ed., 1985); Oligonucleotide Synthesis (M. J. Gait ed., 1984); Mullis et al., U.S. Pat. No. 4,683,195; Nucleic Acid Hybridization (B. D. Hames & S. J. Higgins eds. 1984); B. Perbal, A Practical Guide To Molecular Cloning (1984); the treatise, Methods In Enzymology (Academic Press, Inc., N.Y.); and in Ausubel et al., Current Protocols in Molecular Biology, John Wiley and Sons, Baltimore, Md. (1989).

Definitions:

The following terms have the following meanings unless expressly stated to the contrary. It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

The term "nucleic acid" is intended to encompass a singular "nucleic acid" as well as plural "nucleic acids," and refers to any chain of two or more nucleotides, nucleosides, or nucleobases (e.g., deoxyribonucleotides or ribonucleotides) covalently bonded together. Nucleic acids include, but are not limited to, viral genomes, or portions thereof, either DNA or RNA, bacterial genomes, or portions thereof, fungal, plant or animal genomes, or portions thereof, messenger RNA (mRNA), ribosomal RNA (rRNA), transfer RNA (tRNA), plasmid DNA, mitochondrial DNA, or synthetic DNA or RNA. A nucleic acid may be provided in a linear (e.g., mRNA), circular (e.g., plasmid), or branched form, as well as a double-stranded or single-stranded form. Nucleic acids may include modified bases to alter the function or behavior of the nucleic acid, e.g., addition of a 3'-terminal dideoxynucleotide to block additional nucleotides from being added to the nucleic acid. As used herein, a "sequence" of a nucleic acid refers to the sequence of bases that make up a nucleic acid. The term "polynucleotide" may be used herein to denote a nucleic acid chain. Throughout this application, nucleic acids are designated as having a 5'-terminus and a 3'-terminus. Standard nucleic acids, e.g., DNA and RNA, are typically synthesized "3'-to-5'," i.e., by the addition of nucleotides to the 5'-terminus of a growing nucleic acid.

A "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" is a unit that does not significantly participate in hybridization of a polymer. Such units must not, for example, participate in any significant hydrogen bonding with a nucleotide, and would exclude units having as a component one of the five nucleotide bases or analogs thereof.

A "target nucleic acid" is a nucleic acid present in a nucleic acid sample comprising a "target sequence" to be selectively hybridized by an inactivatable target capture oligomer of the current invention. Target nucleic acids may be DNA or RNA as described herein, and may be either single-stranded or double-stranded. The target nucleic acid may include other sequences besides the target sequence. Typical target nucleic acids include viral genomes, bacterial genomes, fungal genomes, plant genomes, animal genomes, rRNA, tRNA, or mRNA from viruses, bacteria or eukaryotic cells, mitochondrial DNA, or chromosomal DNA.

Target nucleic acids may be from any number of sources. Sources of target nucleic acids include, but are not limited to, clinical specimens (e.g., blood, either whole blood or platelets, urine, saliva, feces, semen, or spinal fluid), environmental samples (e.g., water or soil samples), food samples, beverages, industrial samples (e.g., products and process materials, including water), seed stocks, cDNA libraries, whole cell lysates or total cellular RNA. By "isolated" it is meant that a sample containing a target nucleic acid is taken from its natural milieu; however, the term does not connote any particular degree of purification. If necessary, target nucleic acids of the present invention are made available for interaction with the various oligonucleotides of the present invention, using methodologies such as, cell lysis or cell permeabilization to release the target nucleic acid from cells. Nucleic acids comprising a mixture of target nucleic acids and non-target nucleic acids are then released. See, e.g., Clark et al., U.S. Pat. No. 5,786,208; and Hogan, U.S. Pat. No. 6,821,770.

The term "target sequence" refers to the particular nucleotide sequence of the target nucleic acid that is to be hybridized by a target hybridizing region. Further, "target sequence" can also include particular nucleotide sequence of the target nucleic acid that is to be amplified in a subsequent amplification reaction. Where the target nucleic acid is originally single-stranded, the term "target sequence" will also refer to the sequence complementary to the "target sequence" as present in the target nucleic acid. Where the "target nucleic acid" is originally double-stranded, the term "target sequence" refers to both the sense (+) and antisense (−) strands. In choosing a target sequence, the skilled artisan will understand that a sequence should be chosen so as to distinguish between unrelated or closely related target nucleic acids. As will be understood by those of ordinary skill in the art, these sequences are judged from the testing environment. At least the sequences recognized by the target hybridizing sequence of an inactivatable target capture oligomer should be dissimilar to other sequences in the environment being tested, but need not be unique within the universe of all possible sequences. Furthermore, it is not always the case that the unique sequence is in a single type of target nucleic acid. What this means is that in some embodiments, it may be desirable to choose a target sequence that is common to a class of organisms, for example, a target nucleic acid sequence common to all *E. coli* strains that might be in a sample. In other situations, a very highly specific target sequence, or a target sequence having at least a highly specific region recognized by the detection probe, would be chosen so as to distinguish between closely related organisms, for example, between pathogenic and non-pathogenic *E. coli*. In these instances, the target sequence for these plurality of target nucleic acids should be unique amongst other sequences in the mixture, but are sufficiently identical amongst themselves to stably hybridize to a common target hybridizing region. A target sequence of the present invention may be of any practical length. A minimal target sequence includes a region that hybridizes to a target hybridizing sequence and the complement thereof. Other considerations for determining length of a target sequence are, for example, the amount of secondary structure, or self-hybridizing regions in the sequence. Those of ordinary skill in the art using routine optimization methods easily accomplish determining the optimal length. Typically, target sequences of the present invention range from about 10 nucleotides in length, to about 100 nucleotides in length to from about 150 to about 250 nucleotides in length. The optimal or preferred length may vary under different conditions, which can easily be tested by one of ordinary skill in the art according to the methods described herein.

The terms "amplicon" and "amplification product" refer to a nucleic acid molecule generated during an amplification procedure that is substantially complementary or identical to a sequence contained within the target nucleic acid.

As used herein, the term "oligonucleotide" or "oligo" or "oligomer" is intended to encompass a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof. The term oligonucleotide does not denote any particular function to the reagent; rather, it is used generically to cover all such reagents described herein. An oligonucleotide may serve various different functions, e.g., target capture oligomers hybridize to target nucleic acids for capture and isolation of nucleic acids; amplification oligomer include heterologous amplification oligomers, primer oligomers and promoter-based amplification oligomers; primer oligomers hybridize to complementary strands and are then extended in the presence of a nucleic acid polymerase; alternatively, primers further a promoter sequence recognized by an RNA polymerase that allows for transcription, and oligomers may function to prevent hybridization or impede primer extension if appropriately situated and/or modified. Specific oligonucleotides of the present invention are described herein. As used herein, an oligonucleotide can be virtually any length, limited only by its specific function in the amplification reaction or in detecting an amplification product of the amplification reaction.

Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. As intended by this disclosure, an oligonucleotide does not consist solely of wild-type chromosomal DNA or the in vivo transcription products thereof.

Oligonucleotides may be modified in any way, as long as a given modification is compatible with the desired function of a given oligonucleotide. One of ordinary skill in the art can easily determine whether a given modification is suitable or desired for any given oligonucleotide of the present invention. Modifications include base modifications, sugar modifications or backbone modifications. Base modifications include, but are not limited to the use of the following bases in addition to adenine, cytidine, guanosine, thymine and uracil: C-5 propyne, 2-amino adenine, 5-methyl cytidine, inosine, and dP and dK bases. The sugar groups of the nucleoside subunits may be ribose, deoxyribose and analogs thereof, including, for example, ribonucleosides having a 2'-O-methyl (2'-O-Me) substitution to the ribofuranosyl moiety. See Becker et al., U.S. Pat. No. 6,130,038. Other sugar modifications include, but are not limited to 2'-amino, 2'-fluoro, (L)-alpha-threofuranosyl, and pentopuranosyl modifications. The nucleoside subunits may by joined by linkages such as phosphodiester linkages, modified linkages or by non-nucleotide moieties that do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone that couples the nucleobase subunits by means of a carboxymethyl linker to the central secondary amine (DNA analogs having a pseudo peptide backbone are commonly referred to as "peptide nucleic acids" or "PNA" and are disclosed by Nielsen et al., "Peptide Nucleic Acids," U.S. Pat. No. 5,539,082.) Other linkage modifications include, but are not limited to, morpholino bonds.

Non-limiting examples of oligonucleotides or oligomers contemplated by the present invention include nucleic acid analogs containing bicyclic and tricyclic nucleoside and nucleotide analogs (LNAs). See Imanishi et al., U.S. Pat. No. 6,268,490; and Wengel et al., U.S. Pat. No. 6,670,461.) Any nucleic acid analog is contemplated by the present invention provided the modified oligonucleotide can perform its intended function, e.g., hybridize to a target nucleic acid under stringent hybridization conditions, self-hybridize under appropriate conditions to form a hairpin structure, synthesize complementary nucleic acids strands if a target nucleic acid sequence under amplification conditions, or interact with a DNA or RNA polymerase, thereby initiating extension or transcription.

While design and sequence of oligonucleotides for the present invention depend on their function as described below, several variables must generally be taken into account. Among the most critical are: length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well-known aspect of oligonucleotide design, and various computer programs are readily available to screen large numbers of potential oligonucleotides for optimal ones.

The 3'-terminus of an oligonucleotide (or other nucleic acid) can be blocked in a variety of ways using a blocking moiety, as described below. A "blocked" oligonucleotide is not efficiently extended by the addition of nucleotides to its 3'-terminus, by a DNA- or RNA-dependent DNA polymerase, to produce a complementary strand of DNA. As such, a "blocked" oligonucleotide cannot be considered a primer.

As used in this disclosure, the phrase "an oligonucleotide having a nucleic acid sequence 'comprising,' 'consisting of,' or 'consisting essentially of' a sequence selected from" a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

The phrase "an oligonucleotide substantially corresponding to a nucleic acid sequence" means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions.

One skilled in the art will understand that "substantially corresponding" oligonucleotides can vary from the referred to sequence and still hybridize to the same target nucleic acid sequence. Variations can be in the form of one or more nucleotide deletions, additions, substitutions or modifications in the oligomer sequence compared to that oligomers intended target sequence. This variation from the nucleic acid may be stated in terms of a percentage of identical bases within the sequence or the percentage of perfectly complementary bases between oligomer and its target sequence. Thus, an oligonucleotide of the present invention substantially corresponds to a reference nucleic acid sequence if these percentages of base identity or complementarity are from 100% to about 80%. In preferred embodiments, the percentage is from 100% to about 85%. In more preferred embodiments, this percentage can be from 100% to about 90%; in other preferred embodiments, this percentage is from 100% to about 95%. One skilled in the art will understand the various modifications to the hybridization conditions that might be required at various percentages of complementarity to allow hybridization to a specific target sequence without causing an unacceptable level of non-specific hybridization.

The "tag-closing sequence" present in the inactivatable target capture oligomer may be essentially any heterologous sequence provided that it does not stably hybridize to the target nucleic acid sequence of interest and, thereby, participate in selective hybridization and capture. The tag-closing sequence preferably does not stably hybridize to any sequence derived from the genome of an organism being tested or, more particularly, to any target nucleic acid under reaction conditions. A tag-closing sequence that is present in a inactivatable target capture oligonucleotide is preferably designed so as not to substantially impair or interfere with the ability of the target hybridizing sequence to hybridize to its target sequence. Moreover, in certain alternative embodiments wherein the tag-closing sequence is also a tag sequence it is of sufficient length and composition such that once the tag sequence or a complement thereof has been incorporated into an initial DNA primer extension product, a tag-specific priming oligonucleotide can then be used to participate in subsequent rounds of amplification as described herein. A tag-closing sequence of the present invention is typically at least 3 nucleotides in length, and may extend up to 6, 10, 15, 20, 25, 30, 35, 40, 50 or more nucleotides in length. Skilled artisans will recognize that the design of tag-closing sequences and, optionally, tag sequences for use in the present invention can follow any of a number of suitable strategies, while still achieving the objectives and advantages described herein.

The term "inactivating" means that a target hybridizing region is altered so that it will not stably bind to a target nucleic acid sequence under target hybridization conditions. Thus, under a first set of conditions, an inactivatable target capture oligomer, and, optionally, a heterologous amplification oligomer will hybridize to target nucleic acids present in the sample. Unhybridized inactivatable target capture oligomer are inactivated under a second set of conditions in which the inactivatable target capture oligomer is configured to self-hybridize into an inactive and preferably hairpin configuration. The target hybridizing regions are then sterically blocked, which prevents or substantially reduces binding of inactivated inactivatable target capture oligomers to non-target nucleic acids and/or contaminating nucleic acids. So, "inactivating" means that the inactivatable target capture oligomer is altered from an "active" confirmation which permits the target hybridizing sequence to hybridize to the target nucleic acid sequence to an "inactive" confirmation which blocks or otherwise prevents the target hybridizing sequence from hybridizing to the target nucleic acid sequence. As example only, an inactive confirmation may be formed under stringency conditions permitting the tag-closing sequence to form a stable hybrid with the target hybridizing sequence (e.g., under less stringent conditions than the conditions for forming an active confirmation of the inactivatable target capture oligonucleotide). Alternatively, a duplex formed between the tag-closing sequence and the target hybridizing sequence may be altered by an enzyme, such as a DNAse, an S1 nuclease, an endonuclease, such as a restriction enzyme which cleaves a double-stranded restriction site formed between the tag-closing sequence and the target hybridizing sequence, a ribonuclease activity (e.g., RNAse H activity) for digesting the RNA component (e.g., target hybridizing sequence) of a DNA:RNA hybrid, or an exonuclease having a 3'-to-5' or 5'-to-3' activity for removing nucleotides from the target hybridizing sequence hybridized to the tag-closing sequence. However, to avoid exposing a sample to a potentially contaminating source of the target nucleic acid sequence, the use of enzymes to inactivate inactivatable target capture oligonucleotides that have not hybridized to the target nucleic acid sequence is generally not preferred. Other inactivating means include chemicals for altering the target hybridizing sequence so that it is incapable of hybridizing to a target nucleic acid sequence under amplification conditions. Preferably, but not necessarily, a target hybridizing region of an inactivatable target capture oligomer is 15, 16, 17, 18, 19, 20, 21, 22, 23, 24, 25, 26, 27, 28, 29 or 30 nucleobases in length. Preferably, but not necessarily, a tag-closing region of an inactivatable target capture oligomer is 3, 4, 5, 6, 7, 8, 9, 10, 11, 12, 13, 14, 15, 16, 17, 18, 19 or 20 nucleobases in length. Some exemplary and non-limiting embodiments of inactivatable target capture oligomers in the current disclosure comprise target hybridizing regions that are 17 nucleobases in length, and comprise tag-closing regions that are 6, 7, 8, 9, 10, 12 and 14 nucleobases in length. In these embodiments, the binding pair members are substantially homopolymeric nucleotide sequences of 33 nucleobases in length. These are non-limiting embodiments provided for example of the current invention.

Moieties can be included in the tag hybridizing sequence to further stabilize hybrids formed between the tag-closing sequence and the target hybridizing sequence of inactivatable target capture oligomers, especially where it is anticipated that at least some of the inactive inactivatable target capture oligomer will be introduced into the amplification reaction mixture. Suitable moieties include modified nucleotides, including LNAs, 2'-O-Me ribonucleotides, 2,6 diamino purine. 5-methyl cytosine, and C-5 propynyl cytosine or uracil. Those skilled in the art will be able to readily select the number and positions of such modified nucleotides to limit breathing at the 5'- and 3'-ends of the tag-closing sequence and to achieve a desired melting temperature of the hybrid without engaging in undue experimentation. Other suitable moieties include minor groove binders and pendant groups, such as purine, DABCYL, pyrine and 5'-trimethoxy stilbene CAP.

As used herein, the term "removing" refers to the physical separation of captured target nucleic acid sequences from unhybridized inactivatable target capture oligomer. Captured target nucleic acid sequences can be physically separated from unhybridized inactivatable target capture oligomer present in a nucleic acid sample by a variety of techniques known to those skilled in the art. By way of example, captured target nucleic acid sequences can be bound to a solid support and immobilized in a nucleic acid sample while unbound material is removed. To remove unbound material, the solid support can be subjected to one or more wash/rinse steps. A rinse step is typically included where the wash solution contains a component that is inhibitory to subsequent analysis of the target nucleic acids when present at a sufficiently high concentration, such as a detergent. The solid support preferably binds specifically to captured target nucleic acids, to prevent unhybridized inactivatable target capture oligomer from entering into the amplification reaction. Exemplary means for capturing, immobilizing and purifying target nucleic acids are discussed below, an example of which is disclosed by Weisburg et al., U.S. Pat. No. 6,534,273.

Figure 11:
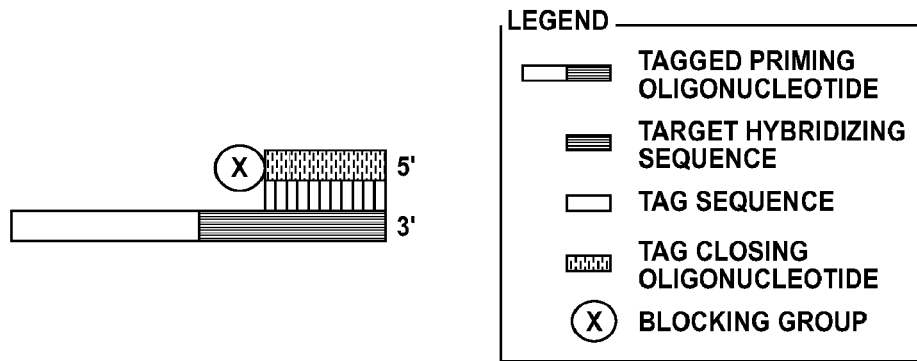
Figure 12:
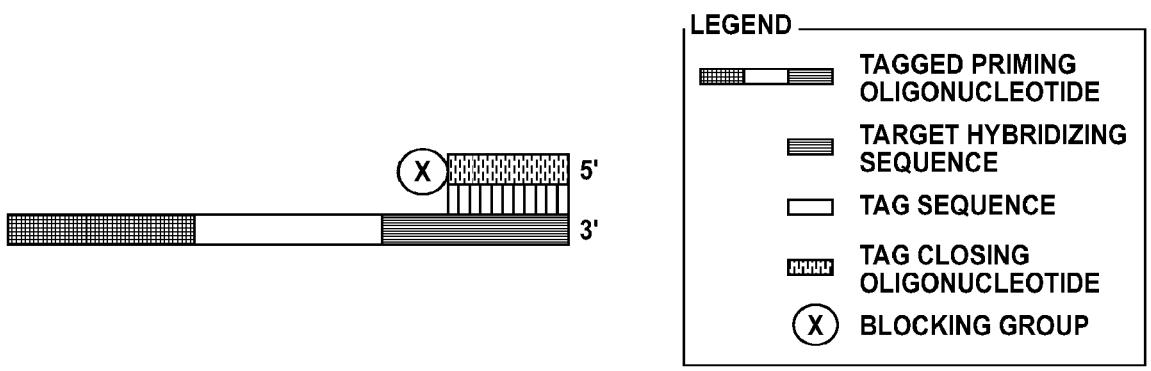
Figure 13:
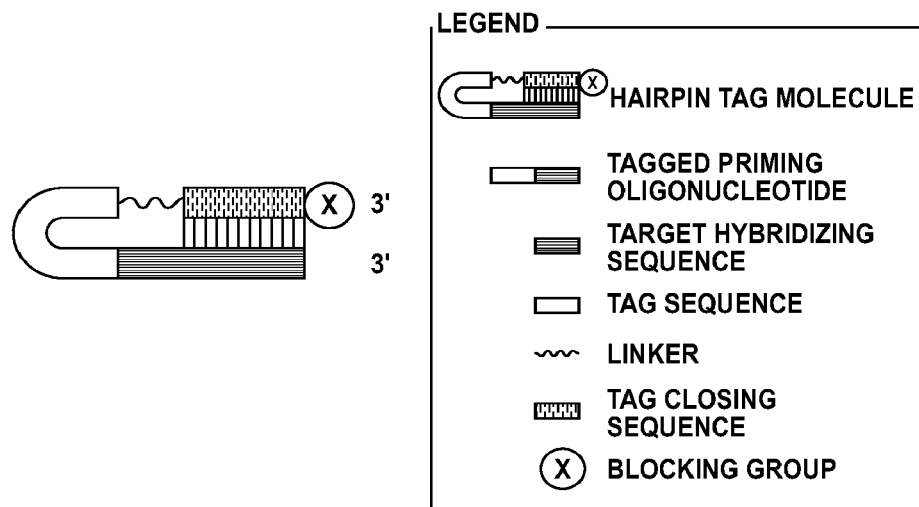
Figure 14:
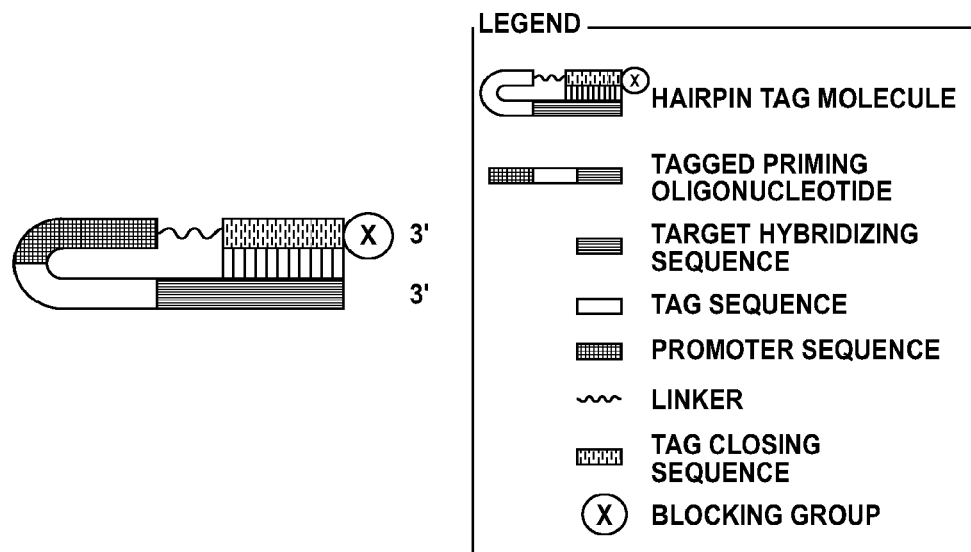
Figure 15:
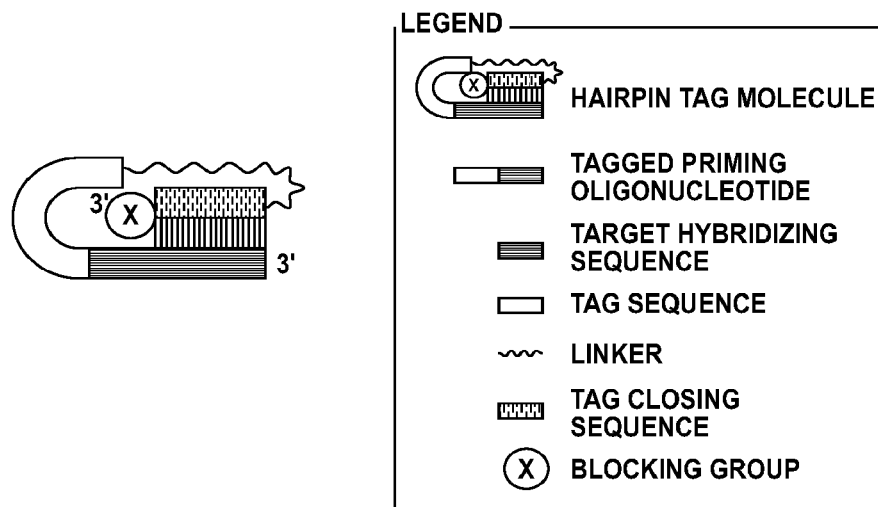
Figure 16:
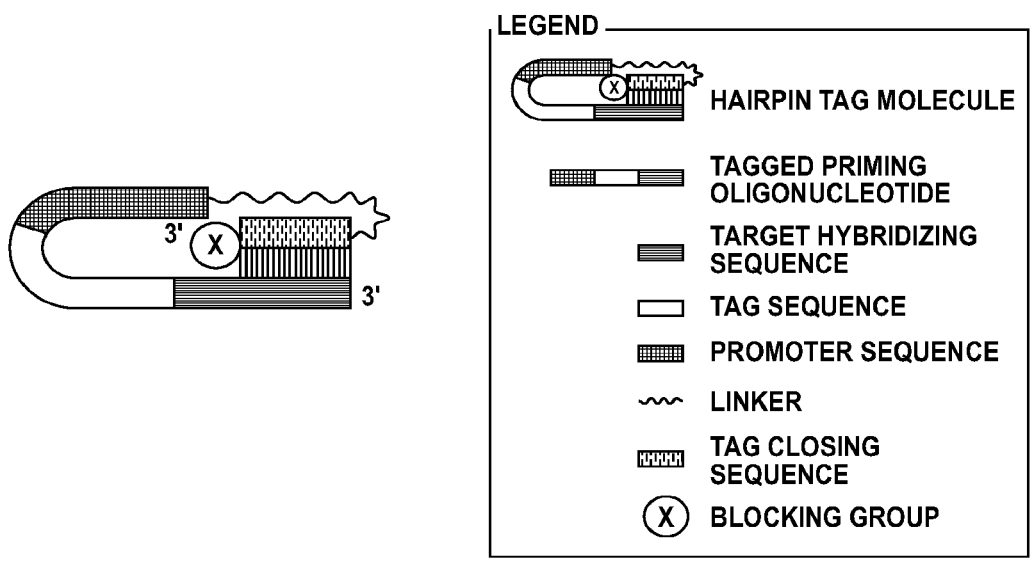
Figure 22:
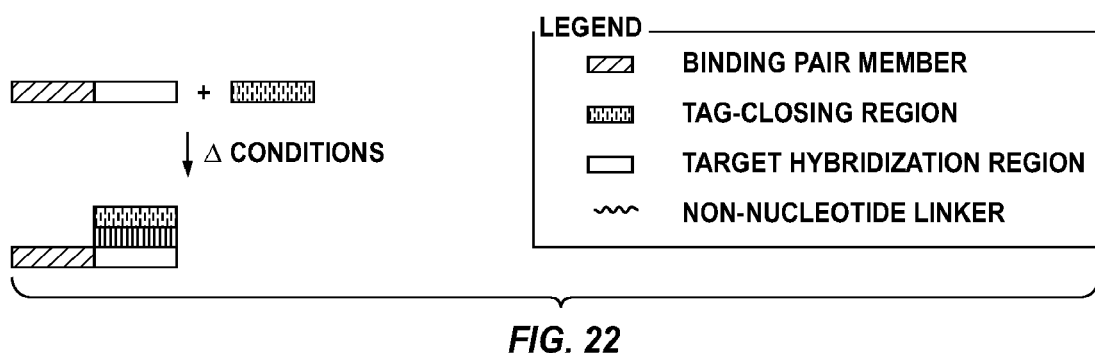
FIGS. 22 through 25 illustrate some configurations of the inactivatable target capture oligomer of the current invention, in representative active and in inactive configurations.

The phrases "tag-closing sequence," "tag closing region" and "tag-closing oligonucleotide" refer to a nucleotide sequence that is complementary to a portion of the target hybridizing sequence of an inactivatable target capture oligomer. The length and sequence of the tag-closing sequence are selected so that the tag-closing sequence does not stably hybridize to the target hybridizing sequence of the inactivatable target capture oligomer under a first set of conditions permitting stable hybridization of the target hybridizing sequence to a target sequence. The tag-closing sequence may include abasic nucleotides or base mismatches with the target hybridizing sequence. Provided the inactivatable target capture oligomer is not hybridized to the target sequence, the tag-closing sequence stably hybridizes to the target hybridizing sequence under a second set of less stringent conditions, thus "inactivating" or blocking the inactivatable target capture oligomer from hybridizing to the target sequence. The tag-closing sequence may be in the form of a discrete oligonucleotide, as exemplified in FIGS. 11, 12 & 22, or it may be an integral part of the inactivatable oligomer, so that it forms a hairpin structure under the second set of conditions, as exemplified in FIGS. 13, 14 & 23-27. If the tag-closing sequence is joined to the inactivatable oligonucleotide via a non-nucleotide linker region (e.g., abasic nucleotides or polyethylene glycol), then the non-nucleotide linker is of sufficient length for the tag-closing sequence to hybridize to the target hybridizing sequence under the second set of conditions. The association kinetics are best when the tag-closing sequence and the target hybridizing sequence of the tagged oligonucleotide are contained in the same molecule (integral configuration). Under selective conditions, the tag-closing sequence can hybridize to a target hybridizing sequence in an antiparallel orientation, as shown in FIGS. 2, 4, 6, 8, 10, 11, 12, 15 and 16, or in a parallel orientation, as shown in FIGS. 13 and 14. If the tag-closing sequence is a discrete molecule, as illustrated in FIGS. 11, 12 and 22, or joined to the tagged oligonucleotide by a non-nucleotide linker, as illustrated in FIGS. 2, 4, 6, 8, 10, 15, 16 and 23, then the tag-closing sequence is preferably modified to prevent primer extension by a DNA polymerase, such as by positioning a blocking moiety at its 3'-terminus. Suitable blocking moieties are described herein. When hybridized in an antiparallel orientation, as illustrated in FIGS. 13 and 14, the 3'-terminal base of the tag-closing sequence is preferably hybridized to the 3'-terminal base of the target hybridizing sequence. More preferably, the tag-closing sequence is modified to prevent primer extension by a DNA polymerase. The tag-closing sequence may be modified to prevent the initiation of DNA synthesis therefrom, which can include a blocking moiety situated at its 3'-terminus. The tag-closing sequence is at least 3 nucleobases in length. Typical tag-closing sequences are preferably from 6 to 16 bases in length.

Figure 23:
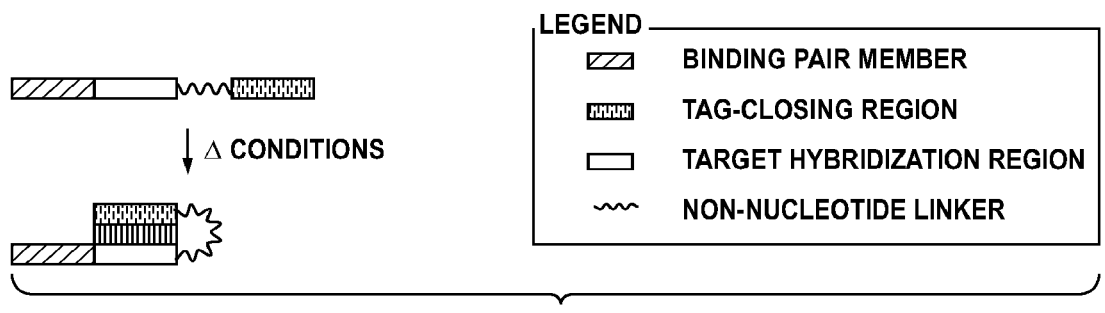
Figure 24:
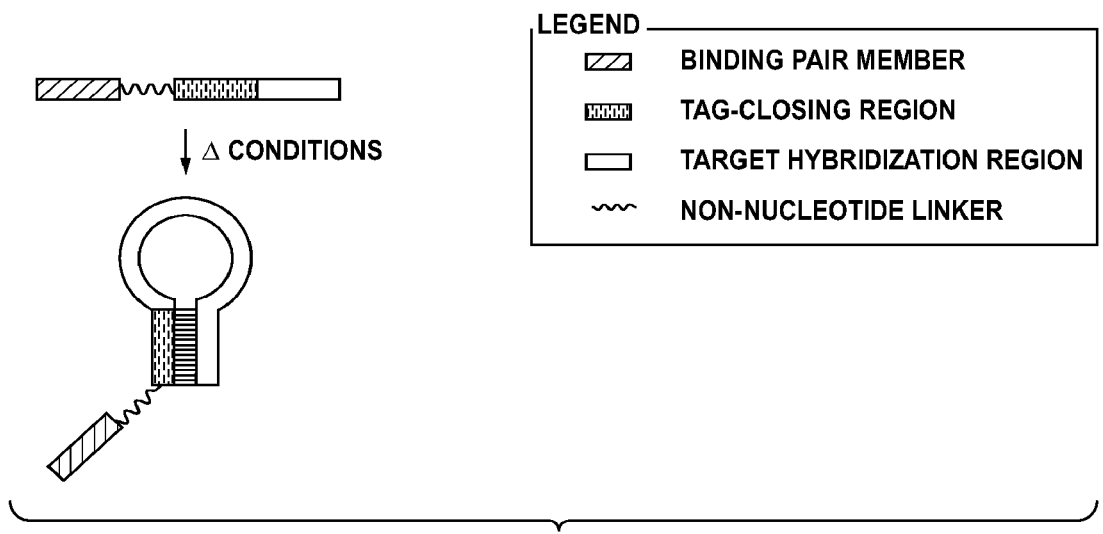
Figure 25:
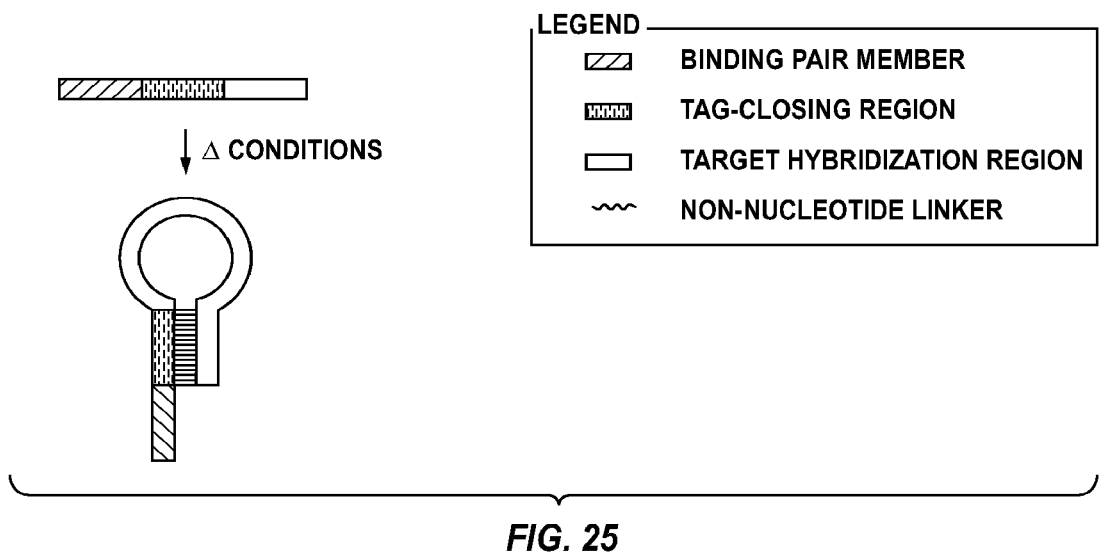

FIG. 22 shows a tag-closing sequence that is a discrete molecule, while FIGS. 23, 24 and 25 show a capture probe molecule that incorporates the tag-closing sequence as an integral part of the target capture oligomer. This figure illustrates for all embodiments that the discrete tag-closing region is capable of stable hybridization to the target hybridizing sequence under conditions of reduced stringency. FIGS. 24 and 25 illustrate a tag-closing sequence that is directly joined to the target hybridizing sequence. FIG. 23 illustrates a tag-closing sequence that is indirectly joined to the target hybridizing sequence (e.g., nucleotide sequence or non-nucleotide linker). In general, a preferred tag-closing sequence hybridizes to 5 to 20 contiguous or non-contiguous bases of the target hybridizing sequence and is from 5 to 20 bases in length. Preferably, any terminal 3'-ends that can be used for a primer-based amplification are blocked to prevent such an extension reaction.

By "amplification" or "nucleic acid amplification" is meant production of multiple copies of a target nucleic acid that contains at least a portion of the intended specific target nucleic acid sequence. The multiple copies may be referred to as amplicons or amplification products. In certain embodiments, the amplified target contains less than the complete target gene sequence (introns and exons) or an expressed target gene sequence (spliced transcript of exons and flanking untranslated sequences). For example, specific amplicons may be produced by amplifying a portion of the target polynucleotide by using amplification primers that hybridize to, and initiate polymerization from, internal positions of the target polynucleotide. Preferably, the amplified portion contains a detectable target sequence that may be detected using any of a variety of well-known methods.

Many well-known methods of nucleic acid amplification require thermalcycling to alternately denature double-stranded nucleic acids and hybridize primers; however, other well-known methods of nucleic acid amplification are isothermal. PCR and RT-PCR are thermalcycling techniques that use multiple cycles of denaturation, annealing of primer pairs to opposite strands, and primer extension to exponentially increase copy numbers of the target sequence. Variations of the PCR technique include SDA and tSDA. Isothermal techniques include, but are not limited to, NASBA, Q.beta. replicase and transcription-based amplification methods like self-sustained sequence replication and TMA. Other illustrative amplification methods suitable for use in accordance with the present invention include, but are not limited to, RCA, had, and LAMP.

TMA employs an RNA polymerase to produce multiple RNA transcripts of a target region (e.g., Kacian et al., U.S. Pat. Nos. 5,480,784 and 5,399,491; and Becker et al., U.S. Pub. No. US 2006-0046265 A1). TMA uses at least one "promoter oligonucleotide" or "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNAse H activity to digest the RNA strand of an RNA:DNA hybrid, thereby making the DNA strand available for hybridization with a primer or promoter-primer. Generally, the RNAse H activity associated with the reverse transcriptase provided for amplification is used.

In one illustrative TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a sub-population of such promoter-primers, may be modified to block or reduce primer extension. From an unmodified promoter-primer, reverse transcriptase creates a cDNA copy of the target RNA, while RNAse H activity degrades the target RNA. A second amplification primer then binds to the cDNA. This primer may be referred to as a "non-T7 primer" to distinguish it from a "T7-primer". From this second amplification primer, reverse transcriptase creates another DNA strand, resulting in a double-stranded DNA with a functional promoter at one end. When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly synthesized amplicon can anneal with the second amplification primer. Reverse transcriptase can then create a DNA copy, while the RNAse H activity degrades the RNA of this RNA:DNA duplex. The promoter-primer can then bind to the newly synthesized DNA, allowing the reverse transcriptase to create a double-stranded DNA, from which the RNA polymerase produces multiple amplicons. Thus, a billion-fold isothermic amplification can be achieved using two amplification primers.

In another illustrative TMA method, one or more features as described in Becker et al., U.S. Pub. No. US 2006-0046265 are optionally incorporated. Preferred TMA methods in this respect include the use of blocking moieties, terminating moieties, and other modifying moieties that provide improved TMA process sensitivity and accuracy. Thus, certain preferred embodiments of the present invention employ inactivatable oligonucleotides, as described herein, in conjunction with the methods as described in Becker et al., U.S. Pub. No. US 2006-0046265.

By "detectable amplification" is meant that a detectable signal associated with an amplification product in an amplification reaction mixture rises above a predetermined background or threshold level (end-point amplification) or rises above a background or threshold level within a predetermined period of time (real-time amplification). See, e.g., Light et al., U.S. Pub. No. US 2006-0276972, paragraphs 506-549. The amplification product contains a sequence having sequence identity with a target nucleic acid sequence or its complement and can be detected with, for example, an intercalating dye or a detection probe having specificity for a region of the target nucleic acid sequence or its complement.

An amplification product can be detected by any conventional means. For example, amplification product can be detected by hybridization with a detectably labeled probe and measurement of the resulting hybrids. Design criteria in selecting probes for detecting particular target sequences are well known in the art and are described in, for example, Hogan et al., U.S. Pat. No. 6,150,517. Amplification products can be assayed by the Hybridization Protection Assay ("HPA"), which involves hybridizing a chemiluminescent oligonucleotide probe to the target sequence, e.g., an acridinium ester-labeled ("AE") probe, selectively hydrolyzing the chemiluminescent label present on unhybridized probe, and measuring the chemiluminescence produced from the remaining probe in a luminometer. See, e.g., Arnold et al., U.S. Pat. No. 5,283,174 and Nelson et al., Nonisotopic Probing, Blotting and Sequencing, ch. 17 (Larry J. Kricka ed., 2d ed. 1995).

Further embodiments provide quantitative evaluation of the amplification process in real-time by methods described herein. Evaluation of an amplification process in "real-time" involves determining the amount of amplicon in the reaction mixture either continuously or periodically during the amplification reaction, and the determined values are used to calculate the amount of target sequence initially present in the sample. There are a variety of methods for determining the amount of initial target sequence present in a sample based on real-time amplification. These include those disclosed by Wittwer et al., U.S. Pat. No. 6,303,305, and Yokoyama et al., U.S. Pat. No. 6,541,205. Another method for determining the quantity of target sequence initially present in a sample, but which is not based on a real-time amplification, is disclosed by Ryder et al., U.S. Pat. No. 5,710,029.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of example, "molecular torches" are a type of self-hybridizing probe that includes distinct regions of self-complementarity (referred to as "the target binding domain" and "the target closing domain"), which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification product under strand displacement conditions. Under strand displacement conditions, hybridization of the two complementary regions (which may be fully or partially complementary) of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed by Becker et al., U.S. Pat. No. 6,534,274.

Another example of a detection probe having self-complementarity is a "molecular beacon." Molecular beacons include nucleic acid molecules having a target complement sequence, an affinity pair (or nucleic acid arms) holding the probe in a closed conformation in the absence of a target sequence present in an amplification product, and a label pair that interacts when the probe is in a closed conformation. Hybridization of the target sequence and the target complement sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed by Tyagi et al., U.S. Pat. Nos. 5,925,517, and 6,150,097.

Other self-hybridizing probes for use in the present invention are well known to those of ordinary skill in the art. By way of example, probe binding pairs having interacting labels, such as those disclosed by Morrison, U.S. Pat. No. 5,928,862 and Gelfand et al., U.S. Pat. No. 5,804,375, might be adapted for use in the present invention. Additional detection systems include "molecular switches," Arnold et al., U.S. Pub. No. U.S. 2005-0042638 A1. And other probes, such as those comprising intercalating dyes and/or fluorochromes, might be useful for detection of amplification products in the present invention. See, e.g., Ishiguro et al., U.S. Pat. No. 5,814,447.

In amplification and detection methods where the initial target sequence and the RNA transcription product share the same sense, it may be desirable to initiate amplification before adding probe for real-time detection. Adding probe prior to initiating an amplification reaction may slow the rate of amplification since probe which binds to the initial target sequence has to be displaced or otherwise remove during the primer extension step to complete a primer extension product having the complement of the target sequence. The initiation of amplification is judged by the addition of amplification enzymes (e.g., a reverse transcriptase and an RNA polymerase).

"Selective amplification" as used herein, refers to the amplification of a target nucleic acid sequence that has been selectively hybridized and captured using compositions and methods according to the present invention, and where detectable amplification is limited or substantially limited to amplification of target sequence and is not contributed by non-target nucleic acid sequence and/or contaminant nucleic acid. As used herein, a "non-target nucleic acid" is a nucleic acid that is present in a reaction mixture but is not the desired nucleic acid. Non-target nucleic acids include, but are not limited to, nucleic acids present in a whole-cell lysate other than the nucleic acid of interest. For example, if the target nucleic acids is a micro RNA known or thought to be present in a cell sample, the remaining nucleic acid present in that sample (or lysate thereof) are the non-target nucleic acids. Here, the inactivatable target capture oligomer is configured to comprise a target hybridizing region substantially complementary to this small target nucleic acid. It is desirous that the inactivatable target capture oligomer does not hybridize any non-target nucleic acid, which are hindrances to downstream analysis of the desired target nucleic acids. Thus, an active form of the invention inactivatable target capture oligomer is allowed to hybridize the target nucleic acid under a first set of conditions biasing the capture oligomer to the target, and then the inactivatable target capture oligomer is made inactive to prevent binding to non-target nucleic acids. As is used herein, a "contaminant nucleic acid" is a nucleic acid that is introduced into a system from an outside source. Such sources include, but are not limited to, reagent preparations, labwares, lab personnel and laboratory workspace.

By "amplification conditions" is meant conditions permitting nucleic acid amplification. Amplification conditions may, in some embodiments, be less stringent than "stringent hybridization conditions" as described herein. Oligonucleotides used in amplification reactions hybridize to their intended targets under amplification conditions, but may or may not hybridize under stringent hybridization conditions. On the other hand, detection probes are typically designed to hybridize under stringent hybridization conditions. While the Examples section infra provides preferred amplification conditions for amplifying target nucleic acid sequences, other acceptable conditions to carry out nucleic acid amplifications could be easily ascertained by someone having ordinary skill in the art depending on the particular method of amplification employed.

Nucleic acid hybridization is the process by which two nucleic acid strands having completely or partially complementary nucleotide sequences come together under predetermined reaction conditions to form a stable, double-stranded hybrid. Either nucleic acid strand may be a deoxyribonucleic acid (DNA) or a ribonucleic acid (RNA) or analogs thereof. Thus, hybridization can involve RNA:RNA hybrids, DNA:DNA hybrids, RNA:DNA hybrids, or analogs thereof. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases that are not members of these "canonical" pairs. Non-canonical base pairing is well known in the art. (See, e.g., Adams, et al., The Biochemistry of the Nucleic Acids, (11th ed. 1992).)

"Hybridization conditions" refer to the cumulative physical and chemical conditions under which nucleic acid sequences that are completely or partially complementary form a hybridization duplex or complex. Such conditions are well known to those skilled in the art, are predictable based on sequence composition of the nucleic acids involved in hybridization, or may be determined empirically by using routine testing (e.g., Sambrook et al., Molecular Cloning, A Laboratory Manual, 2nd ed. (Cold Spring Harbor Laboratory Press, Cold Spring Harbor, N.Y., 1989) at §§ 1.90-1.91, 7.37-7.57, 9.47-9.51, 11.12-11.13, and 11.45-11.57).

"Stringent hybridization conditions" or "stringent conditions" refer to conditions where a specific nucleic acid strand (including, but not limited to, an inactivatable target capture oligomer) is able to preferentially hybridize with a target nucleic acid over other nucleic acids present in the test sample. It will be appreciated that these conditions may vary depending upon factors including the GC content and length of the nucleic acid sequences, the hybridization temperature, the composition of the hybridization reagent or solution, and the degree of hybridization specificity sought. Some specific stringent hybridization conditions are provided in the disclosure below.

By "nucleic acid hybrid" or "hybrid" or "duplex" is meant a nucleic acid structure containing a double-stranded, hydrogen-bonded region where each strand is complementary to the other, and where the region is sufficiently stable under stringent hybridization conditions to be detected by means including, but not limited to, chemiluminescent or fluorescent light detection, autoradiography, or gel electrophoresis.

Such hybrids may comprise RNA:RNA, RNA:DNA, or DNA:DNA duplex molecules.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable, double-stranded hydrogen-bonded region under stringent hybridization or amplification conditions. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "perfectly" complementary.

By "preferentially hybridize" is meant that under stringent hybridization conditions, certain complementary nucleotides or nucleobase sequences hybridize to form a stable hybrid preferentially over other, less stable duplexes. By "does not stably hybridize" is meant that a stable hybrid is not formed in appreciable and/or detectable amounts under a defined set of conditions. As a non-limiting example, a probe hybridizes to a target sequence or replicate thereof to a sufficiently greater extent than to a non-target sequence, thus enable one having ordinary skill in the art to accurately quantitate the RNA replicates or complementary DNA (cDNA) of the target sequence formed during the amplification. In a further non-limiting example, a target hybridization region of an inactivatable target capture oligomer hybridizes to a target nucleic acid to a sufficiently greater extent than to a non-target or contaminating nucleic acid sequence.

By "stable" or "stably hybridize" is meant that the temperature of a reaction mixture is at least 2.deg.C. below the melting temperature of a nucleic acid duplex.

The term "amplification oligomer" is used herein to refer to oligomers used as primers, promoter-based amplification oligomers such as promoter primers and promoter providers, and heterologous amplification oligomers.

A "heterologous amplification oligomer" comprises a first region that is a target hybridizing region and a second region that is a tag sequence region. The tag sequence of a heterologous amplification oligomer is configured so that under conditions wherein the target hybridizing region stably hybridizes with a target nucleic acid sequence, this tag sequence does not stably hybridize with the target nucleic acid or any known non-target or contaminating nucleic acid sequences believed to be in a sample. Following a first nucleic acid synthesis event using the heterologous amplification oligomer as a primer, the tag sequence forms an integral part of the resultant amplicon sequence and any subsequent complimentary or copy strands made thereof. Second round amplification is then performed using an amplification oligomer that targets this tag sequence, or complement thereof, thereby reducing or eliminating amplification of non-target and contaminating nucleic acids. Heterologous amplification oligomers can be promoter-based oligomers as well, wherein a third region is included; said region being an RNA polymerase promoter sequence. Such a heterologous amplification oligomer operates substantially as described directly above if the heterologous amplification oligomer is a promoter primer. In this configuration, though, an RNA copy containing the tag sequence or its complement is transcribed from a template. If, though, the heterologous amplification oligomer is a promoter provider, then an RNA molecule containing the complement of the tag sequence is first made, and subsequent amplification using the sequence or its complement takes place from there.

As is well known in the art, a "promoter" is a specific nucleic acid sequence that is recognized by a DNA-dependent RNA polymerase ("transcriptase") as a signal to bind to the nucleic acid and begin the transcription of RNA at a specific site. Efficient transcription of RNA can take place under conditions where a double-stranded promoter is not formed through an extension reaction with the template nucleic acid. The template nucleic acid (the sequence to be transcribed) need not be double-stranded. Individual DNA-dependent RNA polymerases recognize a variety of different promoter sequences, which can vary markedly in their efficiency in promoting transcription. When an RNA polymerase binds to a promoter sequence to initiate transcription, that promoter sequence is not part of the sequence transcribed. Thus, the RNA transcripts produced thereby will not include that promoter sequence.

According to the present invention, a "promoter oligonucleotide" refers to an oligonucleotide comprising first and second regions, and which is optionally modified to prevent the initiation of DNA synthesis from its 3'-terminus. The "first region" of a promoter oligonucleotide of the present invention comprises a target hybridizing region. The target hybridizing region of a promoter oligonucleotide is typically at least 10 nucleotides in length, and may extend up to 15, 20, 25, 30, 35, 40, 50 or more nucleotides in length. The "second region" comprises a promoter sequence for an RNA polymerase. A promoter oligonucleotide is sometimes engineered so that it is incapable of being extended by an RNA- or DNA-dependent DNA polymerase, e.g., reverse transcriptase, preferably comprising a blocking moiety at its 3'-terminus as described above. Suitable and preferred promoter oligonucleotides are described herein. Promoter-based amplification oligomers having a modified 3'-terminus are referred to herein as "promoter providers," while those without such a modification are referred to herein as "promoter primers." In one example, at least about 80% of the oligonucleotides present in the amplification reaction and comprising a promoter further comprise a 3'-blocking moiety. In another embodiment, at least about 85%, 90%, 95%, 96%, 97%, 98%, 99% or 100% of the oligonucleotides provided to the amplification reaction comprising a promoter are further modified to comprise a 3'-blocking moiety. In another embodiment, any oligonucleotide used in an amplification reaction that comprises a promoter sequence further comprise a 3'-terminus blocking moiety. Assaying promoter oligonucleotides with variations in the promoter sequences is easily carried out by the skilled artisan using routine methods. Furthermore, if it is desired to utilize a different RNA polymerase, then the promoter sequence in the promoter oligonucleotide is easily substituted with a different and more compatible promoter sequence. Substituting different promoter sequences is well within the understanding and capabilities of those of ordinary skill in the art.

The formation of a double-stranded promoter sequence through extension of a template nucleic acid is not necessary to permit initiation of transcription of RNA complementary to the first DNA primer extension product. The resulting "first" RNA products are substantially identical to the target sequence, having a 5'-end defined by the transcription initiation point, and a 3'-end defined by the 5'-end of the first DNA primer extension product. A sufficient number of first RNA products are produced to automatically recycle in the system without further manipulation. The priming oligonucleotide hybridizes to the 3'-end of the first RNA products, and is extended by a DNA polymerase to form a second DNA primer extension product. Unlike the first DNA primer extension product formed without the use of a terminating oligonucleotide or other binding molecule, the second DNA primer extension product has a defined 3'-end which is complementary to the 5'-ends of the first RNA products. The second DNA primer extension product is separated (at least partially) from the RNA template using an enzyme that selectively degrades the RNA template. The single-stranded second DNA primer extension product is then treated with a promoter oligonucleotide as described above, and the second region of the promoter oligonucleotide acts as a template, allowing the second DNA primer extension product to be further extended to add a base region complementary to the second region of the promoter oligonucleotide, i.e., the region comprising the promoter sequence, rendering the promoter double-stranded. An RNA polymerase that recognizes the promoter binds to the promoter sequence, and initiates transcription of multiple "second" RNA products complementary to the second DNA primer extension product, and substantially identical to the target sequence. The second RNA transcripts so produced automatically recycle in the above system without further manipulation. Thus, this reaction is autocatalytic.

"Universal" oligonucleotides or "pan" oligonucleotides include oligonucleotides that can be used in an amplification reaction to identify the presence of nucleic acid sequences of a class of organisms based upon highly conserved sequences that are unique to a class of organisms. (As used herein, the term "class" does not necessarily imply a recognized phylogenetic grouping or organisms.) For example, the highly conserved 16S ribosomal RNA-coding sequences contain regions that are found in bacteria, or groupings of bacteria (e.g., Eubacteria, Gram-positive bacteria or Gram-negative bacteria), but are not in humans and other higher organisms, and thus oligonucleotides may be designed and used in a nucleic acid amplification reaction to detect the presence of bacterial sequences in a sample of interest. See, e.g., McCabe et al. (1999) Molecular Genetics and Metabolism 66, 205-211; Schmidt, T. et al. (1994) Meth. Enzymol. 235, 205-222 (method for identifying pathogens); Kunishima, S. et al., (2000) Transfusion 40, 1420 (method for detecting bacteria in blood); Greisen, K. (1994) J. Clin. Microbiol. 32, 335-351 (method for detecting pathogenic bacteria in cerebral spinal fluid); Jordan, J. (2005) J. Mol. Diag. 7, 575-581 (method for diagnosing sepsis in neonates); Rothman, R. et al. (2002) J. Infect. Dis. 186, 1677-1681 (method for diagnosing acute bacterial endocarditis); and Cox, C. et al. (2002) Arthritis Res. Ther. 5, R1-R8 (detecting bacteria in synovial fluid). Similarly, universal oligonucleotides for other classes of organisms, such as fungal pathogens, have been described. See, e.g., Maaroati, Y. et al. (2003) J. Clin. Microbiol. 41, 3293-3298 (method for quantifying *Candida albicans* in blood); Carr, M. et al. (2005) J. Clin. Microbiol. 43, 3023-3026 (method for detecting *Candida dubliniensis* in blood); and White, P. et al. (2003) J. Med. Microbiol. 52, 229-238 (method for detecting systemic fungal infections). Essentially any universal oligonucleotides known or developed for a given class of organism may be advantageously employed in the methods described herein.

A priming oligonucleotide is an oligonucleotide, at least the 3'-end of which is complementary to a nucleic acid template, and which complexes (by hydrogen bonding or hybridization) with the template to give a primer:template complex suitable for initiation of synthesis by an RNA- or DNA-dependent DNA polymerase. A priming oligonucleotide is extended by the addition of covalently bonded nucleotide bases to its 3'-terminus, which bases are complementary to the template. The result is a primer extension product. A priming oligonucleotide is typically at least 10 nucleotides in length, and may extend up to 15, 20, 25, 30, 35, 40, 50 or more nucleotides in length. Suitable and preferred priming oligonucleotides are described herein. Virtually all DNA polymerases (including reverse transcriptases) that are known require complexing of an oligonucleotide to a single-stranded template ("priming") to initiate DNA synthesis, whereas RNA replication and transcription (copying of RNA from DNA) generally do not require a primer. By its very nature of being extended by a DNA polymerase, a priming oligonucleotide does not comprise a 3'-blocking moiety.

A "displacer oligonucleotide" is a priming oligonucleotide that hybridizes to a template nucleic acid upstream from a neighboring priming oligonucleotide hybridized to the 3'-end of a target sequence (referred to herein as the "forward priming oligonucleotide"). By "upstream" is meant that a 3'-end of the displacer oligonucleotide complexes with the template nucleic acid 5' to a 3'-end of the forward priming oligonucleotide. When hybridized to the template nucleic acid, the 3'-terminal base of the displacer oligonucleotide is preferably adjacent to or spaced from the 5-terminal base of the forward priming oligonucleotide. More preferably, the 3'-terminal base of the displacer oligonucleotide is spaced from 5 to 35 bases from the 5'-terminal base of the forward priming oligonucleotide. The displacer oligonucleotide may be provided to a reaction mixture contemporaneously with the forward priming oligonucleotide or after the forward priming oligonucleotide has had sufficient time to hybridize to the template nucleic acid. Extension of the forward priming oligonucleotide can be initiated prior to or after the displacer oligonucleotide is provided to a reaction mixture. Under amplification conditions, the displacer oligonucleotide is extended in a template-dependent manner, thereby displacing a primer extension product comprising the forward priming oligonucleotide that is complexed with the template nucleic acid. Once displaced from the template nucleic acid, the primer extension product comprising the forward priming oligonucleotide is available for complexing with a promoter oligonucleotide. The forward priming oligonucleotide and the displacer oligonucleotide both preferentially hybridize to the target nucleic acid. Examples of displacer oligonucleotides and their uses are disclosed by Becker et al., U.S. Pub. No. US 20070202523 A1, commonly owned herewith.

As used herein, a "blocking moiety" is a substance used to "block" the 3'-terminus of an oligonucleotide or other nucleic acid so that it cannot be efficiently extended by a nucleic acid polymerase. A blocking moiety may be a small molecule, e.g., a phosphate or ammonium group, or it may be a modified nucleotide, e.g., a 3'2' dideoxynucleotide or 3' deoxyadenosine 5'-triphosphate (cordycepin), or other modified nucleotide. Additional blocking moieties include, for example, the use of a nucleotide or a short nucleotide sequence having a 3'-to-5' orientation, so that there is no free hydroxyl group at the 3'-terminus, the use of a 3' alkyl group, a 3' non-nucleotide moiety (see, e.g., Arnold et al., U.S. Pat. No. 6,031,091), phosphorothioate, alkane-diol residues, peptide nucleic acid (PNA), nucleotide residues lacking a 3' hydroxyl group at the 3'-terminus, or a nucleic acid binding protein. Preferably, the 3'-blocking moiety comprises a nucleotide or a nucleotide sequence having a 3'-to-5' orientation or a 3' non-nucleotide moiety, and not a 3'2'-dideoxynucleotide or a 3' terminus having a free hydroxyl group. Additional methods to prepare 3'-blocking oligonucleotides are well known to those of ordinary skill in the art.

As used herein, a "binding molecule" is a substance which hybridizes to or otherwise binds to an RNA target nucleic acid adjacent to or near the 5'-end of the desired target sequence, so as to limit a DNA primer extension product to a desired length, i.e., a primer extension product having a generally defined 3'-end. As used herein, the phrase "defined 3'-end" means that the 3'-end of a primer extension product is not wholly indeterminate, as would be the case in a primer extension reaction which occurs in the absence of a binding molecule, but rather that the 3'-end of the primer extension product is generally known to within a small range of bases. In certain embodiments, a binding molecule comprises a base region. The base region may be DNA, RNA, a DNA:RNA chimeric molecule, or an analog thereof. Binding molecules comprising a base region may be modified in one or more ways, as described herein. Exemplary base regions include terminating and digestion oligonucleotides, as described below. In other embodiments, a binding molecule may comprise, for example, a protein or drug capable of binding RNA with sufficient affinity and specificity to limit a DNA primer extension product to a pre-determined length.

As is used herein, a "terminating oligonucleotide" is an oligonucleotide comprising a base sequence that is complementary to a region of a target nucleic acid sequence in the vicinity of the 5'-end of the target sequence, so as to "terminate" primer extension of a nascent nucleic acid that includes a priming oligonucleotide, thereby providing a defined 3'-end for the nascent nucleic acid strand. A terminating oligonucleotide is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-Me ribonucleotides. These modified nucleotides have demonstrated higher thermal stability of complementary duplexes. The 2'-O-Me ribonucleotides also function to increase the resistance of oligonucleotides to exonucleases, thereby increasing the half-life of the modified oligonucleotides. See, e.g., Majlessi et al. (1988) Nucleic Acids Res. 26, 2224-9. Other modifications as described elsewhere herein may be utilized in addition to or in place of 2'-O-Me ribonucleotides. For example, a terminating oligonucleotide may comprise PNA or an LNA. See, e.g., Petersen et al. (2000) J. Mol. Recognit. 13, 44-53. A terminating oligonucleotide typically includes a blocking moiety at its 3'-terminus to prevent extension. A terminating oligonucleotide may also comprise a protein or peptide joined to the oligonucleotide so as to terminate further extension of a nascent nucleic acid chain by a polymerase. A terminating oligonucleotide is typically at least 10 bases in length, and may extend up to 15, 20, 25, 30, 35, 40, 50 or more nucleotides in length. Suitable and preferred terminating oligonucleotides are described herein. It should be noted that while a terminating oligonucleotide typically or necessarily includes a 3'-blocking moiety, "3'-blocked" oligonucleotides are not necessarily terminating oligonucleotides. Other oligonucleotides used herein, e.g., promoter oligonucleotides and capping oligonucleotides, are typically or necessarily 3'-blocked as well.

As used herein, an "insertion sequence" is a sequence positioned between the first region (i.e., template binding portion) and the second region of a promoter oligonucleotide. Insertion sequences are preferably 5 to 20 nucleotides in length, more preferably 6 to 18 nucleotides in length, and most preferably 6 to 12 nucleotides in length. The inclusion of insertion sequences in promoter oligonucleotides increases the rate at which RNA amplification products are formed.

"Target capture," as used herein, includes any technique effective to remove all or substantially all unhybridized inactivatable target capture oligomer, as well as any other nucleic acid reagent, non-target nucleic acid, unhybridized target nucleic acid or non nucleic acid component in a reaction mixture. Generally, target capture involves capturing a target polynucleotide onto a solid support, such as magnetically attractable particles, where the solid support retains the target polynucleotide during one or more washing steps of the target polynucleotide purification procedure. In this way, a target polynucleotide is substantially purified from unhybridized inactivatable target capture oligomer, as well as any other nucleic acid reagent, non-target nucleic acid, unhybridized target nucleic acid or non nucleic acid component prior to any subsequent analysis steps. Numerous target capture methods are known and suitable for use in conjunction with the methods described herein.

For example, one illustrative approach described in U.S. Pub. No. US 20060068417 A1 uses at least one capture probe oligonucleotide that contains a target-complementary region and a member of a specific binding pair that joins a target nucleic acid to an immobilized probe on a capture support, thus forming a capture hybrid that is separated from other sample components of a sample. Another illustrative method, Weisburg et al., U.S. Pat. No. 6,110,678, describes a method for capturing a target polynucleotide in a sample onto a solid support, such as magnetically attractable particles, with an attached immobilized probe by using a capture probe and two different hybridization conditions, which preferably differ in temperature only. The two hybridization conditions control the order of hybridization, where the first hybridization conditions allow hybridization of the capture probe to the target polynucleotide, and the second hybridization conditions allow hybridization of the capture probe to the immobilized probe. The method may be used to detect the presence of a target polynucleotide in a sample by detecting the captured target polynucleotide or amplified target polynucleotide. Another illustrative target capture technique involves a hybridization sandwich technique for capturing and for detecting the presence of a target polynucleotide. See Ranki et al., U.S. Pat. No. 4,486,539. The technique involves the capture of the target polynucleotide by a probe bound to a solid support and hybridization of a detection probe to the captured target polynucleotide. Detection probes not hybridized to a target nucleic acid are readily washed away from the solid support. Thus, remaining label is associated with the target polynucleotide initially present in the sample.

Another illustrative target capture technique involves a method that uses a mediator polynucleotide that hybridizes to both a target nucleic acid and to a polynucleotide fixed on a solid support. See Stabinsky, U.S. Pat. No. 4,751,177. The mediator polynucleotide joins the target polynucleotide to the solid support to produce a bound target. A labeled probe can be hybridized to the bound target and unbound labeled pro can be washed away from the solid support. Yet another illustrative target capture technique is disclosed by Englelhardt, U.S. Pat. No. 5,288,609, which describes a method for detecting a target polynucleotide. The method utilizes two single-stranded polynucleotide segments complementary to the same or opposite strands of the target and results in the formation of a double hybrid with the target polynucleotide. In one embodiment, the hybrid is captured onto a support.

In another illustrative target capture technique, methods and kits for detecting nucleic acids use oligonucleotide primers labeled with specific binding partners to immobilize primers and primer extension products. See Burdick et al., European Pat. Appln. No. 0 370 694 A2. The label specifically complexes with its receptor which is bound to a solid support. The above capture techniques are illustrative only, and not limiting. Indeed, essentially any technique available to the skilled artisan may be used provided it is effective for removing all or substantially all unhybridized inactivatable target capture oligomer, after hybridization of inactivatable target capture oligomer with a target nucleic acid sequence but prior to downstream analysis (e.g., amplification) of the target nucleic acid sequence.

The term "inactivatable target capture oligomer" refers to an oligonucleotide that is capable of selectively hybridizing to a target nucleic acid. Inactivatable target capture oligomers of the current invention preferably comprise a target hybridizing region, a tag-closing region and a binding pair member. Two or more of these regions can be joined as contiguous nucleic acid sequences.

Alternatively, any two regions can be joined using a non-nucleotide linker. Alternatively still, the tag-closing sequence can be a discrete molecule. Contiguously joined regions and members can be arranged 5' to 3' or 3' to 5', depending on preference. When non-nucleotide linkers are used to join regions, orientations can further include 5' to 5' or 3' to 3'. Preferably, the regions are joined as contiguous nucleic acid sequences, wherein the target hybridizing region is joined at its 3' end to the 5' end of a tag-closing region and the tag-closing region is joined at its 3' end to a binding pair member. If the binding pair member is a nucleic acid sequence region, then the tag-closing region is joined at its 3' end to the 5' end of the binding pair member. In an alternative orientation, the target hybridizing region is joined at its 5' end to the 3' end of a tag-closing region and the tag-closing region is joined at its 5' end to a binding pair member, which, if the binding pair member is a nucleic acid sequence region, then the tag-closing region is joined at its 5' end to the 3' end of the binding pair member. When the binding pair member is a non-nucleic acid sequence, it can be covalently linked to the nucleic acid tag-closing region, for example. (See e.g., FIGS. 24-25) Compositions and methods for linking nucleic acid regions and for linking non-nucleic acid moieties to a nucleic acid are known in the art. Other configurations of the inactivatable target capture oligomer, there is provided a target region joined on one of its ends to a binding pair member and the tag-closing region is a discrete molecule or is joined by a linker to an end on the target capture region that is opposite the end joined to the binding pair member (e.g., FIGS. 22-23). Essentially, the binding pair member and the tag-closing region are bound to opposites ends of the target hybridizing region.

Inactivatable target capture oligomers of the current invention are configured to provide, under certain conditions, an active configuration and an inactive configuration. Thus, the tag-closing region is configured so that under a first set of conditions wherein the target hybridizing region stably hybridizes with a target nucleic acid sequence, this tag-closing region does not stably hybridize with the target nucleic acid or any known non-target or contaminating nucleic acid sequences believed to be in a sample. But, under a second set of conditions, the tag-closing region hybridizes with the target hybridizing region, thereby preventing further hybridization of the inactivated inactivatable target capture oligomer with any non-target or contaminating nucleic acid sequences. Preferably, the active and inactive configurations are linear or hairpin configurations, respectively. However, in the embodiments wherein a tag-closing region is a discrete molecule from the target hybridizing region and binding pair member molecule, then active and inactive configurations for these two discrete molecules occurs when the molecules are dissociated and hybridized, respectively. Preferably, the hairpin configuration forming the inactive inactivatable target capture oligomer comprises a self-hybridization event wherein the tag-closing region and a portion of the target hybridizing region hybridize together thereby blocking the target hybridizing region from further hybridizing a nucleic acid in the reaction mixture. Alternatively for the configuration wherein the binding pair member and the tag-closing region are joined to opposite ends of the target hybridizing region, the inactivated configuration is still a hairpin configuration wherein the tag-closing region and a portion of the target hybridizing region hybridize together thereby blocking the target hybridizing region from further hybridizing a nucleic acid in the reaction mixture. In configurations wherein the tag-closing region is a discreet oligomer, hybridization of the discrete closing oligomer to the target hybridization region inactivates inactivatable target capture oligomer.

Preferably the binding pair member of an inactivatable target capture oligomer is a substantially homopolymeric nucleic acid sequence that is complementary to a substantially homopolymeric nucleic acid sequence second binding pair member of a solid support. Thus, members of the binding pair are complementary polynucleotides that are unlikely to participate in stable, non-specific binding reactions (e.g., poly(dA) and poly(dT) sequences of similar length). Weisburg et al., U.S. Pat. No. 6,534,273. Non-nucleic acid binding pair members include, but are not limited to, ligand-ligate (e.g., avidin-biotin linkage). While the preferred capture probe binds to both the target nucleic acid and a second, immobilized binding pair member under the same conditions, the capture probe may be designed so that the target hybridizing sequence and the second binding pair member bind to their counterparts under different conditions. In this way, the capture probe may be designed so that it first binds the target nucleic acid under more favorable in solution kinetics before adjusting the conditions to permit binding of the first binding pair member to the second binding pair member.

The phrases "tag-closing sequence," "capture probe closing sequence" and "capture probe closing oligonucleotide" refer to an oligonucleotide sequence that is complementary to a portion of a target hybridizing sequence of an inactivatable target capture oligomer. The length and sequence of the tag-closing sequence are selected so that the tag-closing sequence does not stably hybridize to the target hybridizing sequence of the inactivatable target capture oligomer under a first set of conditions permitting stable hybridization of the target hybridizing sequence to a target nucleic acid. The tag-closing sequence may include abasic nucleotides or base mismatches with the target hybridizing sequence. Provided an inactivatable target capture oligomer is not hybridized to a target nucleic acid, the tag-closing sequence stably hybridizes to the target hybridizing sequence under a second set of less stringent conditions, thus "inactivating" or blocking the inactivatable target capture oligomer from hybridizing to the non-target and contaminating nucleic acids ("closed capture probe"). As described herein, the tag-closing sequence may be in the form of a discrete oligonucleotide or it may be joined to an end of the target hybridizing sequence. When joined to the target hybridizing sequence, it may be joined as a contiguous nucleotide sequence or through a non-nucleotide linker. Further, the tag-closing sequence may be joined to the target hybridizing sequence at an end of the target hybridizing sequence opposite the end joined to the binding pair member. Alternatively, the tag-closing may be joined on one of its ends to the target hybridizing region and on the other of its ends to the binding pair member. When the tag-closing sequence is not a discrete molecule, then the inactivatable target capture oligomer forms a hairpin structure under the second set of conditions. If the inactivatable target capture oligomer has a terminal 3' end that can be used in a primer-based extension, and such extension is not desired, then that 3' terminal residue is preferably modified to prevent the initiation of DNA synthesis therefrom, which can include using a blocking moiety situated at its 3'-terminus. In some alternative embodiments wherein the inactivatable target capture oligomer is also used as a priming oligomer, the inactivatable target capture oligomer can further comprise a tag region to introduce a unique site into a first amplification product. Subsequent amplification can use an amplification oligomer that hybridizes to this tag region, or a complement thereof. Optionally, the tag region can be the same as or can overlap with the tag-closing region. If the inactivatable target capture oligomer forms a hairpin structure under the second set of conditions, then the target hybridizing sequence preferably hybridizes to the tag-closing sequence. The tag-closing sequence is at least 3 but no more than about 20 bases in length, preferably at least 5 but no more than 20 bases in length, and more preferably from 6 to 14 bases in length, and more preferably still 6 to 9 nucleobases in length.

By "probe" or "detection probe" is meant a molecule comprising an oligonucleotide having a base sequence partly or completely complementary to a region of a target sequence sought to be detected, so as to hybridize thereto under stringent hybridization conditions. As would be understood by someone having ordinary skill in the art, a probe comprises an isolated nucleic acid molecule, or an analog thereof, in a form not found in nature without human intervention (e.g., recombined with foreign nucleic acid, isolated, or purified to some extent). Detection probes may have additional nucleosides or nucleobases outside of the targeted region so long as such nucleosides or nucleobases do not substantially affect hybridization under stringent hybridization conditions and, in the case of detection probes, do not prevent preferential hybridization to the target nucleic acid. A non-complementary sequence may also be included, such as a target capture sequence (generally a homopolymer tract, such as a poly-A, poly-T or poly-U tail), promoter sequence, a binding site for RNA transcription, a restriction endonuclease recognition site, or may contain sequences which will confer a desired secondary or tertiary structure, such as a catalytic active site or a hairpin structure on the probe, on the target nucleic acid, or both. Detection probes preferably include at least one detectable label. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particularly preferred embodiment, the label is an acridinium ester. Probes may also include interacting labels that emit different signals, depending on whether the probes have hybridized to target sequences. Examples of interacting labels include enzyme/substrates, enzyme/cofactor, luminescent/quencher, luminescent/adduct, dye dimers, and Forrester energy transfer pairs. Certain probes do not include a label; for example, non-labeled capture probes may be used to enrich for target sequences or replicates thereof, which may then be detected by a second "detection" probe. See, e.g., Weisburg et al., U.S. Pat. No. 6,534,273. While detection probes are typically labeled, certain detection technologies do not require that the probe be labeled. See, e.g., Nygren et al., U.S. Pat. No. 6,060,237. Probes of a defined sequence may be produced by techniques known to those of ordinary skill in the art, such as by chemical synthesis, and by in vitro or in vivo expression from recombinant nucleic acid molecules. Preferably probes are 10 to 100 nucleotides in length, more preferably 12 to 50 bases in length, and even more preferably 18 to 35 bases in length.

By "stable" or "stable for detection" is meant that the temperature of a reaction mixture is at least 2.deg.C. below the melting temperature of a nucleic acid duplex. The temperature of the reaction mixture is more preferably at least 5.deg.C. below the melting temperature of the nucleic acid duplex, and even more preferably at least 10.deg.C. below the melting temperature of the reaction mixture.

"Nucleic Acid Identity" means a nucleic acid comprising a contiguous base region that is at least 80%, 90%, or 100% identical to a contiguous base region of a reference nucleic acid. For short nucleic acids, e.g., certain oligonucleotides of the present invention, the degree of identity between a base region of a "query" nucleic acid and a base region of a reference nucleic acid can be determined by manual alignment. "Identity" is determined by comparing just the sequence of nitrogenous bases, irrespective of the sugar and backbone regions of the nucleic acids being compared. Thus, the query:reference base sequence alignment may be DNA:DNA, RNA:RNA, DNA:RNA, RNA:DNA, or any combinations or analogs thereof. Equivalent RNA and DNA base sequences can be compared by converting U's (in RNA) to T's (in DNA). Differences between two nucleic acid sequences being compared can include nucleotide additions, deletions, substitutions and modification in one sequence compared to the other.

A "template" is a nucleic acid molecule that is being copied by a nucleic acid polymerase. A template may be single-stranded, double-stranded or partially double-stranded, depending on the polymerase. The synthesized copy is complementary to the template or to at least one strand of a double-stranded or partially double-stranded template. Both RNA and DNA are typically synthesized in the 5'-to-3' direction and the two strands of a nucleic acid duplex are aligned so that the 5'-termini of the two strands are at opposite ends of the duplex (and, by necessity, so then are the 3'-termini) Templates comprise the target sequence, and in some instances also comprise secondary primer extension products, such as tag sequences or promoter sequences.

A "DNA-dependent DNA polymerase" is an enzyme that synthesizes a complementary DNA copy from a DNA template. Examples are Taq DNA polymerase, a highly thermostable DNA polymerase from the thermophilic bacterium *Thermus aquaticus*, for PCR amplification reactions, DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases (described below) typically also have DNA-dependent DNA polymerase activity. An example of such a polymerase is the MasterAmp.sup.™ Tth DNA Polymerase, which has both DNA-dependent and RNA-dependent (i.e., reverse transcriptase) DNA polymerase activities that can be used in both PCR and RT-PCR amplification reactions (Epicentre Biotechnologies, Madison, Wis.).

A "DNA-dependent RNA polymerase" or "transcriptase" is an enzyme that synthesizes multiple RNA copies from a double-stranded or partially-double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from E. coli and bacteriophages T7, T3, and SP6.

An "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. Preferred is reverse transcriptase derived from Maloney murine leukemia virus (MMLV-RT). A primer is required to initiate synthesis with both RNA and DNA templates.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes other than RNAse H but that possess the same or similar activity are also contemplated herein. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes that selectively degrade RNA target sequences or RNA products of the present invention are readily apparent to those of ordinary skill in the art.

Sense/Antisense Strand(s): Discussions of nucleic acid synthesis are greatly simplified and clarified by adopting terms to name the two complementary strands of a nucleic acid duplex. Traditionally, the strand encoding the sequences used to produce proteins or structural RNAs are designated as the "sense (+)" strand and its complement the "antisense (−)" strand. It is now known that in many cases, both strands are functional, and so the assignment of the designation "sense" to one and "antisense" to the other has become arbitrary. Nevertheless, the terms can be helpful for designating the sequence orientation of nucleic acids and may be employed herein for that purpose.

The term "specificity," in the context of a selective hybridization and capture system, or in the context of an amplification system, is used herein to refer to the characteristic that describes it's the ability of a system to distinguish between target and non-target sequences, dependent upon sequence and assay conditions. In terms of selective target nucleic hybridization and capture, specificity generally refers to the ratio of the number of target nucleic acids hybridized and captured to the number of non-target and contaminating nucleic acids hybridized and captures, as discussed herein. In terms of nucleic acid amplification, specificity generally refers to the ratio of the number of specific amplicons produced to the number of side-products (i.e., the signal-to-noise ratio), as discussed herein.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and often depends, for example, on the detection assay being employed, and the specificity of the capture and amplification reactions, e.g., side-product or non-target/contaminant amplification reactions.

A "bioprocess," as used herein, refers generally to any process in which living cells, or components thereof, are present, either intended or unintended. For example, essentially any manufacturing or other process that employs one or more samples or sample streams, at least one of which comprises living cells, or components thereof, or may comprise such cells or components as a result of unintended contamination, is considered a bioprocess. In many such processes it is desirable to have the ability to detect, identify and/or control the presence and/or sources of living cells or components thereof within a process. Using the compositions, kits and methods of the present invention, for example, the presence and/or sources of target nucleic acids from known or suspected bioprocess-contaminating microorganisms or other biological material or components thereof in one or more bioprocess samples or streams may be monitored. In addition, the purification/sterilization requirements within certain samples/streams of a bioprocess may be advantageously reduced using the methods of the invention as set forth herein.

As discussed above, the present invention is directed generally to compositions, kits and methods for the selective hybridization of an inactivatable target capture oligomer to a target nucleic acid. The active form of the inactivatable target capture oligomer selectively hybridizes to target nucleic acids under a first set of conditions. Unhybridized inactivatable target capture oligomers are inactivated under a second set of conditions. In activating the inactivatable target capture oligomer substantially reduces or eliminates non-specific binding of the capture probe to any non-target nucleic acids or contaminating nucleic acids present in a reaction mixture. Further provided, hybridization complexes comprising inactivatable target capture oligomers and target nucleic acids can be captured, for example by providing a solid support comprising a complementary second binding pair member. Selectively hybridized nucleic acids are then available for downstream analyses, such as nucleic acid amplification. Non-target nucleic acids and/or contaminating nucleic acids are, thusly, substantially reduced or eliminated, thereby providing for improvements in subsequent analyses. For example, when the downstream analyses is amplification and detection of a target nucleic acid, there is a reduction or elimination in false positive amplification signals resulting from contaminating nucleic acid material that may be present in one or more reagents, samples or components that are used in an amplification reaction, or that may be present in the environment in which amplification reactions are performed. The invention further offers the advantage of requiring less stringent purification and/or sterility efforts conventionally needed in order to ensure that enzymes, other reagents, labwares, and reaction environments used in subsequent analyses reactions, are free of bacterial and other nucleic acid contamination that may yield false positive results. Accordingly, the methods of the invention are particularly useful in detecting, monitoring and/or quantitating target nucleic acids from a variety of samples, including those typically known to encounter diminished results due to non-target nucleic acids and/or contaminating nucleic acids. The amplification reactions can be essentially any amplification procedure requiring a template-binding priming oligonucleotide capable of extension in the presence of nucleic acid polymerase.

Figure 26:
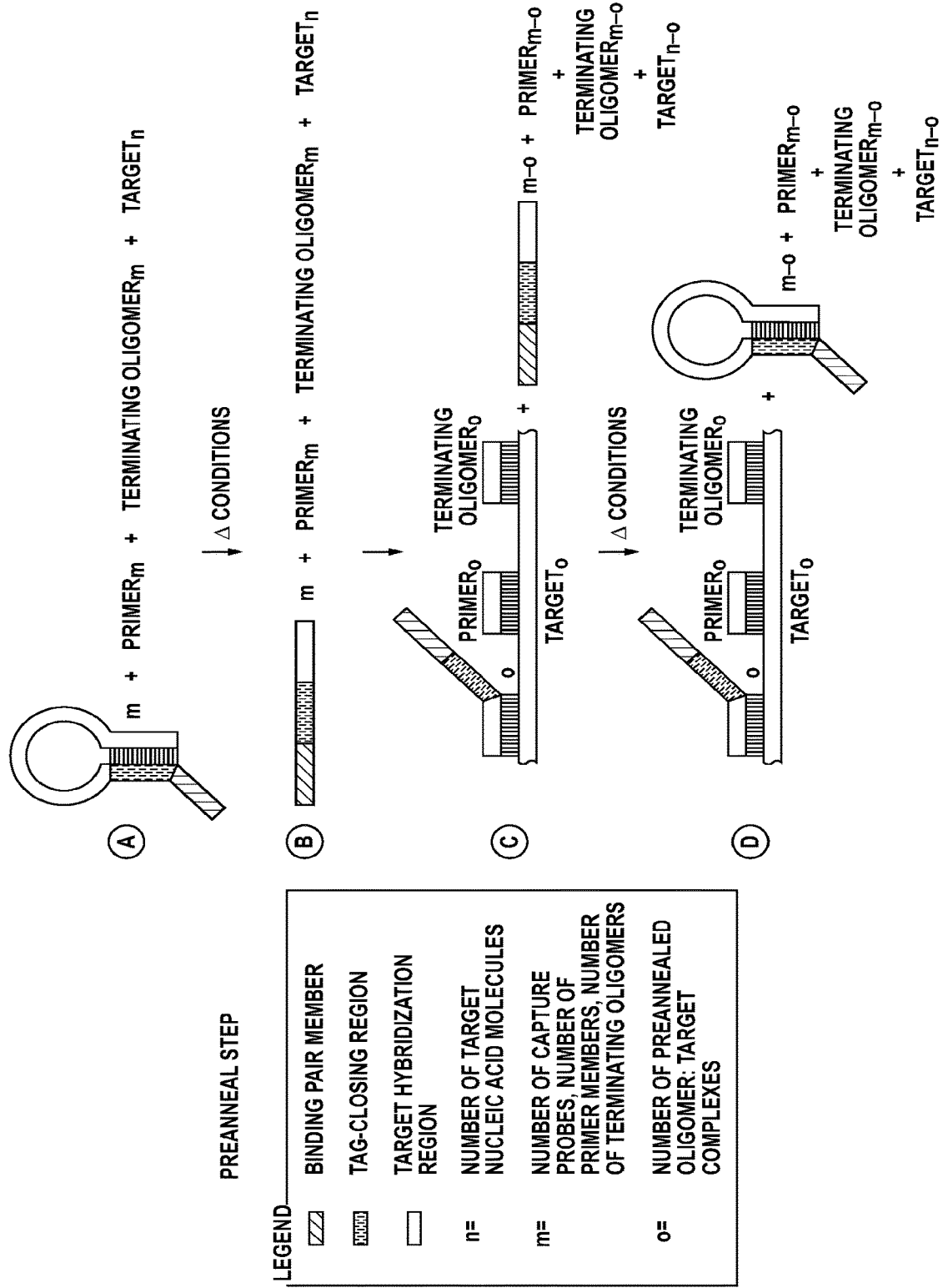
FIGS. 26 and 27 illustrate some method steps of the selective capture and capture of a target nucleic acid sequence using the compositions of the current invention. Also illustrated in these figures is the optional preannealing of an amplification oligomer and blocker oligomer for a preamplification step. This optional part of the illustration is not limiting, but rather is exemplary. The type of amplification oligomer used in this optional step can be a heterologous amplification oligomer, a primer oligomer or a promoter oligomer, as described herein.
Figure 27:
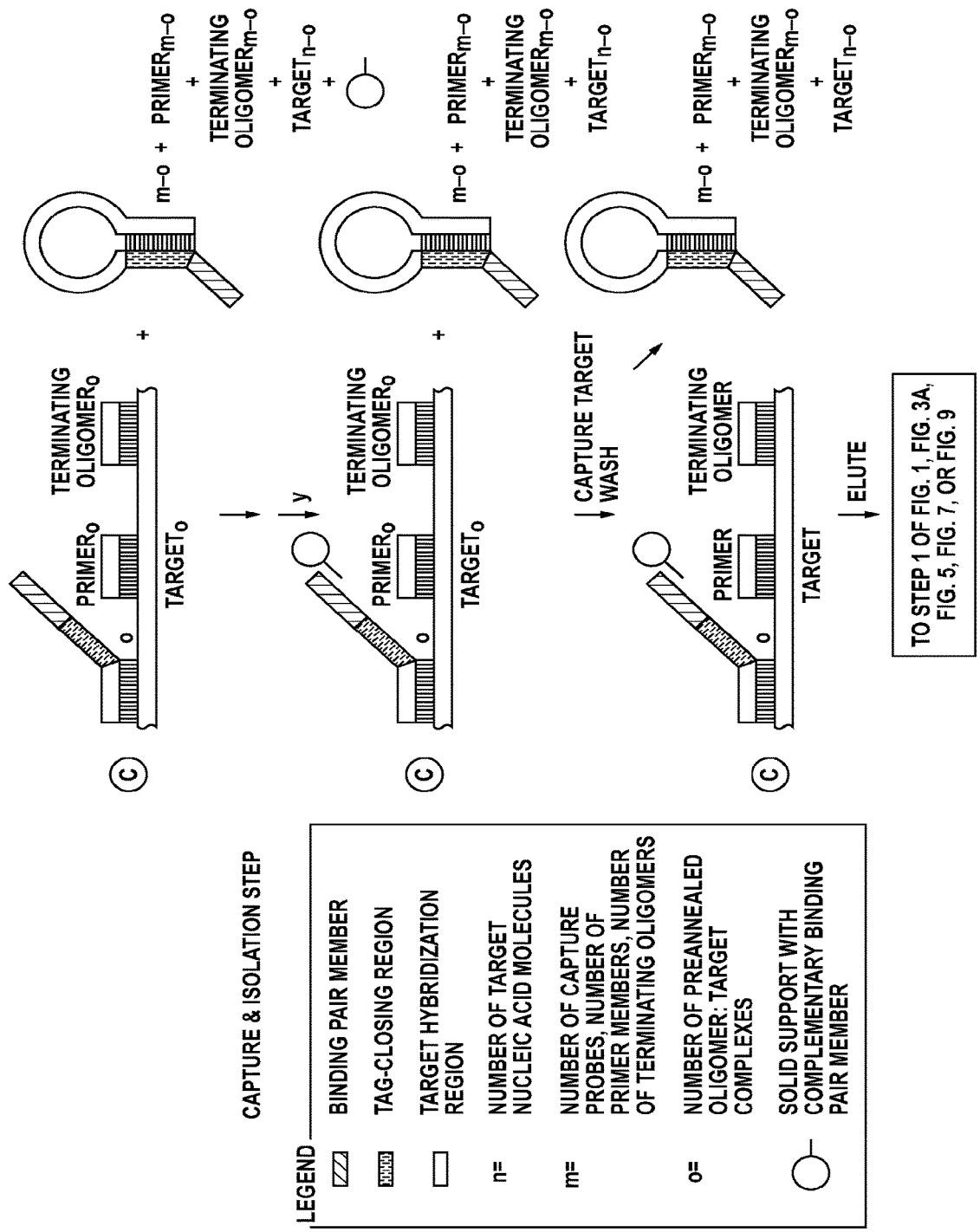

FIGS. 26 and 27 are an exemplary illustration of selective hybridization (FIG. 26) and capture (FIG. 27) of a target nucleic acid. Further illustrated in FIG. 27 is an optional wash step. Also illustrated and optional in these FIGS. is the inclusion of a heterologous amplification oligomer and a terminating oligomer. The exemplary illustration of these FIGS. 26-27, then, is for a downstream amplification reaction, including, but not being limited to, those illustrated in FIGS. 1, 3A-B, 5, 7 and 9. The compositions, kits and methods of the current invention are not limited to hybridizing and capturing target nucleic acids for a downstream amplification reaction.

In FIG. 26, step A illustrates an inactivatable target capture oligomer comprising a target hybridizing region, a tag-closing region and a binding pair member. The inactivatable target capture oligomer is illustrated in the closed configuration. Also illustrated in step A is a primer, a terminating oligomer and a target nucleic acid. Preferably, though not necessarily, the primer member comprises a tag sequence (not shown), and so it a heterologous amplification oligomer. The designations "m" and "n" represent copy numbers for these components and the target nucleic acid, respectively. A first conditions in then achieved so that in step B the inactivatable target capture oligomer is in an active configuration. This first condition is sufficiently stringent that the active inactivatable target capture oligomer, the primer and the terminating oligomer hybridize to the target nucleic acid, forming a preannealing complex. Step C. The number of preannealing complexes formed in a reaction will be limited because of the lesser of the added components, the target and/or other limiting factors. Thus, the number of complexes formed is represented by the "o" designation. Therefore, step C indicates that unhybridized active inactivatable target capture oligomer, primer and terminating oligomer are present in an amount of m-o, while excess target nucleic acids are present in an amount of n-o, wherein if o>m the amount is 0 and if o>n the amount is 0. Ordinarily skilled artisans understand that such a reaction can have excess components or target. A second set of conditions is achieved next to inactivate any unhybridized inactivatable target capture oligomers, thereby substantially reducing or eliminating their ability to hybridize to non-target nucleic acids or contaminating nucleic acids; step D. In a reaction that includes a primer oligomer, and wherein that primer oligomer is a heterologous amplification oligomer, a similar inactivating event can take place under these second conditions.

FIG. 27 illustrates the addition of a solid support comprising a complementary second binding pair member; step A. Ordinarily skilled artisans understand capture of nucleic acids using solid supports comprising second binding pair members. In a preferred embodiment, the solid support is a magnetic bead comprising a substantially homopolymeric binding pair member that is complementary to the binding pair member of the inactivatable target capture oligomer. At step B the preannealing complex formed in step D of FIG. 26 is further complexed with the solid support comprising a second binding pair member. Preferably at this point, the inactive inactivatable target capture oligomer, the unhybridized primer and terminating oligomers and any unhybridized target nucleic acids are removed from the captured complex in a series of wash and rinse steps. Further, any non-target or contaminating nucleic acids in the reaction mixture are removed from the reaction by the wash/rinse steps. Thus, at C there is illustrated a captured complex that is isolated away from the inactivated inactivatable target capture oligomer, the unhybridized primer and terminating oligomers and any unhybridized target nucleic acids. Captured target nucleic acids are then used in a downstream procedure. In the example illustrated in FIGS. 26 and 27, the captured target nucleic acid comprises components for an amplification reaction. Thus, the illustrated captured target nucleic acids can be eluted to, for example, step 1—of any one of FIG. 1, 3A, 5, 7 or 9. Or, alternatively, a polymerase can be added at one of the steps in FIG. 27 to synthesize a complementary copy of the target nucleic acid, thereby providing a nucleic acid strand that is complementary to the target and that incorporates the sequence of the primer member. In the embodiments wherein that primer member is a heterologous amplification oligomer, then a tag sequence is further incorporated into the nascent sequence. In these instances, the captured target nucleic acids and complementary strand containing a tag sequence can be eluted into, for example, step 3 of FIG. 1, step 3 of FIG. 3A, step 5 of FIG. 5, step 5 of FIG. 7, or step 3 of FIG. 9. Such are merely exemplary and do not limit the invention.

Ordinarily skilled artisans in possession of this specification will understand that the compositions, kits and methods of the current invention are not limited to downstream analyses that are amplification reactions. And further, when the downstream analyses are amplification reactions, the types of reactions and the order of the steps as illustrated and exemplified herein, do not limit the invention. The following further illustrates some of the exemplary downstream amplification reactions.

FIG. 1 illustrates an adaptation of an isothermal, transcription-based amplification reaction known as reverse transcription-mediated amplification (rTMA), various aspects of which are disclosed in Becker et al., U.S. Pub. No. U.S. 2006-0046265 A1. The reaction of this illustrative embodiment is initiated by treating an RNA target sequence in a nucleic acid sample with both a tagged priming oligonucleotide (also referred to as a heterologous amplification oligomer) and a terminating oligonucleotide. The tagged priming oligonucleotide includes a target hybridizing sequence that hybridizes to a 3'-end of the target sequence and a tag sequence (also referred to as a tags sequence) situated 5' to the target hybridizing sequence. The terminating oligonucleotide hybridizes to a target nucleic acid containing the target sequence in the vicinity of the 5'-end of the target sequence. The terminating oligonucleotide is used to end primer extension of a nascent nucleic acid that includes the tagged priming oligonucleotide. Thus, the target nucleic acid forms a stable complex with the tagged priming oligonucleotide at the 3'-end of the target sequence and the terminating oligonucleotide located adjacent to or near the 5'-end of the target sequence prior to initiating a primer extension reaction. See FIG. 1, Step 1. Unhybridized tagged priming oligonucleotide is preferably made unavailable for hybridization to the target sequence prior to initiating a primer extension reaction with the tagged priming oligonucleotide, preferably by inactivating and/or removing the unhybridized tagged priming oligonucleotide from the nucleic acid sample. An extension reaction is then initiated from the 3'-end of the hybridized tagged priming oligonucleotide with a DNA polymerase, e.g., reverse transcriptase, to produce a first DNA primer extension product that includes the tag sequence and a region complementary to the target sequence. See FIG. 1, Steps 2 and 3. The first DNA primer extension product is then separated from the target sequence using an enzyme that selectively degrades the target sequence (e.g., RNAse H activity). See FIG. 1, Step 4.

Next, the first DNA primer extension product is treated with a promoter oligonucleotide having a hybridizing sequence and a promoter for an RNA polymerase situated 5' to the hybridizing sequence. The hybridizing sequence hybridizes to a region of the first DNA primer extension product that is complementary to the 3'-end of the target sequence, thereby forming a promoter oligonucleotide:first DNA primer extension product hybrid. In the illustrated reaction, the promoter oligonucleotide is modified to prevent the initiation of DNA synthesis, preferably by situating a blocking moiety at the 3'-end of the promoter oligonucleotide (e.g., nucleotide sequence having a 3'-to-5' orientation). See FIG. 1, Step 5. The 3'-end of the first DNA primer extension product is preferably extended to add a sequence complementary to the promoter, resulting in the formation of a double-stranded promoter sequence. See FIG. 1, Steps 6 and 7. Multiple copies of a first RNA product complementary to at least a portion of the first DNA primer extension product, not including the promoter portion, are then transcribed using an RNA polymerase which recognizes the double-stranded promoter and initiates transcription therefrom. See FIG. 1, Steps 8 and 9. As a result, the base sequence of the first RNA product is substantially identical to the base sequence of the target sequence and the complement of the tag sequence provided by the heterologous amplification oligomer in steps 1-3.

In amplification reactions that use a heterologous amplification oligomer, subsequent rounds of amplification can take advantage of this incorporated tag sequence by including an amplification oligomer that hybridizes to the tag sequence. Because the tag sequence is a unique nucleic acid sequence relative to a reaction mix's nucleic acid environment, which includes the target nucleic acid sequence, and nucleic acids sequences of suspected non-target nucleic acids and contaminating nucleic acids, subsequent amplification rounds are substantially limited to or exclusive for the target nucleic acid sequence. In FIG. 1, first RNA products are treated with a priming oligonucleotide that hybridizes to the complement of the tag sequence to form a priming oligonucleotide:first RNA product hybrid, and the 3'-end of the priming oligonucleotide is extended with the DNA polymerase to produce a second DNA primer extension product complementary to the first RNA product. See FIG. 1, Steps 10-12. The second DNA primer extension product is then separated from the first RNA product using an enzyme that selectively degrades the first RNA product (e.g., RNAse H activity). See FIG. 1, Step 13.

The second DNA primer extension product is treated with the promoter oligonucleotide, which hybridizes to the 3'-end of the second DNA primer extension product to form a promoter oligonucleotide:second DNA primer extension product hybrid. See FIG. 1, Step 14. The promoter oligonucleotide:second DNA primer extension product hybrid then re-enters the amplification cycle at Step 6 of FIG. 1, where transcription is initiated from the double-stranded promoter and the cycle continues.

Figure 3A:
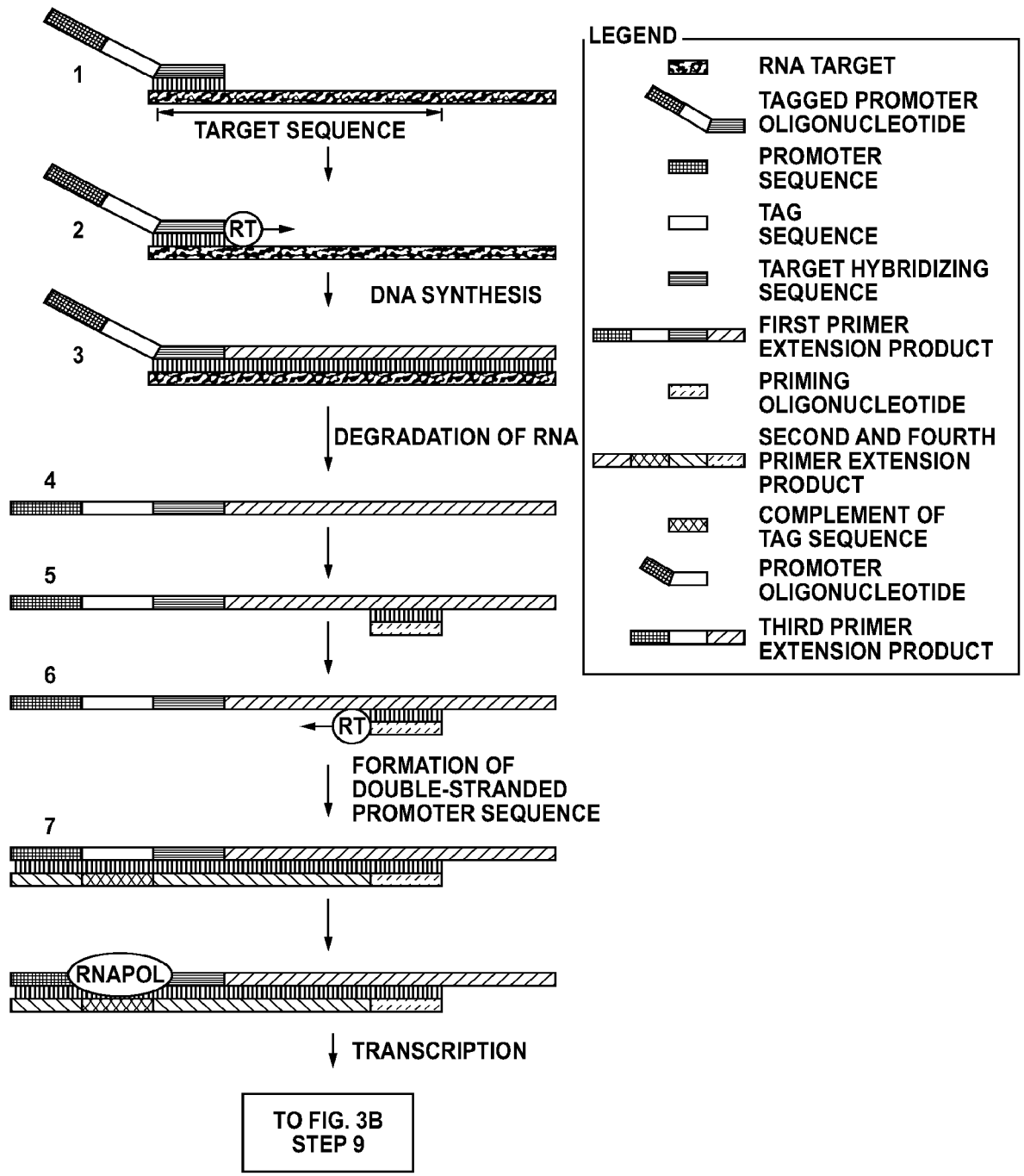
FIGS. 3A and 3B illustrate the steps of a transcription-mediated amplification reaction initiated with a heterologous amplification oligomer that is a tagged promoter oligonucleotide that hybridizes to a 3'-end of an RNA target sequence.
Figure 3B:
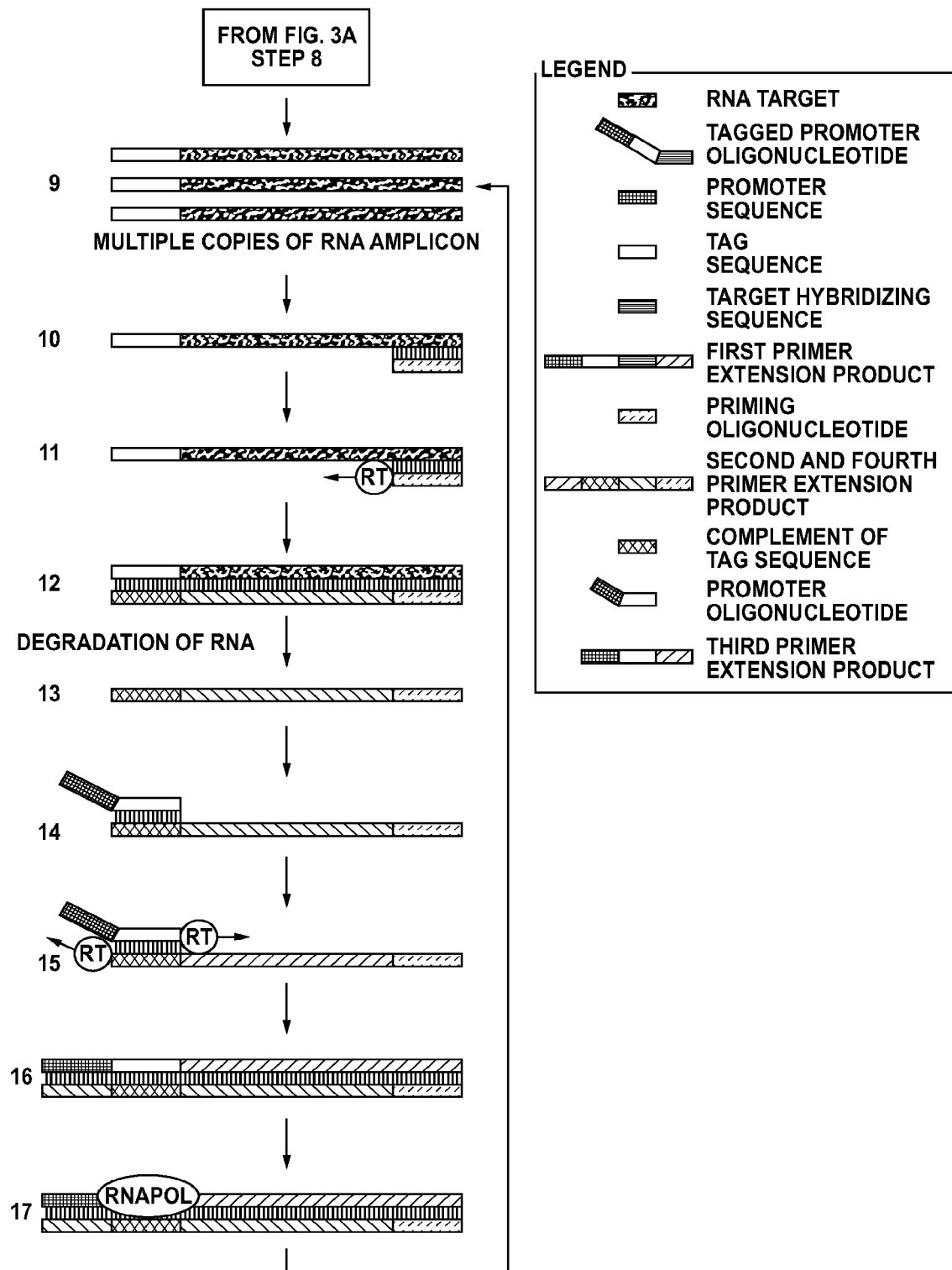
Figure 4:
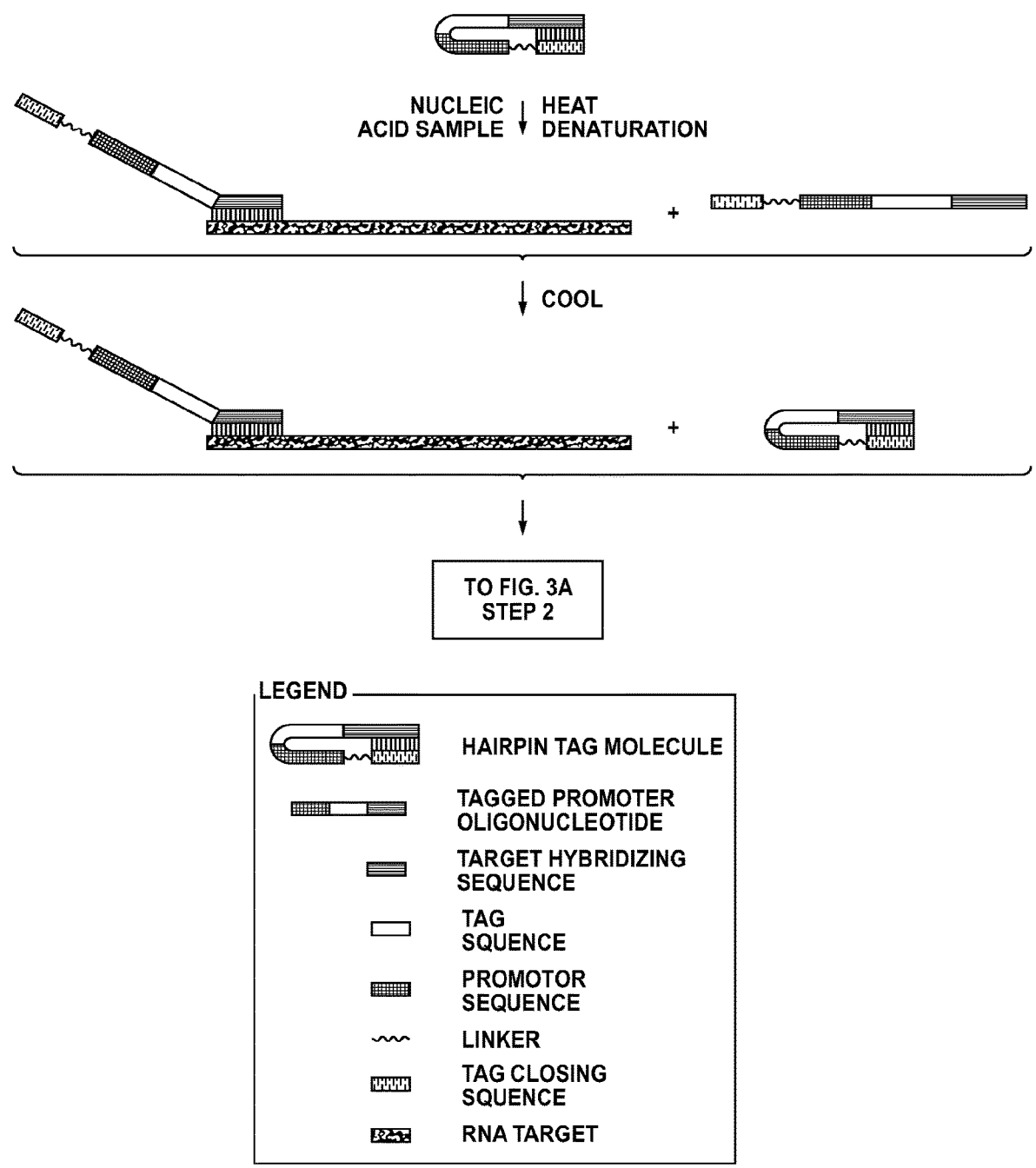

FIGS. 3A-B illustrates an adaptation of an isothermal, transcription-based amplification reaction referred to as transcription-mediated amplification (TMA), various aspects of which are disclosed in Kacian et al., U.S. Pat. Nos. 5,399,491 and 5,824,518. The reaction of this illustrative embodiment is initiated by treating an RNA target sequence in a nucleic acid sample with a heterologous amplification oligomer comprising a promoter region (i.e., a tagged promoter oligonucleotide). Thus, the tagged promoter oligonucleotide includes a tag sequence, a target hybridizing sequence and a promoter sequence for an RNA polymerase, where the target hybridizing sequence hybridizes to a 3'-end of the target sequence. The target sequence forms a stable complex with the tagged promoter oligonucleotide at the 3'-end of the target sequence prior to initiating a primer extension reaction. See FIG. 3A, Step 1. The promoter sequence is situated 5' to the tag sequence, and the tag sequence is situated 5' to the target hybridizing sequence. Unhybridized tagged promoter oligonucleotide is preferably made unavailable for hybridization to the target sequence prior to initiating a primer extension reaction with the tagged priming oligonucleotide, preferably by inactivating and/or removing the unhybridized tagged priming oligonucleotide from the nucleic acid sample. An extension reaction is then initiated from the 3'-end of the tagged promoter oligonucleotide with a DNA polymerase, e.g., reverse transcriptase, to produce a first DNA primer extension product that includes the tag and promoter sequence and a region complementary to the target sequence. See FIG. 1, Steps 2 and 3. The first DNA primer extension product is then separated from the target sequence to which it is hybridized using an enzyme that selectively degrades that portion of the target sequence that is hybridized to the first DNA primer extension product (e.g., RNAse H activity). See FIG. 3A, Step 4.

Next, the first DNA primer extension product is treated with a priming oligonucleotide which hybridizes to a region of the first DNA primer extension product that is complementary to a 5'-end of the target sequence, thereby forming a priming oligonucleotide:first DNA primer extension product hybrid. See FIG. 3A, Step 5. The 3'-end of the priming oligonucleotide is extended by a DNA polymerase to produce a second DNA primer extension product complementary to at least a portion of the first DNA primer extension product, and containing a double-stranded promoter sequence. See FIG. 3A, Steps 6 and 7. This second DNA primer extension product is used as a template to transcribe multiple copies of a first RNA product complementary to the second DNA primer extension product, not including the promoter portion, using an RNA polymerase that recognizes the double-stranded promoter and initiates transcription therefrom. See FIGS. 3A-B, Step 8 and 9. The base sequence of the first RNA product is substantially identical to the base sequence of the complement of the target sequence and the tag sequence, thereby providing the tag sequence for a subsequent amplification oligomer to bind.

The first RNA product is treated with the priming oligonucleotide, the 3'-end of which is extended by the DNA polymerase to produce a third DNA primer extension product complementary to the first RNA product. See FIG. 3B, Steps 10-12. The third DNA primer extension product is then separated from the first RNA product using an enzyme that selectively degrades the first RNA product (e.g., RNAse H activity). See FIG. 3B, Step 13. The third DNA primer extension product is treated with a promoter oligonucleotide having a hybridizing sequence which hybridizes to a complement of the tag sequence at the 3'-end of the third DNA primer extension product, and further comprises a promoter for an RNA polymerase which is situated 5' to the hybridizing sequence. See FIG. 3B, Step 14. The 3'-end of the third DNA primer extension product is extended to add sequence complementary to the promoter sequence. See FIG. 3B, Step 15. The 3'-end of the promoter oligonucleotide is extended with the DNA polymerase to produce a fourth DNA primer extension product complementary to the third DNA primer extension product. See FIG. 3B, Step 16. Multiple copies of a second RNA product complementary to the third DNA primer extension product, not including the promoter portion, are transcribed from the double-stranded promoter and re-enter the amplification cycle at Step 9 of FIG. 3B. The base sequence of the second RNA product is substantially identical to the base sequence of the tag sequence and complement of the target sequence.

Figure 5:
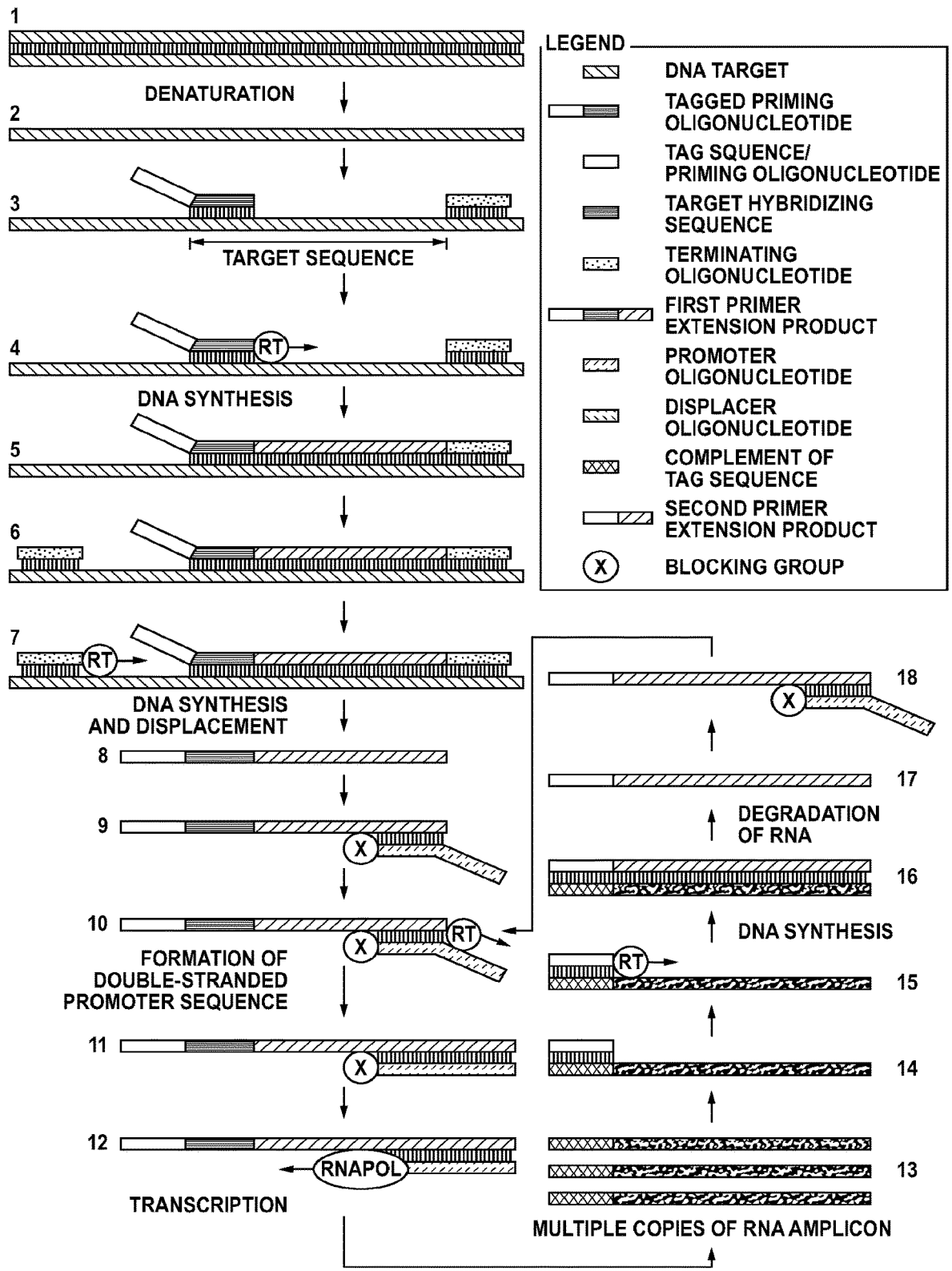
Figure 6:
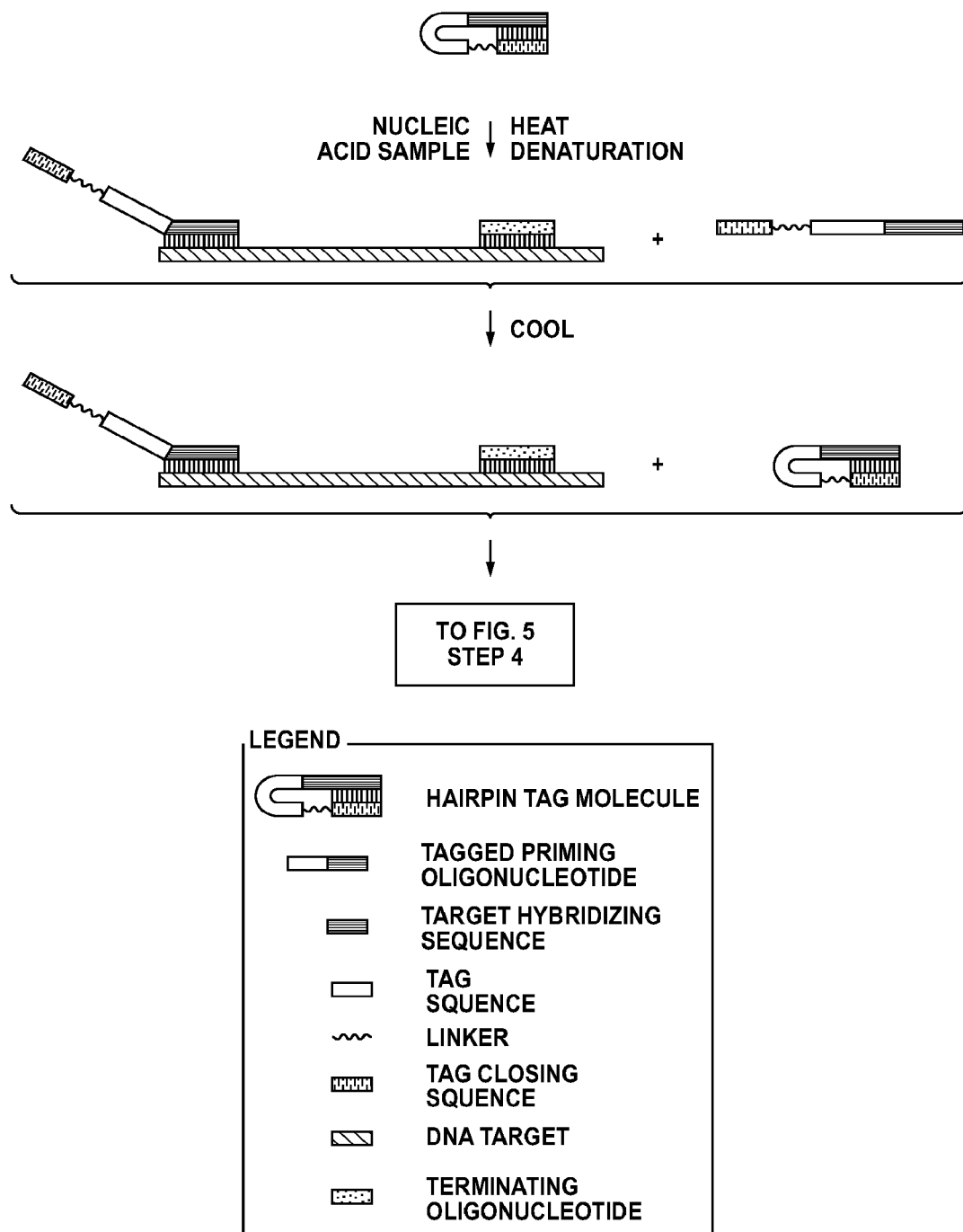

FIG. 5 illustrates an adaptation of an rTMA amplification reaction for amplifying a DNA target sequence, various aspects of which are disclosed in Becker et al., U.S. Pub. No. U.S. 2007-0202523 A1. The reaction of this illustrative embodiment is initiated by treating a DNA target sequence in a nucleic acid sample with a tagged priming oligonucleotide and a terminating oligonucleotide. The tagged priming oligonucleotide includes a target hybridizing sequence hybridized to a 3'-end of the target sequence and a tag sequence situated 5' to the target hybridizing sequence. The target hybridizing sequence preferably hybridizes to a single-stranded form of the target sequence, although it may hybridize to a double-stranded form of the target sequence through strand invasion, which can be facilitated by, for example, DNA breathing (e.g., AT rich regions), low salt conditions, and/or the use of DMSO and/or osmolytes, such as betaine. The target sequence is preferably rendered single-stranded by heating the nucleic acid sample. The terminating oligonucleotide hybridizes to a region of a target nucleic acid containing the target sequence in the vicinity of the 5'-end of the target sequence. The terminating oligonucleotide is used to end primer extension of a nascent nucleic acid that includes the tagged priming oligonucleotide. Thus, the target nucleic acid forms a stable complex with the tagged priming oligonucleotide at the 3'-end of the target sequence and the terminating oligonucleotide located adjacent to or near the 5'-end of the target sequence. See FIG. 5, Steps 1-3. Unhybridized tagged priming oligonucleotide is made unavailable for hybridization to the target sequence prior to initiating a primer extension reaction with the tagged priming oligonucleotide. An extension reaction is then initiated from the 3'-end of the tagged priming oligonucleotide with a DNA polymerase, e.g., reverse transcriptase, to produce a first DNA primer extension product that includes the tag sequence and a region complementary to the target sequence. See FIG. 5, Steps 4 and 5.

The nucleic acid sample is further treated with a displacer oligonucleotide that hybridizes to the target nucleic acid upstream from the tagged oligonucleotide such that a primer extension reaction can be initiated therefrom, so that the first DNA primer extension product is displaced when the DNA polymerase extends a 3'-end of the displacer oligonucleotide. See FIG. 5, Steps 6-8. The order of the illustrated steps is not meant to imply that the nucleic acid sample of this embodiment must be treated with the tagged priming oligonucleotide before it is treated with the displacer oligonucleotide to be operational. In certain embodiments, it is preferable to have these two oligonucleotides hybridize to the target nucleic acid substantially simultaneously.

Next, the first DNA primer extension product is treated with a promoter oligonucleotide having a hybridizing sequence and a promoter for an RNA polymerase situated 5' to the hybridizing sequence. The hybridizing sequence hybridizes to a region of the first DNA primer extension product that is complementary to the 3'-end of the target sequence, thereby forming a promoter oligonucleotide:first DNA primer extension product hybrid. In the illustrated reaction, the promoter oligonucleotide is modified to prevent the initiation of DNA synthesis by situating a blocking moiety at the 3'-end of the promoter oligonucleotide (e.g., nucleotide sequence having a 3'-to-5' orientation). See FIG. 5, Step 9. The 3'-end of the first DNA primer extension product is extended to add sequences complementary to the promoter, resulting in the formation of a double-stranded promoter sequence. See FIG. 5, Steps 10 and 11. Multiple copies of a first RNA product complementary to at least a portion of the first DNA primer extension product, not including the promoter, are transcribed using an RNA polymerase that recognizes the double-stranded promoter and initiates transcription therefrom. See FIG. 5, steps 12 and 13. As a result, the base sequence of the first RNA product is substantially identical to the target sequence and the complement tag sequence.

The first RNA products are contacted with a priming oligonucleotide that hybridizes to the complement of the tag sequence to form a priming oligonucleotide:first RNA product hybrid, and the 3'-end of the priming oligonucleotide is extended with the DNA polymerase to produce a second DNA primer extension product complementary to the first RNA product. See FIG. 5, steps 14-16. The second DNA primer extension product is separated from the first RNA product using and enzyme that selectively degrades the first RNA product (e.g., RNAse H activity). See FIG. 5, Step 17. The second DNA primer extension product is treated with the promoter oligonucleotide to form a promoter oligonucleotide:second DNA primer extension product hybrid. See FIG. 5, Step 18. The promoter oligonucleotide:second primer extension product hybrid then re-enters the amplification cycle at Step 10 of FIG. 5, where transcription is initiated from the double-stranded promoter and the cycle continues.

Figure 7:
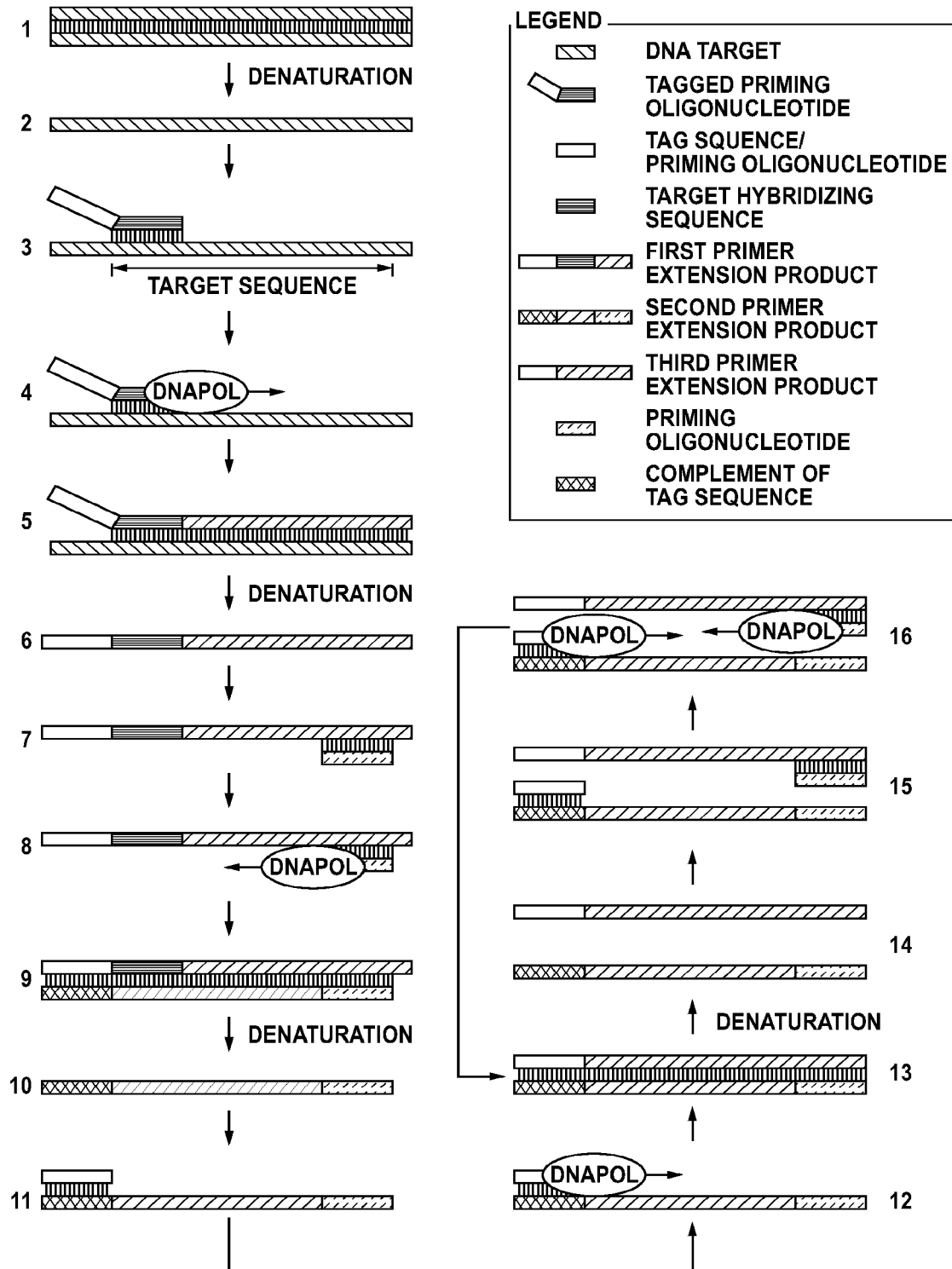
Figure 8:
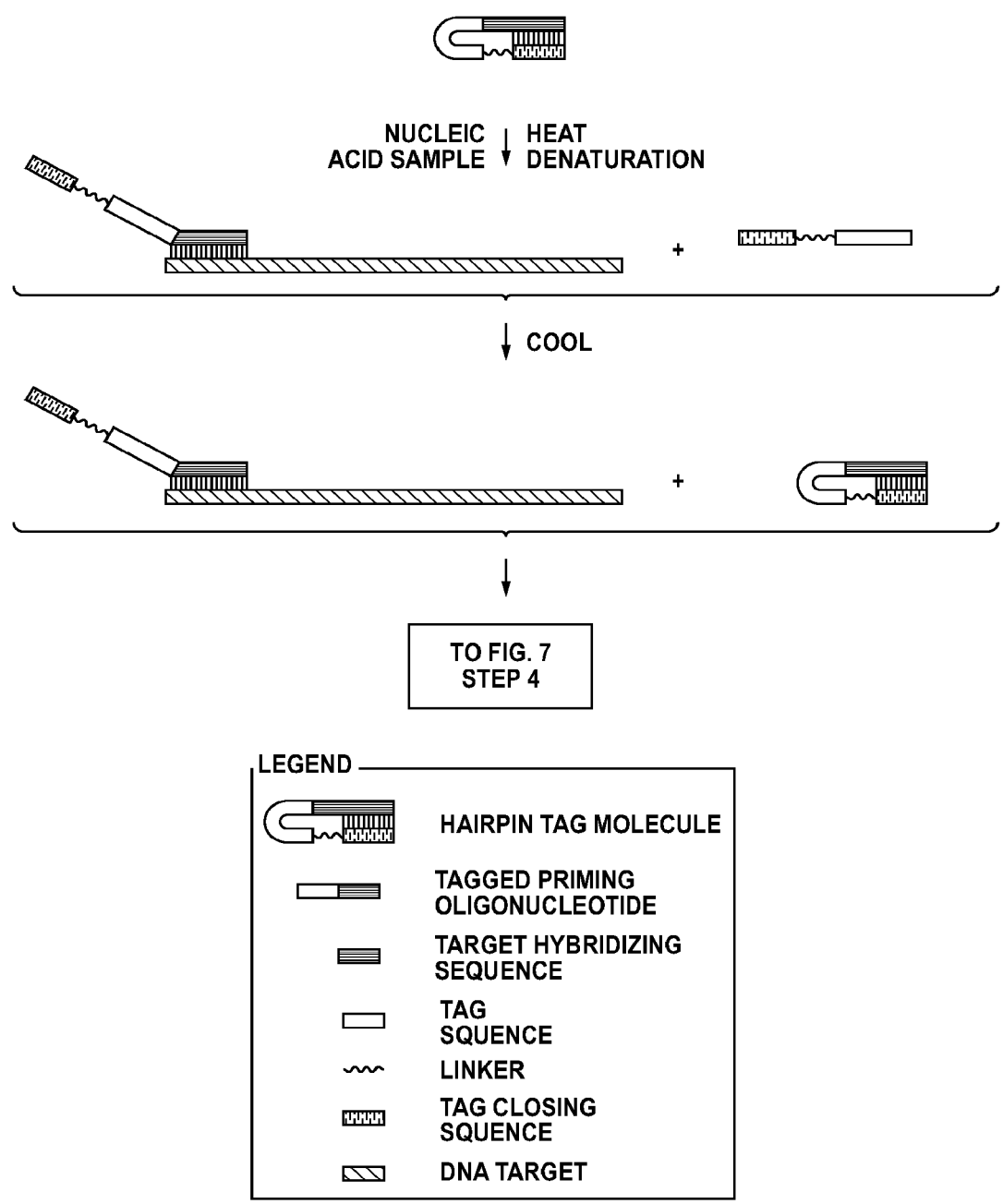

FIG. 7 illustrates an adaptation of a PCR. The reaction of this illustrative embodiment is initiated by treating a denatured DNA target sequence in a nucleic acid sample with a tagged priming oligonucleotide. The tagged priming oligonucleotide includes a target hybridizing sequence that hybridizes to a 3'-end of the target sequence and a tag sequence situated 5' to the target hybridizing sequence. Thus, the target sequence forms a stable complex with the tagged priming oligonucleotide at the 3'-end of the target sequence prior to initiating a primer extension reaction. See FIG. 7, Steps 1-3. Unhybridized tagged priming oligonucleotide is then made unavailable for hybridization to the target sequence. An extension reaction is initiated from the 3'-end of the tagged priming oligonucleotide with a DNA polymerase, e.g., Taq DNA polymerase, to produce a first DNA primer extension product that includes the tag sequence and a region complementary to the target sequence. See FIG. 7, Steps 4 and 5. Next, the double-stranded product resulting from the first primer extension reaction is denatured and the first DNA primer extension product is contacted with a first priming oligonucleotide that hybridizes to a region of the first DNA primer extension product that is complementary to the 5'-end of the target sequence. See FIG. 7, Steps 6 and 7.

In a second primer extension reaction, the 3'-end of the first priming oligonucleotide is extended with the DNA polymerase to produce a second DNA primer extension product that is complementary to a portion of the first primer extension product and includes the target sequence and the complement of the tag sequence. See FIG. 7, Steps 8 and 9. The double-stranded product resulting from the second primer extension reaction is denatured and the second DNA primer extension product is contacted with a second priming oligonucleotide that hybridizes to the complement of the tag sequence. See FIG. 7, Steps 10 and 11. The 3'-end of the second priming oligonucleotide is then extended in a third primer extension reaction with the DNA polymerase to produce a third DNA primer extension product that is complementary to the second DNA primer extension product. FIG. 7, Steps 12 and 13. The double-stranded product resulting from the third primer extension reaction is denatured and the second and third DNA primer extension products are available for participation in the repeated cycles of a polymerase chain reaction using as primers the first and second priming oligonucleotides. See FIG. 7, Steps 14-16.

Figure 9:
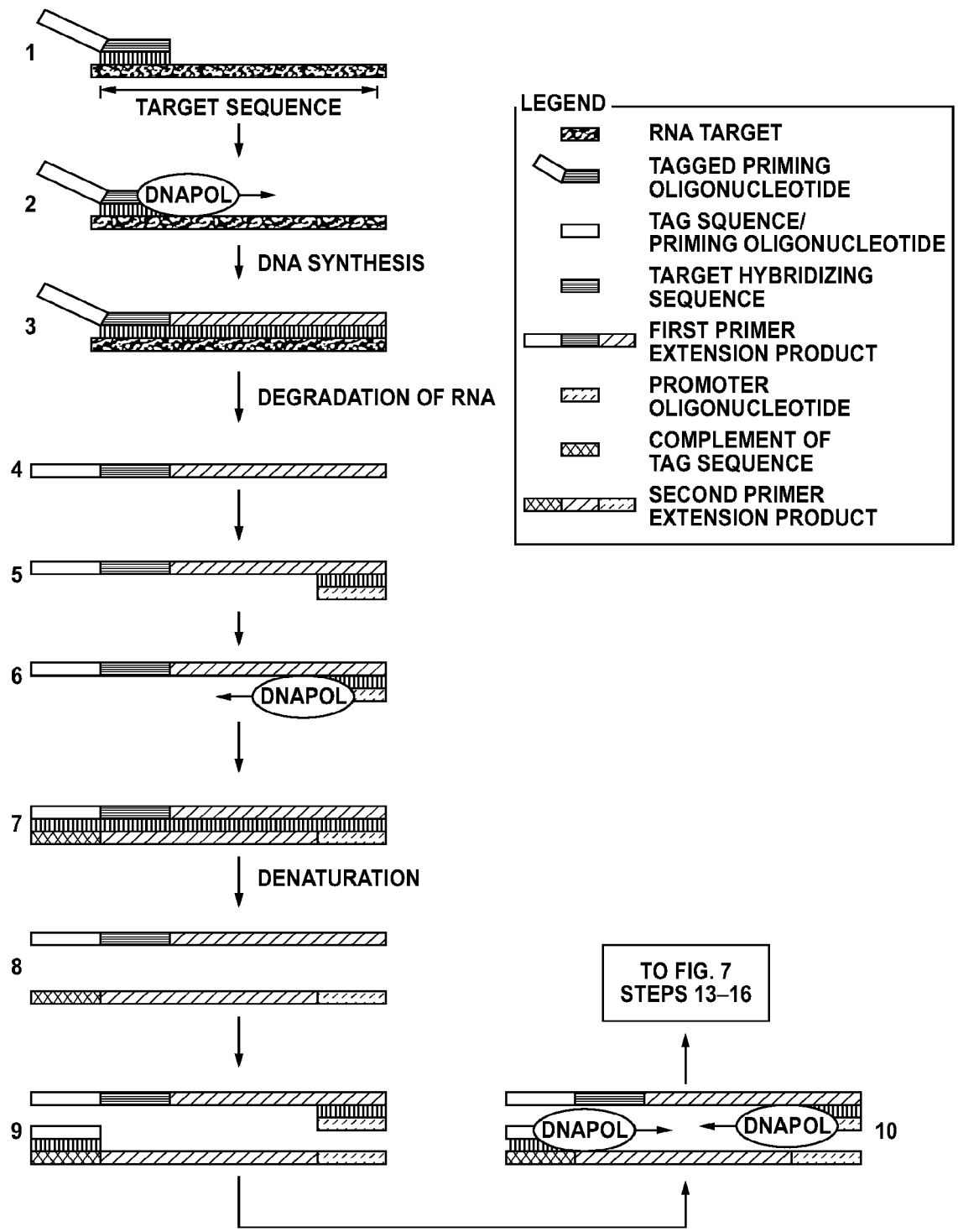
Figure 10:
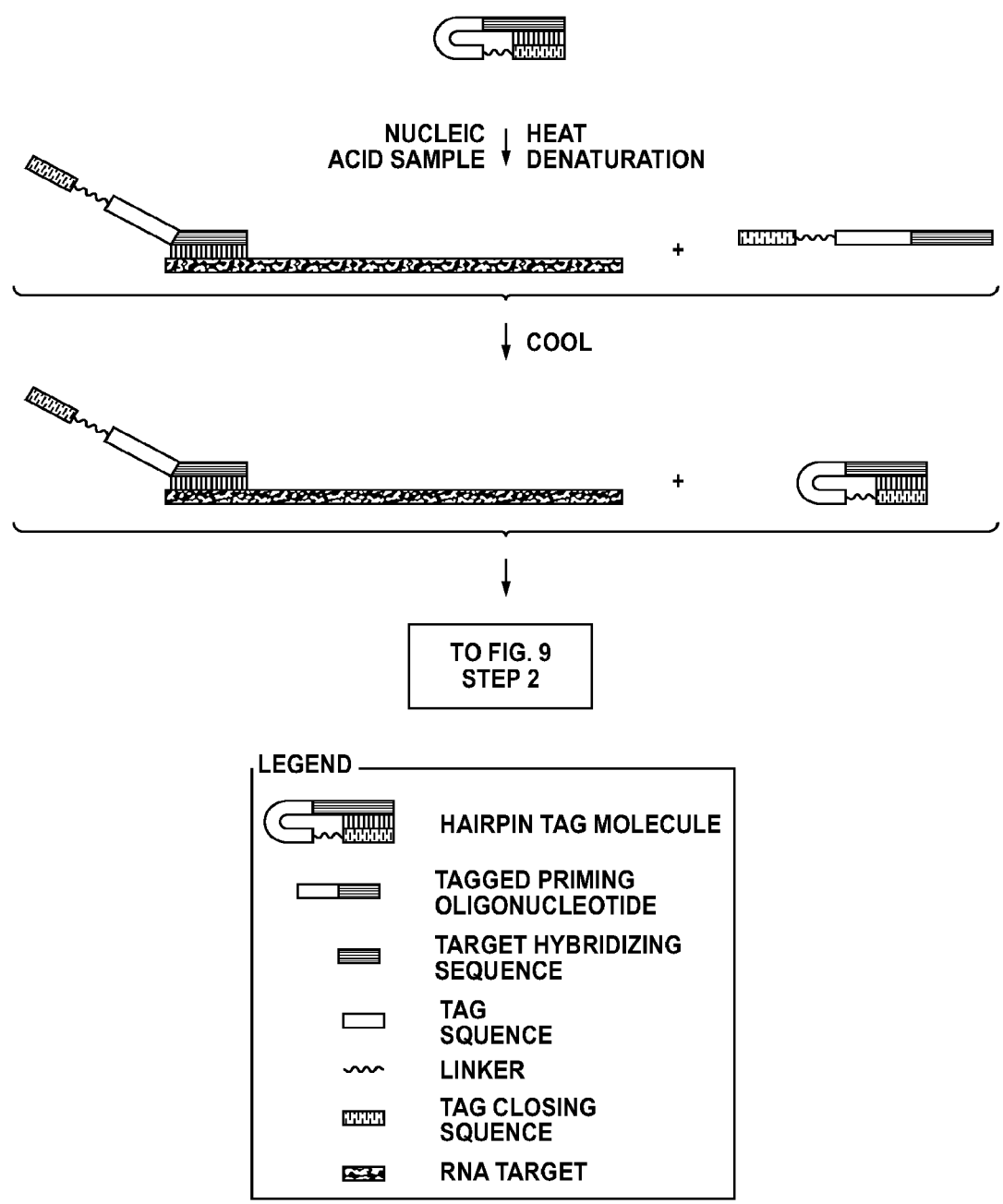

FIG. 9 illustrates an adaptation of RT-PCR. The reaction of this illustrative embodiment is initiated by treating an RNA target sequence in a nucleic acid sample with a tagged priming oligonucleotide. The tagged priming oligonucleotide includes a target hybridizing sequence and a tag sequence situated 5' to the target hybridizing sequence. Thus, the target sequence forms a stable complex with the tagged priming oligonucleotide at the 3'-end of the target sequence prior to initiating a primer extension reaction. See FIG. 9, Step 1. Unhybridized tagged priming oligonucleotide is made unavailable for hybridization to the target sequence. An extension reaction is then initiated from the 3'-end of the tagged priming oligonucleotide with a DNA polymerase, e.g., MasterAmp.sup.™ Tth DNA Polymerase, to produce a first DNA primer extension product that includes the tag sequence and a region complementary to the target sequence. See FIG. 9, Steps 2 and 3. The first DNA primer extension product is then separated from the target nucleic acid sequence to which it is hybridized using an enzyme that selectively degrades that portion of a target nucleic acid containing the target sequence that is complementary to the first DNA primer extension product (e.g., RNAse H activity). See FIG. 9, Step 4. Next, the first DNA primer extension product is treated with a first priming oligonucleotide that hybridizes to a region of the first DNA primer extension product that is complementary to the 5'-end of the target sequence to form a first DNA primer extension product:first priming oligonucleotide hybrid. See FIG. 9, Step 5. A second primer extension reaction extends the 3'-end of the first priming oligonucleotide with the DNA polymerase to produce a DNA second primer extension product complementary to at least a portion of the first primer extension product and includes the target sequence and the complement of the tag sequence. See FIG. 9, Steps 6 and 7. The first and second DNA primer extension products are then separated from each other by denaturation. See FIG. 9, Step 8. The first and second extension products are then available to participate in the repeated cycles of a polymerase chain reaction using as primers the first priming oligonucleotide and a second priming oligonucleotide which hybridizes to the complement of the tag sequence. See FIG. 9, Steps 9 and 10; FIG. 7, Steps 13-16.

Preferably for these amplification reactions, heterologous amplification oligomers that have not formed part of a tagged target nucleic acid sequence are inactivated prior to exposing the tagged target nucleic acid sequence to reagents and conditions sufficient for detectable amplification of a target nucleic acid sequence.

In addition to the methods described herein, the present invention is drawn to kits comprising one or more of the reagents required for carrying out the methods of the present invention. Kits comprising various components used in carrying out the present invention may be configured for use in any procedure requiring amplification of nucleic acid target molecules, and such kits can be customized for various different end-users. Suitable kits may be prepared, for example, for microbiological analysis, blood screening, disease diagnosis, water testing, product release or sterility testing, environmental or industrial analysis, food or beverage testing, or for general laboratory use. Kits of the present invention provide one or more of the components necessary to carry out nucleic acid amplifications according to the invention. Kits may include reagents suitable for amplifying nucleic acids from one particular target or may include reagents suitable for amplifying multiple targets. Kits of the present invention may further provide reagents for real-time detection of one or more nucleic acid targets in a single sample, for example, one or more self-hybridizing probes as described above. Kits may comprise a carrier that may be compartmentalized to receive in close confinement one or more containers such as vials, test tubes, wells, and the like. Preferably at least one of such containers contains one or more components or a mixture of components needed to perform the amplification methods of the present invention.

A kit according to one embodiment of the present invention can include, for example, in one or more containers, an inactivatable target capture oligomer of the current invention. Optionally, a kit may further comprise a heterologous amplification oligomer, a binding molecule or other means for terminating a primer extension reaction, and, optionally, an extender oligonucleotide and/or a capping oligonucleotide. If real-time detection is used, the one or more containers may include one or more reagents for real-time detection of at least one nucleic acid target sequence in a single sample, for example, one or more self-hybridizing probes as described above. Another container may contain an enzyme reagent, such as a heat stable DNA polymerase for performing a PCR or RT-PCR reaction, or a mixture of a reverse transcriptase (either with or without RNAse H activity), an RNA polymerase, and optionally an additional selective RNAse enzyme for a transcription-based amplification reaction. These enzymes may be provided in concentrated form or at working concentration, usually in a form that promotes enzyme stability. The enzyme reagent may also be provided in a lyophilized form. See Shen et al., "Stabilized Enzyme Compositions for Nucleic Acid Amplification," U.S. Pat. No. 5,834,254. Another one or more containers may contain an amplification reagent in concentrated form, e.g., 10×, 50×, or 100×, or at working concentration. An amplification reagent will contain one or more of the components necessary to run the amplification reaction, e.g., a buffer, MgCl.sub.2, KCl, dNTPs, rNTPs, EDTA, stabilizing agents, etc. Certain of the components, e.g., MgCl.sub.2 and rNTPs, may be provided separately from the remaining components, allowing the end user to titrate these reagents to achieve more optimized amplification reactions. Another one or more containers may include reagents for detection of amplification products, including one or more labeled oligonucleotide probes. Probes may be labeled in a number of alternative ways, e.g., with radioactive isotopes, fluorescent labels, chemiluminescent labels, nuclear tags, bioluminescent labels, intercalating dyes, or enzyme labels. In some embodiments, a kit of the present invention will also include one or more containers containing one or more positive and negative control target nucleic acids which can be utilized in amplification experiments in order to validate the test amplifications carried out by the end user. In some instances, one or more of the reagents listed above may be combined with an internal control. Of course, it is also possible to combine one or more of these reagents in a single tube or other containers. Supports suitable for use with the invention, e.g., test tubes, multi-tube units, multi-well plates, etc., may also be supplied with kits of the invention. Finally a kit of the present invention may include one or more instruction manuals.

Kits of the invention may contain virtually any combination of the components set out above or described elsewhere herein. As one skilled in the art would recognize, the components supplied with kits of the invention will vary with the intended use for the kits, and the intended end user. Thus, kits may be specifically designed to perform various functions set out in this application and the components of such kits will vary accordingly.

The present invention is further drawn to various oligonucleotides including, for example, the target specific oligonucleotides exemplified below. It is to be understood that oligonucleotides of the present invention may be DNA, RNA, DNA:RNA chimerics and analogs thereof, and, in any case, the present invention includes RNA equivalents of DNA oligonucleotides and DNA equivalents of RNA oligonucleotides.

Detection probes of the present invention may include, for example, an acridinium ester label, or labeled, self-hybridizing regions flanking the sequence that hybridizes to the target sequence. In various embodiments, these labeled oligonucleotide probes optionally or preferably are synthesized to include at least one modified nucleotide, e.g., a 2'-O-ME ribonucleotide; or these labeled oligonucleotide probes optionally or preferably are synthesized entirely of modified nucleotides, e.g., 2'-O-ME ribonucleotides.

It will be understood by one of ordinary skill in the relevant arts that other suitable modifications and adaptations to the methods, compositions, reaction mixtures and kits described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Examples are provided below illustrating certain aspects and embodiments of the invention. The examples below are believed to accurately reflect the details of experiments actually performed, however, it is possible that some minor discrepancies may exist between the work actually performed and the experimental details set forth below which do not affect the conclusions of these experiments or the ability of skilled artisans to practice them. Skilled artisans will appreciate that these examples are not intended to limit the invention to the specific embodiments described therein. Additionally, those skilled in the art, using the techniques, materials and methods described herein, could easily devise and optimize alternative amplification systems for carrying out these and related methods while still being within the spirit and scope of the present invention.

Unless otherwise indicated, oligonucleotides and modified oligonucleotides in the following examples were synthesized using standard phosphoramidite chemistry, various methods of which are well known in the art. For example, using the Expedite.sup.™ 8909 DNA Synthesizer (PerSeptive Biosystems, Framingham, Mass.). See e.g., Carruthers et al. (1987) Meth. Enzymol. 154, 287. Unless otherwise stated herein, modified nucleotides were 2'-O-ME ribonucleotides, which were used in the synthesis as their phosphoramidite analogs. Reagents and protocol conditions used in the performed experiments, as well as a discussion of the results and conclusions of the experiments, are set forth below. The blocking moiety, if present, is at the 3'-end.

Example 1

Selective Hybridization and Capture of Target Nucleic Acids

In a first example, target capture was performed using a linear target capture oligomer and an inactivatable target capture oligomer. The oligomers are presented in Table 1, below. The target nucleic acid was a *P. acnes* 16S ribosomal nucleic acid. The sequence of this target nucleic acid is found at GenBank Accession No.: AB042288.1 gi:7707831, first seen at NCBI on May 5, 2000, with non-sequence updates on Jul. 22, 2002, Jan. 14, 2004 and Aug. 9, 2006, and is also SEQ ID NO:38 in the Sequence Listing. To determine the efficiency of these target capture oligomers, captured nucleic acids were assayed in a subsequent real-time reverse TMA reaction (See, e.g., U.S. Pat. Nos. 5,480,784 and 5,399,491.). Briefly, a series of preannealing mixtures was made at 150.micro.L volume and comprising 0.5M LiCl lysis buffer, one of the linear target capture oligomer or the inactivatable target capture oligomer SEQ ID NOS:32 or 26, respectively, (6 pM/rxn each); a nonT7 primer amplification oligomer SEQ ID NO:39 (2 pm/rxn); and a terminating oligomer SEQ ID NO:37 (2 pM/rxn). Here, the terminating oligomer comprised 2'-O-Me residues and both of the linear target capture oligomer and the inactivatable target capture oligomer comprised target hybridization regions comprising 2'-O-Me residues. Following a short initial incubation, 1×10.sup.4 copies of SEQ ID NO:38 was added to some wells as a positive control, and the remaining reaction wells contained 0 copies per reaction of SEQ ID NO:38 for negative controls and for challenge reactions. The reactions were then incubated for about 45 minutes at about 60.deg.C. followed by a 45 minute cool down at room temperature. Each reaction was then transferred to a microplate containing 50.micro.L of target capture reagent comprising a magnetic bead comprising an immobilized probe. Target capture reagent for the reaction designated as challenge reactions were spiked with either 1×10.sup.6 or 1×10.sup.7 copies of SEQ ID NO:38. Six replicates were run for each condition.

A target capture protocol was performed essentially as follows. Target capture reactions were slowly mixed for about 5 minutes and then the beads were collected and transferred to a first wash reaction. Captured beads were eluted into the first wash reaction, slowly mixed for about 5 minutes, and the captured and eluted into a second wash reaction. Second wash reactions were mixed; the beads were captured and then eluted into a real-time TMA reaction mix. This amplification mix comprised a T7 promoter provider SEQ ID NOS:33, detection probe SEQ ID NO:35 and a non-T7 amplification oligomer, SEQ ID NO:34, that hybridizes with the tag sequence of SEQ ID NO:39. In this example the detection probe comprised 2'-O-Me residues, a 5' fluorescein, a 3' Dabcyl and a spacer between residues 18 and 19. Components and conditions for reaction mixtures and incubation conditions are known in the art. The amplification reaction was a real time RTMA reaction: pre-incubation at 42.deg.C. for 5 minutes on a thermomixer (Eppendorf Cat. No. 5355 34511); add 10 enzyme reagent; shake for 1 minute; and incubate at 42.deg.C. Results are below.

TABLE 1

| SEQ ID NO: | Sequence 5' → 3' |
|---|---|
| 26 | GCUGAUAAGCCGCGAGUUAUCAGCtttaaaaaaaaaaaaaaaaaaaaaaaaaaaaaa |
| 32 | GCUGAUAAGCCGCGAGUtttaaaaaaaaaaaaaaaaaaaaaaaaaaaaaa |
| 33 | aatttaatacgactcactatagggagaCGAACGCTGGCGGCGTGCTTAACACATGC |
| 34 | GTGACCCAATGATCTAACA |
| 35 | cCAGGGCCUUUCCGUUCGccugg |
| 37 | AGCGUUCGUCCUGAGCC |
| 39 | gtgacccaatgatctaacagagcaccccacaaaagcag |

TABLE 2

| Condition | TTime (min) Avg | RFU Avg ∀SD |
|---|---|---|
| SEQ ID NO: 26 No target/no challenge | >60.0 | 0.031 ∀0.003 |
| SEQ ID NO: 26 1E4 target/no challenge | 19.5 | 0.293 ∀0.009 |
| SEQ ID NO: 26 No target/1E6 challenge | 24.89 | 0.281 ∀0.010 |
| SEQ ID NO: 26 No target/1E7 challenge | 21.27 | 0.286 ∀0.010 |
| SEQ ID NO: 32 No target/no challenge | 29.67 | 0.029 ∀0.002 |
| SEQ ID NO: 32 1E4 target/no challenge | 19.09 | 0.289 ∀0.009 |
| SEQ ID NO: 32 No target/1E6 challenge | 21.4 | 0.297 ∀0.008 |
| SEQ ID NO: 32 No target/1E7 challenge | 17.76 | 0.284 ∀0.021 |

Results using the linear target capture oligo SEQ ID NO:32, were positive and robust for all positive control reactions at 1×10.sup.4 copies of SEQ ID NO:38 per reaction with an Average TTime=19.1 minutes. Two of the six negative samples produced weakly positive results. All six of the negative samples challenged with 1×10.sup.6 copies per reaction of P. acnes RNA during the target capture incubation step produced positive and robust results, as did all six of the negative samples challenged with 1×10.sup.7 copies per reaction of P. acnes RNA during the target capture incubation step. Thus, the linear target capture oligo was very susceptible to contaminating nucleic acids present in the target capture step. Results for the inactivatable target capture oligomer gave positive and robust results for 1×10.sup.4 copies of P. acnes (Average TTime=19.5 minutes). No positive amp activity was detected for the six negative samples. Here too were all six of the negative samples challenged with 1×10.sup.6 copies per reaction and all six of the negative samples challenged with 1×10.sup.7 copies per reaction of P. acnes RNA positive. However, the results from the challenge reactions were not as robust in the presence of the inactivatable target capture oligomer as they were in the presence of the linear target capture oligomer. Thus, the inactivatable target capture oligomer reaction wells discriminated surprisingly well against contaminating nucleic acids in the target capture reagent better than did the linear amplification oligomer; even when the contaminating nucleic acids are identical to the target nucleic acid.

Example 2

Selective Hybridization and Capture of Target Nucleic Acids and Amplification with Heterologous Amplification Oligomers A second set of experiments was conducted to compare the use of an inactivatable target capture oligomer to the use of a linear target capture oligomer; each along with a downstream amplification assay that uses a heterologous amplification oligomer. Amplification assays using heterologous amplification oligomers are described herein and are also known in the art (e.g., Becker et al., U.S. Pub. No. 2007-0281317 A1). Preannealing reactions were set up generally as described above for example 1. Oligomers used in the preannealing mixture were one of the linear target capture oligomer or the inactivatable target capture oligomer SEQ ID NOS:32 or 26, respectively, (6 pM/rxn each); a heterologous amplification oligomer SEQ ID NO:36 (2 pm/rxn); and a terminating oligomer SEQ ID NO:37 (2 pM/rxn). Following a short initial incubation, 1×10.sup.4 copies of SEQ ID NO:38 was added to some wells as a positive control, and the remaining reaction wells contained 0 copies per reaction of SEQ ID NO:38 for negative controls and for challenge reactions. The reactions were then incubated for about 45 minutes at about 60.deg.C. followed by a 45 minute cool down at room temperature. Each reaction was then transferred to a microplate containing 50.micro.L of target capture reagent comprising a magnetic bead comprising an immobilized probe. Target capture reagent for the reaction designated as challenge reactions were spiked with either 1×10.sup.6 or 1×10.sup.7 copies of SEQ ID NO:38. Six replicates were run for each condition.

A target capture protocol was performed essentially as follows. Target capture reactions were slowly mixed for about 5 minutes and then the beads were collected and transferred to a first wash reaction. Captured beads were eluted into the first wash reaction, slowly mixed for about 5 minutes, and the captured and eluted into a second wash reaction. Second wash reactions were mixed; the beads were captured and then eluted into a real-time TMA reaction mix. This amplification mix comprised a T7 promoter provider SEQ ID NOS:33, an amplification oligomer comprising a target hybridizing region that stably hybridizes the tag sequence of SEQ ID NO:36, that amplification oligomer being SEQ ID NO:34 and detection probe SEQ ID NO:35. Components and conditions for reaction mixtures and incubation conditions are known in the art. The amplification reaction was a real time RTMA reaction: pre-incubation at 42.deg.C. for 5 minutes on a thermomixer (Eppendorf Cat. No. 5355 34511); add 10 enzyme reagent; shake for 1 minute; and incubate at 42.deg.C. Results are below.

TABLE 3

| SEQ ID NO: | Sequence 5' → 3' |
|---|---|
| 26 | GCUGAUAAGCCGCGAGUUAUCAGCtttaaaaaaaaaaaaaaaaaaaaaaaaaaaaaa |
| 32 | GCUGAUAAGCCGCGAGUtttaaaaaaaaaaaaaaaaaaaaaaaaaaaaa |
| 33 | aatttaatacgactcactatagggagaCGAACGCTGGCGGCGTGCTTAACACATGC |
| 34 | GTGACCCAATGATCTAACA |
| 35 | cCAGGGCCUUUCCGUUCGccugg |
| 36 | CTGCTTTTGTGGGGGTGACCCAATGATCTAACACTCGAGCACCCCACAAAAGCAG |
| 37 | AGCGUUCGUCCUGAGCC |

TABLE 4

| Condition | TTime (min) Avg | RFU Avg ∀SD |
|---|---|---|
| SEQ ID NO: 26 No target/no challenge | >60.0 | 0.031 ∀0.001 |
| SEQ ID NO: 26 1E4 target/no challenge | 23.77 | 0.298 ∀0.003 |
| SEQ ID NO: 26 No target/1E6 challenge | 31.29 | 0.029 ∀0.002 |
| SEQ ID NO: 26 No target/1E7 challenge | 31.48 | 0.051 ∀0.017 |
| SEQ ID NO: 32 No target/no challenge | >60.0 | 0.031 ∀0.003 |
| SEQ ID NO: 32 1E4 target/no challenge | 22.39 | 0.291 ∀0.009 |
| SEQ ID NO: 32 No target/1E6 challenge | 31.01 | 0.196 ∀0.083 |
| SEQ ID NO: 32 No target/1E7 challenge | 25.39 | 0.286 ∀0.005 |

Results using the heterologous amplification oligomer SEQ ID NO:36 with the linear target capture oligo SEQ ID NO:32 were positive and robust for all positive control reactions at 1×10.sup.4 copies of SEQ ID NO:38 per reaction with an Average TTime=22.4 minutes. No positive amp activity was detected for the six negative samples. Five out of six of the negative samples challenged with 1×10.sup.6 copies per reaction of *P. acnes* RNA during the target capture incubation step produced weakly positive amplification results. All six of the negative samples challenged with 1×10.sup.7 copies per reaction of *P. acnes* RNA during the target capture incubation step produced positive amps.

Results using the heterologous amplification oligomer SEQ ID NO:36 along with the inactivatable target capture oligo SEQ ID NO:26 were positive and robust for all positive control reactions having 1×10.sup.4 copies per reaction of *P. acnes* RNA; Average TTime=23.8 minutes. No positive amp activity was detected for the six negative samples. One out of six of the negative samples challenged with 1×10.sup.6 copies per reaction of *P. acnes* RNA during the target capture incubation step produced a weakly positive amplification. All six of the negative samples challenged with 1×10.sup.7 copies per reaction of *P. acnes* RNA during the target capture incubation step produced no amplification activity. Thus, the inactivatable target capture oligomer when used in conjunction with a heterologous amplification oligomer produced robust results and discriminated surprisingly well against contaminating nucleic acids in the target capture reagent better than did the linear amplification oligomer; even when the contaminating nucleic acids are identical to the target nucleic acid.

Example 3

Inactivatable Target Capture Oligomers Comprising Tag-Closing Regions of Varying Length A series of amplification and detection reactions were set-up using either a linear target capture oligomer or an inactivatable target capture oligomer. The target organism was *P. acnes* and the target nucleic acid sequence was the 16S rRNA gene of *P. acnes*, SEQ ID NO:38. In a first set of experiments, inactivatable target capture oligomers were designed to comprise tag-closing regions that are complementary to a target hybridizing portion of the capture probe. The tag-closing regions were designed to vary from 6 contiguous nucleobases in length to 14 contiguous nucleobases in length. The inactivatable target capture oligomers also comprised a target hybridization region and a dT3A30 nucleic acid sequence binding pair member. In this first experiment, these various inactivatable target capture oligomers were compared against each other and against a linear target capture oligomer for their hybridization sensitivity towards SEQ ID NO:38. The linear target capture oligomer and the inactivatable target capture oligomers used in these experiments are illustrated in Table 5.

TABLE 5

| SEQ ID NO: | Sequence 5' → 3' |
|---|---|
| 25 | GCUGAUAAGCCGCGAGUAUCAGC[TAIL] |
| 26 | GCUGAUAAGCCGCGAGUUAUCAGC[TAIL] |
| 27 | GCUGAUAAGCCGCGAGUUUAUCAGC[TAIL] |
| 28 | GCUGAUAAGCCGCGAGUCUUAUCAGC[TAIL] |
| 29 | GCUGAUAAGCCGCGAGUGCUUAUCAGC[TAIL] |
| 30 | GCUGAUAAGCCGCGAGUCGGCUUAUCAGC[TAIL] |
| 31 | GCUGAUAAGCCGCGAGUCGCGGCUUAUCAGC[TAIL] |
| 32 | GCUGAUAAGCCGCGAGU[TAIL] |

In Table 5, the notation "[tail]" refers to the binding pair member that is a dT3A30 nucleic acid sequence. In the embodiment of the current example, the non-tail residues are all 2'-O-Me residues. Underlined residues are the nucleic acid residues comprising the tag-closing region, also referred to as a tag region, and which are configured to not form a stable hybridization complex with the target nucleic acid sequence, but which will stably hybridize with the a portion of the target hybridization region of the target capture oligomer, thereby forming a loop structure and inactivating the target capture oligomer from further target capture. The target hybridizing regions, tag-closing regions and tails (or target hybridizing region and tail for SEQ ID NO:32) are joined as contiguous nucleic acid sequences without non-nucleotide linkers.

In addition to one of the target capture oligomers listed in Table 5, oligomers used in these reactions included a terminating oligomer SEQ ID NO:37, a tagged primer oligomer SEQ ID NO:36, a primer oligomer that hybridizes the tag region of SEQ ID NO:36, that primer oligomer being SEQ ID NO:34, a promoter-based oligomer SEQ ID NO:33, and a detection probe oligomer SEQ ID NO:35. Preferably, SEQ ID NO:33 is blocked, thus it is a promoter provider. See, Table 6 illustrating these additional oligomers

TABLE 6

| SEQ ID NO: | Sequence 5' → 3' |
|---|---|
| 33 | aatttaatacgactcactatagggagaCGAACGCTGGCG GCGTGCTTAACACATGC |
| 34 | GTGACCCAATGATCTAACA |
| 35 | cCAGGGCCUUUCCGUUCGccugg |
| 36 | CTGCTTTTGTGGGGGTGACCCAATGATCTAACACTCGAG CACCCCACAAAAGCAG |
| 37 | AGCGUUCGUCCUGAGCC |

In Table 6, the lower case letters of SEQ ID NO:33 represent the promoter region; the lower case letters of SEQ ID NO:35 represent the stem forming region and the underlined letters of SEQ ID NO:36 represent the tag region. Further, SEQ ID NO:35 comprises 2'-O-Me residues, a 5' fluorescein at residue number 1, a spacer between residues 18 and 19, and a 3' dabcyl following residue number 23. SEQ ID NOS:33 and 37 are 3' blocked.

A series of preannealing mixtures were made at 150.micro.L volume and comprising 0.5M LiCl lysis buffer, SEQ ID NOS:36 and 37 (2 pM/rxn each) and one of SEQ ID NOS:25-32 (6 pM/rxn each). Each of these reaction conditions was combined with one or more of either 1×10.sup.3, 1×10.sup.4 or 1×10.sup.5 copies per reaction of *P. acnes* 16S ribosomal nucleic acid (SEQ ID NO:38). Negative control reactions were also made to include 0 copies per reaction of *P. acnes* target nucleic acid. A target capture protocol was performed essentially as follows. Target capture reactions were slowly mixed for about 5 minutes and then the beads were collected and transferred to a first wash reaction. Captured beads were eluted into the first wash reaction, slowly mixed for about 5 minutes, and the captured and eluted into a second wash reaction. Second wash reactions were mixed; the beads were captured and then eluted into a real-time rTMA reaction mix. This amplification mix comprised amplification oligomers SEQ ID NOS:33 and 34 and detection probe SEQ ID NO:35. Components and conditions for reaction mixtures and incubation conditions are known in the art (See, e.g., U.S. Pat. Nos. 5,480,784 and 5,399,491.) Results are presented in Table 7.

TABLE 7

| Condition | TTime (min) Avg | RFU Avg ∀SD |
|---|---|---|
| SEQ ID NO: 32 and 0 copies of SEQ ID NO: 38 | 28.64 | 0.202 ∀0.18815698 |
| SEQ ID NO: 32 and 1e4 copies of SEQ ID NO: 38 | 23.31 | 0.471083333 ∀0.032424461 |
| SEQ ID NO: 32 and 1e5 copies of SEQ ID NO: 38 | 22.55 | 0.50455 ∀0.027238998 |
| SEQ ID NO: 29 and 0 copies of SEQ ID NO: 38 | 28.03 | 0.023309091 ∀0.003551184 |
| SEQ ID NO: 29 and 1e4 copies of SEQ ID NO: 38 | 27.52 | 0.024325 ∀0.001703673 |
| SEQ ID NO: 29 and 1e5 copies of SEQ ID NO: 38 | 28.17 | 0.352683333 ∀0.078898046 |
| SEQ ID NO: 30 and 0 copies of SEQ ID NO: 38 | 27.19 | 0.025636364 ∀0.002111527 |

TABLE 7-continued

| Condition | TTime (min) Avg | RFU Avg ∀SD |
|---|---|---|
| SEQ ID NO: 30 and 1e4 copies of SEQ ID NO: 38 | 29.46 | 0.208833333 ∀0.164515102 |
| SEQ ID NO: 30 and 1e5 copies of SEQ ID NO: 38 | 28.90 | 0.40535 ∀0.069912882 |
| SEQ ID NO: 31 and 0 copies of SEQ ID NO: 38 | >60.0 | 0.025645455 ∀0.002715645 |
| SEQ ID NO: 31 and 1e4 copies of SEQ ID NO: 38 | 27.96 | 0.206666667 ∀0.195675994 |
| SEQ ID NO: 31 and 1e5 copies of SEQ ID NO: 38 | 29.88 | 0.142883333 ∀0.157650035 |
| SEQ ID NO: 25 and 0 copies of SEQ ID NO: 38 | >60.0 | 0.028166667 ∀0.001661507 |
| SEQ ID NO: 25 and 1e4 copies of SEQ ID NO: 38 | 26.78 | 0.21482 ∀0.003179029 |
| SEQ ID NO: 25 and 1e5 copies of SEQ ID NO: 38 | 24.10 | 0.2277 ∀0.011768602 |
| SEQ ID NO: 26 and 0 copies of SEQ ID NO: 38 | >60.0 | 0.031475 ∀0.002243105 |
| SEQ ID NO: 26 and 1e4 copies of SEQ ID NO: 38 | 27.38 | 0.4149 ∀0.026926769 |
| SEQ ID NO: 26 and 1e5 copies of SEQ ID NO: 38 | 24.04 | 0.408 ∀0.024519973 |
| SEQ ID NO: 27 and 0 copies of SEQ ID NO: 38 | 22.96 | 0.044113043 ∀0.003205153 |
| SEQ ID NO: 27 and 1e4 copies of SEQ ID NO: 38 | 26.59 | 0.603583333 ∀0.024796805 |
| SEQ ID NO: 27 and 1e5 copies of SEQ ID NO: 38 | 23.81 | 0.612841667 ∀0.029039173 |
| SEQ ID NO: 28 and 0 copies of SEQ ID NO: 38 | 12.76 | 0.046845833 ∀0.003918959 |
| SEQ ID NO: 28 and 1e4 copies of SEQ ID NO: 38 | 24.54 | 0.578190909 ∀0.020016966 |
| SEQ ID NO: 28 and 1e5 copies of SEQ ID NO: 38 | 22.49 | 0.595809091 ∀0.036150338 |

The results presented in Table 7 illustrate that the inactivatable target capture oligomers all had reduced background fluorescence when compared to that of the linear capture probe (compare the reaction wells for 0 copies of target nucleic acid). The samples with linear capture probe provided an average of 0.2 RFU. Samples with inactivatable target capture oligomers provided on average about 0.02 RFU for inactivatable target capture oligomers having longer tag-closing regions (e.g., 10 to 14 nucleobases in length) to about 0.04 RFU for those with shorter tag-closing regions (e.g., 7-9 nucleobases in length). The longer tag-closing regions also resulted in longer average TTimes than did the shorter tag-closing regions; compare, Table 7 results for inactivatable target capture oligomers comprising tag-closing regions of 10 to 14 nucleobases in length with inactivatable target capture oligomers comprising tag-closing regions of 6 to 9 nucleobases in length. Surprisingly, these results show no linear relationship between the length of the tag-closing region and the average TTime. Similarly, for the average RFUs, the inactivatable target capture oligomers comprising shorter tag-closing regions (6 to 9 nucleobases in length) provided higher average RFUs than did the inactivatable target capture oligomers comprising longer tag-closing regions (10 to 14 nucleobases in length). (See, Table 7). Again, there is surprisingly no linear relationship between the length of the tag region and the resultant data.

In a second set of reactions, the inactivatable target capture oligomers of SEQ ID NO:26 and the linear capture probe of SEQ ID NO:32 are used in a series of amplification reactions in the presence or absence of a challenge organism. The reactions were set up substantially as described above and comprised a terminating oligomer, a heterologous amplification oligomer, a T7 promoter provider oligomer, a primer targeting the tag sequence of the heterologous amplification oligomer and a detection probe oligomer of Table 6. The *P. acnes* target nucleic acid was SEQ ID NO:38. The challenge nucleic acid was also *P. acnes* SEQ ID NO:38. Preannealing reactions contained: either 1×10.sup.4 copies of target nucleic acid as a positive control or 0 copies of target nucleic acid; either 6 pM/reaction of linear target capture oligomer or 6 pM/reaction of inactivatable target capture oligomers; 2 pM/reaction of blocker oligomer; and 2 pM/reaction of heterologous amplification oligomer. A series of target capture reagent mixtures were made to include 1×10.sup.5; 1×10.sup.6 or 1×10.sup.7 copies of *P. acnes* challenge nucleic acid. Following the preannealing step, the preannealing reactions with 0 copies of target nucleic acid were combined with each one of the target capture mixtures. The positive control preannealing reaction mixture was combined with a target capture mixture containing 0 copies of challenge nucleic acid. A target capture incubation step was then performed on each reaction condition, followed by a wash step and then an amplification step. Amplification was TMA, as generally described herein. Results are shown in Table 8.

TABLE 8

| Condition | TTime Avg ∀SD | RFU Avg ∀SD |
|---|---|---|
| SEQ ID NO: 32 0 copies of challenge | >60.0 | 0.016466667 ∀0.003868161 |
| SEQ ID NO: 32 E4 copies of target | 21.83 | 0.435566667 ∀0.051765883 |
| SEQ ID NO: 32 E5 copies of challenge | >60.0 | 0.022641667 ∀0.005540669 |
| SEQ ID NO: 32 E6 copies of challenge | 36.61 | 0.024166667 ∀0.005970343 |
| SEQ ID NO: 32 E7 copies of challenge | 28.22 | 0.281641667 ∀0.138143604 |
| SEQ ID NO: 26 0 copies of challenge | >60.0 | 0.0159 ∀0.001649242 |
| SEQ ID NO: 26 E4 copies of target | 21.36 | 0.427 ∀0.034371645 |
| SEQ ID NO: 26 E5 copies of challenge | >60.0 | 0.021975 ∀0.004562719 |
| SEQ ID NO: 26 E6 copies of challenge | 21.99 | 0.020954545 ∀0.005131348 |
| SEQ ID NO: 26 E7 copies of challenge | 35.90 | 0.021488889 ∀0.003267432 |

These results indicate that the inactivatable target capture oligomer shows better resistance to challenge organism compared to the linear capture probe. For both probes, the negative control reaction conditions (0 copies of challenge and 0 copies of target) had negative RFU values. Positive control reaction conditions (0 copies challenge and 1×10.sup.4 target) had positive RFU values for both. The linear probe, though, showed positive RFU values for in the presence of challenge organism. With the exception of a single positive reaction well seen in the 1×10.sup.6 conditions, the inactivatable target capture oligomers did not show positive RFU values.

Example 4

Selective Amplification of HCV Using Tagged Oligonucleotides in a Real-Time TMA Reaction The following series of experiments were conducted to evaluate whether the use of a tagged oligonucleotide to modify a target nucleic acid sequence in a nucleic acid sample of interest prior to a transcription-mediated amplification reaction would permit the selective amplification of target nucleic acid sequence contributed by the nucleic acid sample of interest, while not amplifying target nucleic acid sequence contributed by sources other than the nucleic acid sample of interest.

TABLE 9

Oligonucleotides

| SEQ ID NO: | Sequence 5' → 3' | Comment |
|---|---|---|
| 1 | GTTTGTATGTCTGTTGCTATTA TGTCTACAGGCATTGAGCGGGT TGATCCAAGAAAGGAC | Tagged Oligomer. 12 pM/rxn |
| 2 | GTTTGTATGTCTGTTGCTATTA T | Priming Oligomer. 12 pM/rxn |
| 3 | ATTTAATACGACTCACTATAGG GAGACCACAACGGTTTCTAGCC ATGGCGTTAGTATGAG-blocking moiety | Promoter Oligomer 12 pM/rxn |
| 4 | AmUmGmGmCmUmAmGmAmCmGm CmUmUmUmCmUmGmCmGmUmGm AmAmGmAm-blocking moiety | Terminating Oligomer m = 2'-Ome 0.8 pM/rxn |
| 5 | TGTCGTGCAGCCTCCAGGACCC CCCCTCCCGGGAGAGCCATA-blocking moiety | Extending Oligomer. 12 pM/rxn |
| 6 | GmGmGmCmAmCmUmCmGmCmAm AmGmCmAmmCmCmCmUmTTTAA AAAAAAAAAAAAAAAAAAAAA AAAAAA | Linear capture Probe 3 pM/rxn. m = 2'Ome |
| 7 | CmAmUmGmGmUmGmCmAmCmGm GmUmCmUmAmCmGmTTTAAAAA AAAAAAAAAAAAAAAAAAAAAA AAA | Linear capture Probe 3 pM/rxn. m = 2'Ome |
| 8 | [1]CmGmUmUmCmCmGmCmAmGmA mCmCmAmCmUmAmUm[2]GmAmAm CmGm[3] | Detection Probe. 4 pM/rxn m = 2'-Ome |

Blocking Moiety: A 3'-to-3' linkage prepared using 3'-dimethyltrityl-N-benzoyl-2'-deoxycytidine, 5'-succinoyl-long chain alkylamino-CPG (Glen Research Corporation, Sterling, Va.; Cat. No. 20-0102-01). 1=6-Carboxyfluorescein (FAM or fluorescein) (BioGenex, San Ramon, Calif.; Cat. No. BGX-3008-01); 2=9-O-Dimethoxytrityl-triethylene glycol, 1-[(2-cyanoethyl)-(N,N-diisopropyl)]-phosphoramidite (C9 linker) (Glen Research Corporation, Sterling, Va.; Cat. No. 10-1909-90); and 3=4-(4'-dimethylaminophenylazo) benzoic acid (DABCYL) (Prime Synthesis, Inc., Aston, Pa.).

Reagents and Other Protocol Information. Amplification Reagent. The "Amplification Reagent" or "AMP Reagent" comprised 11.6 mM Trizma® base buffer, 15 mM Trizma® hydrochloride buffer, 25 mM MgCl.sub.2, 23.3 mM KCl.sub.2, 3.33% (v/v) glycerol, 0.05 mM zinc acetate, 0.76 mM dATP, 0.76 mM dCTP, 0.76 mM dGTP, 0.76 mM dTTP, 0.02% (v/v) ProClin 300 Preservative (Supelco, Bellefonte, Pa.; Cat. No. 48126), 6.0 mM ATP, 6.0 mM CTP, 6.0 mM GTP, and 6.0 mM UTP, pH 7.81 to 8.0 at 22.deg.C. Enzyme Reagent. The "Enzyme Reagent" comprised 70 mM N-acetyl-L-cysteine, 10% (v/v) TRITON.sup.® X-102 detergent, 16 mM HEPES, 3 mM EDTA, 0.05% (w/v) sodium azide, 20 mM Trizma.sup.® base buffer, 50 mM KCl.sub.2, 20% (v/v) glycerol, 165.6 mM trehalose, pH 7, and containing 224 RTU/.micro.L Moloney murine leukemia virus ("MMLV") reverse transcriptase and 140 U/.micro.L T7 RNA polymerase, where one unit (i.e., RTU or U) of activity is defined as the synthesis and release of 5.75 fmol cDNA in 15 minutes at 37.deg.C. for MMLV reverse transcriptase, and the production of 5.0 fmol RNA transcript in 20 minutes at 37.deg.C. for T7 RNA polymerase. Wash Solution. The "Wash Solution" comprised 10 mM HEPES, 6.5 mM NaOH, 1 mM EDTA, 0.3% (v/v) ethyl alcohol, 0.02% (w/v) methyl paraben, 0.01% (w/v) propyl paraben, 150 mM NaCl, and 0.1% (w/v) sodium dodecyl sulfate, pH 7.5. Transport Medium. The "Transport Medium" comprised 150 mM HEPES, 8% (w/v) lithium lauryl sulfate, and 100 mM ammonium sulfate, pH 7.5. Target Capture Reagent. The "Target Capture Reagent" or "TCR" comprised the components listed below. Additional information about the formulation of this mixture is described below under Target Capture Reagent Procedure (IIIA). The concentrations listed represent the final concentrations of the components after having been combined with the magnetic particle solution. The magnetic particles were Sera-Mag.sup.™ MG-CM Carboxylate Modified (Seradyn, Inc., Indianapolis, Ind.; Cat. No. 24152105-050250), 1 micron, super-paramagnetic particles covalently bound 5'-amino modified oligo(dT).sub.14. The HEPES, lithium hydroxide, lithium chloride, EDTA, lithium lauryl sulfate and ammonium sulfate components were introduced with the TCR diluent and Transport Medium. First Capture Probe; 15.0 nM; Second Capture Probe; 15.0 nM; Tagged Priming Oligonucleotide; 60.0 nM; Terminating Oligonucleotide; 4.0 nM; HEPES, Free Acid, Dihydrate; 118.7 mM; Lithium Hydroxide, Monohydrate; 98.9 mM; Lithium Chloride, High Purity; 470.6 mM; EDTA, Free Acid; 25.0 mM; Lithium Lauryl Sulfate; 110.2 mM; Ammonium Sulfate; 37.5 mM; and Seradyn Poly dT14 Magnetic Particles; 0.075.micro.g/uL. Transcript Buffer. The "Transcript Buffer" comprised 0.2% lithium lauryl sulfate. Transcript Used. HCV Transcript. Product Numbers of Certain Materials or Equipment Used. KingFisher.sup.™ Plate (Thermo Labsystems, Franklin, Mass.; Cat. No. 97002540); MJ Research microtiter plate (Bio-Rad Laboratories, Inc., Hercules, Calif.; Cat. No. HSP-9665); Solo HT Incubator (Thermo Labsystems, Franklin, Mass.; Cat. No. 5161580); KingFisher.sup.™ Comb (Thermo Labsystems, Franklin, Mass.; Cat. No. 97002510); Eppendorf.sup.® Thermomixer R (Eppendorf North America; Westbury, N.Y.; Cat. No. 022670107 or 022670158)' and DNA Engine Opticon.sup.® 2 Real-Time PCR Detection System (Bio-Rad Laboratories, Inc., Hercules, Calif.; Cat. No. CFB-3220).

Additional Protocol Information. For the described experiments, 3.3.micro.L of target-containing transcript buffer was added to each 2.0 ml microtube in step B6 below. The tagged priming oligonucleotide and the terminating oligonucleotide were in water before being added to the 2.0 mL microtubes. Samples were vortexed for about 5 seconds. Incubating for 10 minutes at 60.deg.C. was found to be generally sufficient to capture the transcript. The plates were kept at room temperature for 5 minutes following the 10-minute incubation to allow the plates to cool before the target capture steps. This is also where the plates were transferred from the Solo HT Incubator to the KingFisher System. The speed of the thermomixer was 1400 rpm.

Target Capture Protocol: Target Capture Reagent (TCR) Procedure. Magnetic beads were slowly mixed at room temperature (RT) for 45 minutes and 150.micro.L magnetic beads were added to 5 mL TCR diluent (15.micro.g beads/ rxn when 50.micro.L used per sample). The solution was slowly mixed at room temperature for 35-minutes, at which time capture probe was added to 5 mL of the TCR diluent (to a final concentration of 0.12 pmol/.micro.L (6-pmol/50.micro.L rxn). Sample Preparation: AMP Reagent was prepared containing the promoter oligonucleotide, extender oligonucleotide and priming oligonucleotide (volume=1,600.micro.L). The solution was vortexed and placed at 2-8.deg.C. until needed. Detection probe was prepared in Enzyme Reagent and placed at 2-8.deg.C. until needed. Target dilutions were prepared in 0.2% LLS. 50.micro.L TCR was transferred into 200.micro.L microplate wells. Each target copy level, tagged priming oligonucleotide and terminating oligonucleotide were added to 1.2 mL 50% Transport Medium, 50% $H_2O$ in 2.0 mL microtubes. Target samples were vortexted and 150.micro.L transferred into 200.micro.L microplate (Plate 1) well containing 50.micro.L TCR (each well contained zero or 1 million copies HCV transcript plus appropriate amounts of tagged priming and terminating oligonucleotides).

Target Capture Protocol. The 200.micro.L microplate (Plate 1) was incubated at 60.deg.C. for 10 minutes using Labsystems Solo HT Incubator (Plate 1), and the microplate was then placed at RT for 5 minutes (Plate 1). 200.micro.L microplates (Plates 2 & 3) were prepared with 200.micro.L Wash Reagent. Amplification plate (Plate 4-MJ research 96 well microtiter plate) was prepared with 30.micro.L AMP Reagent per well. The 96 well comb was placed into Plate 1. All four plates were loaded into the KingFisher 96 unit and the target capture protocol was initiated, as follows. Plate 1 was mixed for 5 minutes at very slow speed and beads were collected for 12 counts and then released into Plate 2 for 10 seconds using slow speed. Plate 1 was then mixed for 1 second using very slow speed, beads collected for 12 counts, and the beads were released into Plate 2 for 10 seconds using slow speed. Plate 2 was mixed for 30 seconds at medium speed and beads were collected for 12 counts and then released into Plate 3 for 10 seconds using very slow speed. Plate 2 was then mixed for 1 second at very slow speed and beads were collected for 12 counts and released into Plate 3 for 10 seconds using very slow speed. Plate 3 was mixed for 30 seconds at medium speed, beads were collected for 12 counts, and the beads were released into Plate 4 for 10 seconds using medium speed. Plate 3 was then mixed for 1 second at very slow speed, beads collected for 12 counts and released into plate 4 for 10 seconds using medium speed. The 96 well microtiter plate (Plate 4) was removed and transferred to the bench, covered with a sealing card, and placed in the DNA Engine Opticon.sup.® 2 Real-Time PCR Detection System (Bio-Rad Laboratories; Hercules, Calif.) ("real-time instrument"). Real Time TMA was performed as follows. The plate was incubated for 5 minutes at 42.deg.C. and then removed and placed on a 42.deg.C. thermomixer. Each reaction well received a 10.micro.L aliquot of the Enzyme Reagent. The microtiter plate was covered with an adhesive tape seal, shaken gently for 30 seconds on the thermomixer, and then placed into the real-time instrument at 42.deg.C., where real-time assay monitoring was commenced. TTime values, which served as indicators of the amount of amplicon synthesized, were determined from the monitored fluorescence signals. See Light et al., U.S. Pub. No. US 2006-0276972, paragraphs 506-549.

Results and Conclusion: Experiments were performed according to the procedures described above for detecting an HCV transcript (8 replicates). The TCR in each test contained the same tagged priming oligonucleotide. A target capture step was performed for binding HCV transcript and removing unhybridized tagged priming oligonucleotide and terminating oligonucleotide. After the target capture step, an AMP Reagent was contacted with the beads of the TCR, with the AMP Reagent containing a priming oligonucleotide specific for the complement of the tag sequence. No tagged priming oligonucleotide was included in this step. Eight tagged priming and terminating oligonucleotides spiked into the AMP Reagent was 7.2 minutes. The zero samples with target, terminating oligonucleotide and tagged priming oligonucleotide spiked into the AMP Reagent also produced robust amplification with an Average TTime=8.6 minutes (Table 9).

TABLE 9

TTime Summary (AvgTTimes & SDTTimes)

| Sample ID | Target Name | Target Amt | Total | RN1 | TN1 | Avg. TTime | SDT Time |
|---|---|---|---|---|---|---|---|
| 1 million target in TC-x6.0 | HCV | 1E6 | 8 | 7 | 8 | 6.3 | 0.11 |
| 1 million target in TC, tagged non-T7 primer & terminating oligonucleotide in amp-x6.0 | HCV | 1E6 | 8 | 8 | 8 | 7.2 | 0.20 |
| 1 million target in TC-x6.0 | HCV | 1E6 | 8 | 8 | 7 | 6.3 | 0.05 |
| Zero target in TC, 1 million targ in amp-x0.0 | HCV | 0.00 | 8 | 8 | 0 | N/A | N/A |
| Zero target in TC, 1 million target, tagged non-T7 primer & terminating oligonucleotide in amp-x0.0 | HCV | 0.00 | 8 | 8 | 8 | 8.6 | 0.21 |
| Zero target in TC-x0.0 | HCV | 0.00 | 8 | 8 | 0 | N/A | N/A | replicates were run for each condition. The detection probe was added via the Enzyme Reagent at 4 pmol per reaction. The HCV AMP Reagent contained 12 pmol promoter oligonucleotide, 12 pmol extender oligonucleotide and 12 pmol priming oligonucleotide per reaction.

Figure 17:
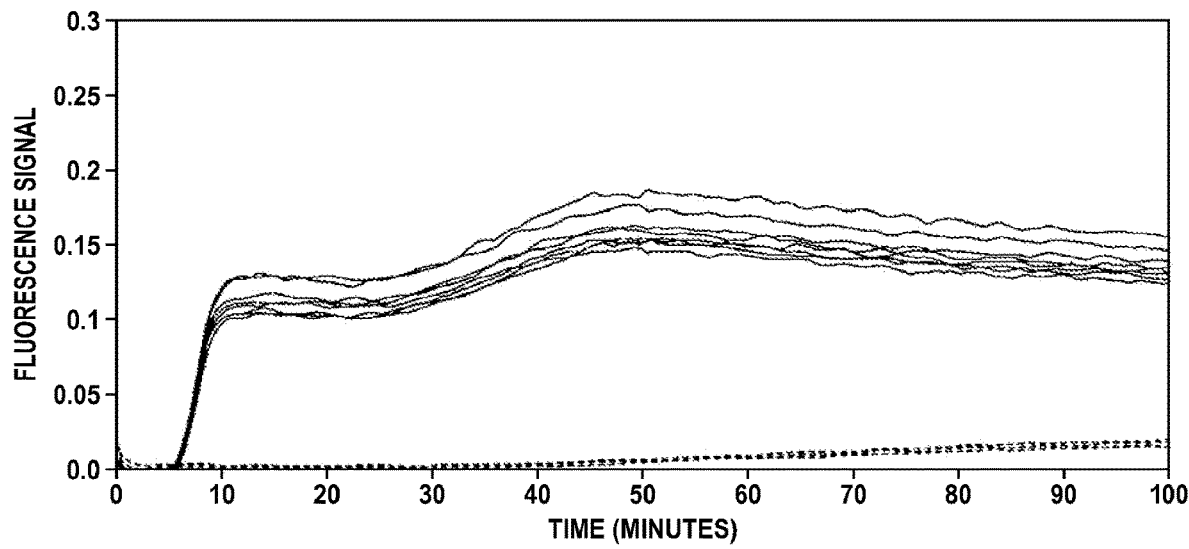
FIGS. 17 through 21 illustrate results from downstream analysis of selectively captured target nucleic acids, exemplifying that the compositions and methods of the current invention provide selective hybridization and capture of target nucleic acids from samples.

The first set of experiments compared the results of reactions in which no copies of the HCV transcript were spiked into the TCR or AMP Reagent with the results of reactions in which $1\times10^6$ copies of the HCV transcript were spiked into the TCR. FIG. 17 shows the raw curves for HCV amplifications in which no target was spiked into the AMP Reagent. There was no detectable amplification when the HCV transcript was not spiked into the TCR or AMP Reagent, while the average TTime for reactions containing $1\times10^6$ copies of the HCV transcript in the TCR was 6.3 minutes. The "TTime" values relate to time of emergence (time at which signal rises above background), and a summary of these values for the experiments performed is set forth in Table 1 below.

Figure 18:
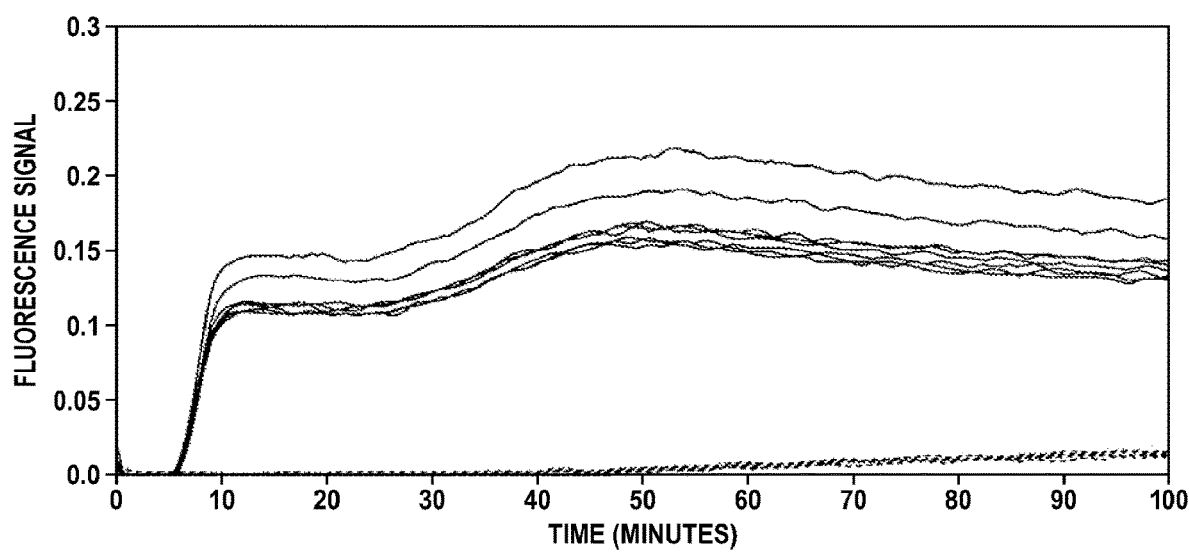

A second set of experiments compared the results of reactions in which $1\times10^6$ copies of the HCV transcript were spiked into the AMP Reagent only with reactions in which $1\times10^6$ copies of the HCV transcript were spiked into the TCR only. FIG. 18 shows the raw curves for HCV amplifications in which target was spiked into the AMP Reagent. There was no detectable amplification when the HCV transcript was spiked into the AMP Reagent, while the average TTime for reactions containing $1\times10^6$ copies of the HCV transcript in the TCR was 6.3 minutes (Table 1). The zero target in TC samples did not amplify, even with 1 million copies HCV transcript spiked into the AMP Reagent.

Figure 19:
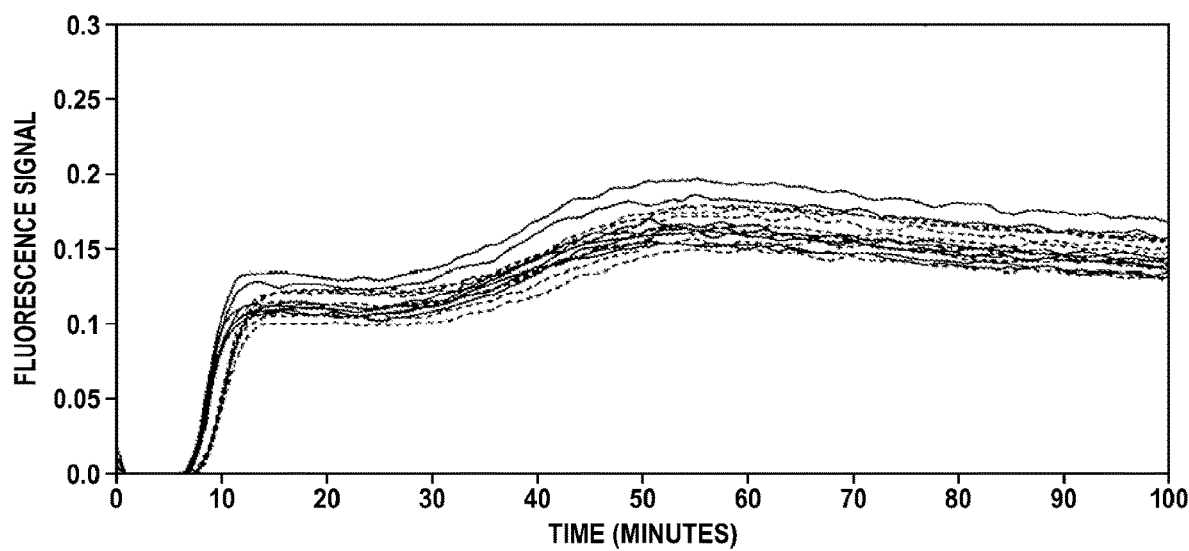

A third set of experiments compared the results of reactions in which $1\times10^6$ copies of the HCV transcript and the tagged priming oligonucleotide were provided in the AMP Reagent (no copies of the HCV transcript in TCR) with the results of reactions in which $1\times10^6$ copies of the HCV transcript were provided in the TCR and the tagged priming oligonucleotide was provided in the AMP Reagent. FIG. 19 shows that the Average TTime for 1 million copies HCV transcript present only in the target capture step with The results of these experiments demonstrate that only when the tagged priming oligonucleotide was present in the AMP Reagent along with the priming oligonucleotide did zero TCR samples amplify when 1 million copies of HCV transcript were spiked into the AMP Reagent. Thus, HCV transcript entering the system through the AMP Reagent is not amplified unless the tagged priming oligonucleotide is also provided with the AMP Reagent.

The preceding Example demonstrated how a tagged priming oligonucleotide that hybridized to an HCV template could be used for selectively detecting HCV nucleic acids in a sample of interest without interference from contaminating nucleic acid introduced subsequent to a target capture step. The following Example illustrates how a similar approach was used for detecting bacterial nucleic acids in a sample of interest despite the presence of contaminating templates in reagents used for performing the amplification reaction. Advantageously, non-complexed tagged priming oligonucleotide was substantially absent from the reaction mixture at the time a complex comprising the tagged priming oligonucleotide and the template contacted the DNA polymerase used in the amplification reaction.

Example 5 below describes two procedures for amplifying *E. coli* rRNA nucleic acids, where the procedures differed by the use of both a tagged priming oligonucleotide and target capture. The first procedure employed an *E. coli* specific non-tagged priming oligonucleotide in combination with a terminating oligonucleotide, a promoter oligonucleotide and a detection probe. The second procedure employed a tagged priming oligonucleotide having a target-complementary sequence identical to that contained in the *E. coli* specific non-tagged priming oligonucleotide of the first procedure, a tag-specific priming oligonucleotide, as well as a terminating oligonucleotide, a promoter oligonucleotide and a detection probe. The tag-specific priming oligonucleotide, which had a nucleotide sequence corresponding to a segment of HIV-1, hybridized to the complement of the tag sequence contained in the tagged priming oligonucleotide, but did not hybridize to the *E. coli* rRNA template nucleic acid or the complement thereof. In the case of the second procedure, the terminating oligonucleotide, the promoter oligonucleotide and the detection probe were identical to those used in the first procedure. As demonstrated below, amplification reactions that omitted the tagged priming oligonucleotide failed to discriminate between samples containing 0 and 1×10.sup.6 copies of a synthetic *E. coli* rRNA target. Conversely, the approach that included use of a tagged priming oligonucleotide and target capture clearly distinguished samples containing 0 and 1×10.sup.3 copies of the synthetic *E. coli* rRNA target.

Example 5

Use of a Tagged Priming Oligonucleotide Allows Discrimination Between Sample-Derived Templates and Exogenous Templates Amplification Using a Non-Tagged Priming Oligonucleotide without Target Capture In a first procedure, amplification reactions employing a synthetic *E. coli* rRNA template were performed using a non-tagged priming oligonucleotide that hybridized to the template, a promoter oligonucleotide, a terminating oligonucleotide and a molecular torch detection probe. Reactions were primed using the synthetic template added directly into the reaction mixtures (i.e., without undergoing target capture purification) at 0 or 1×10.sup.6 copies/reaction. A molecular torch detection probe was used to monitor amplicon production as a function of time. In the nucleotide sequences presented below, 2'-O-methyl ribose (2'-O-Me) modifications of the polynucleotide backbone are indicated by lower case "m." Blocking moieties at the 3' termini of the promoter oligonucleotide and terminating oligonucleotide comprised a 3'-to-3' linkage that was prepared using 3'-dimethyltrityl-N-benzoyl-2'-deoxycytidine, 5'-succinoyl-long chain alkylamino-CPG (Glen Research Corporation, Sterling, Va.; Cat. No. 20-0102-01). Oligonucleotides, reagents and essential methods used in the procedure were as follows.

TABLE 10

Oligonucleotides

| SEQ ID NO: | Sequence 5' → 3' | Comments |
| --- | --- | --- |
| 9 | CmUmGmCmTGGCACGGAGTTAGCCGGTGCTTC | Priming Oligomer. m = 2'Ome |
| 10 | ATTTAATACGACTCACTATAGGGAGAGAAGGCCTTCGGGTTGTAAAG-blocking moiety | Promoter Provider |
| 11 | GmCmCmUmUmCmUmCmCmAmUmAmCmAmCmGmCmGm-blocking moiety | Terminating Oligomer m = 2'Ome |
| 12 | ¹CmUmGmCmGmGmGmUmAmAmCmGmUmCmAmAmUmGmAmGmCmAmAmAm²CGCAG³ | Detection Probe 1 fluorescein 2 C9 linker 3 DABCYL |

Reagents and Other Protocol Information: Amplification and enzyme reagents were essentially as described under Example 4. Procedures using the non-tagged priming oligonucleotide that hybridized to the *E. coli* template did not employ target capture oligonucleotides or reagents, did not employ transport medium or wash solution, and did not employ an extender oligonucleotide.

Real-Time Amplification Protocol. Sample solutions were prepared using primerless amplification reagent, non-tagged priming oligonucleotide, promoter oligonucleotide, terminating oligonucleotide, detection probe and synthetic template nucleic acid. Each well of a 96-well microtiter plate received a 30.micro.L aliquot of the prepared sample solution. The microtiter plate was covered with an adhesive tape seal, incubated first for 10 minutes at 60.deg.C. in the DNA ENGINE OPTICON.sup.® 2 (Bio-Rad Laboratories; Hercules, Calif.) temperature-controlled real-time instrument, and then temperature-adjusted to 42.deg.C. for 5 minutes. Thereafter, the plate was removed from the real-time instrument and placed onto a 42.deg.C. thermomixer. Each reaction well received a 10.micro.L aliquot of the enzyme reagent. The microtiter plate was covered with an adhesive tape seal, shaken gently for 30 seconds on the thermomixer, and then placed into the real-time instrument at 42.deg.C. where real-time assay monitoring was commenced. TTime values, which served as indicators of the amount of amplicon synthesized, were determined from the monitored fluorescence signals.

Results and Conclusion

Figure 20:
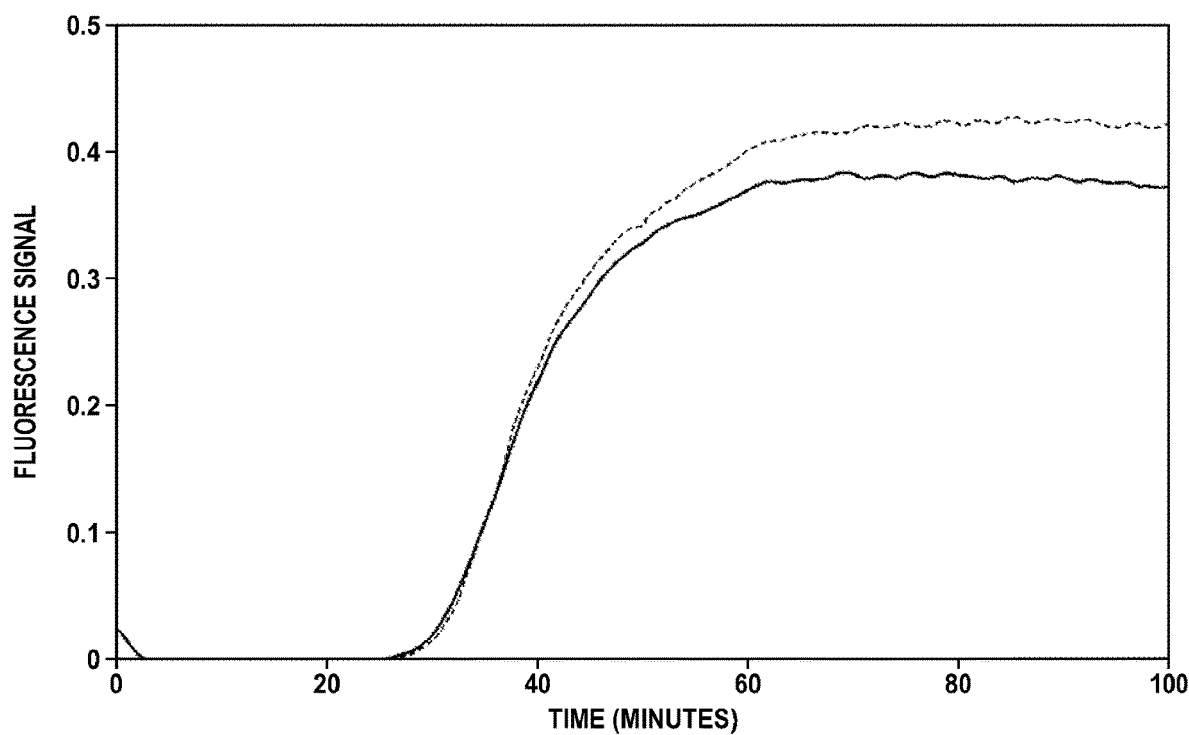

As indicated in FIG. 20, substantially identical results were observed in reactions that included either 0 or 1×10.sup.6 copies of the template nucleic acid, and so the assay showed no discrimination between these two conditions. More specifically, fluorescent signals indicating formation of *E. coli* nucleic acid amplification products emerged from background levels at substantially similar times (i.e., TTime=31.74 minutes at the 0 copy level, and 31.19 minutes at the 10.sup.6 copy level) in both reactions. Thus, a real-time amplification profile characteristic of high levels of the nucleic acid template was obtained even in the absence of added *E. coli* rRNA template. This was consistent with the presence of contaminating bacterial nucleic acid templates in one or more of the reagents used for carrying out the amplification reactions following the target capture procedure.

Amplification Using a Tagged Priming Oligonucleotide and Target Capture

In a second procedure, a tagged priming oligonucleotide and target capture step were employed for performing amplification reactions using test samples containing either 0, 103 or 105 copies of the synthetic *E. coli* transcript. Oligonucleotides used in the procedure are indicated below. The molecular torch detection probe was added as a component of the enzyme reagent. Following target capture, tagged priming oligonucleotide that was not hybridized to template nucleic acid was removed from the system by standard target capture and wash steps. The complex that included the rRNA template and the tagged priming oligonucleotide remained captured on super-paramagnetic particles. Amplification reactions were carried out using reagents essentially as described above, except for substitution of a non-specific target capture oligomer for the sequence-specific capture probes employed in Example 4. Amplification reactions were carried out in replicates of six and monitored using a molecular torch detection probe essentially as described in Example 4, except that an extender oligonucleotide was omitted. As above, 2'-O-methyl ribose (2'-O-Me) modifications of the polynucleotide backbone in the sequences presented below are indicated by lower case "m." Blocking moieties at the 3' termini of the promoter oligonucleotide and terminating oligonucleotide comprised a 3'-to-3' linkage that was prepared using 3'-dimethyltrityl-N-benzoyl-2'-deoxycytidine, 5'-succinoyl-long chain alkylamino-CPG (Glen Research Corporation, Sterling, Va.; Cat. No. 20-0102-01). Oligonucleotides, reagents and essential methods used in the procedure were as follows.

TABLE 10

Oligonucleotides

| SEQ ID NO: | Sequence 5' → 3' | Comments |
|---|---|---|
| 14 | GTTTGTATGTCTGTTGCTATTATG TCTACCTGCTGGCACGGAGTTAGC CGGTGCTTC | Tagged Primer |
| 15 | GTTTGTATGTCTGTTGCTATTAT | Tag-specific Primer |
| 10 | ATTTAATACGACTCACTATAGGGA GAGAAGGCCTTCGGGTTGTAAA-blocking moiety | Promoter Provider |
| 11 | GmCmCmUmUmCmUmUmCmAmUmAm CmAmCmGmCmGm-blocking moiety | Terminating Oligomer m = 2'Ome |
| 16 | KmKmKmKmKmKmKmKmKmKmKmKm KmKmKmKmKmTTTAAAAAAAAA AAAAAAAAAAAAAAAAAAAA | Non-specific Capture Probe. m = 2' Ome K = g or t\u |
| 12 | ¹CmUmGmCmGmGmGmUmAmAmCmG mUmCmAmAmUmGmAmGmCmAmAmA m²CGCAG³ | Detection Probe 1 fluorescein 2 C9 linker 3 DABCYL |
| 13 | See Sequence Listing | Synthetic E. coli rRNA template |

Reagents and Other Protocol Information: Reagents and experimental protocols were essentially as described under Example 4, with the substitution of a non-specific target capture oligonucleotide for the first and second capture oligonucleotides, the substitution of the above-presented E. coli-specific oligonucleotides for HCV-specific oligonucleotides, and the omission of an extender oligonucleotide. Non-specific Target Capture Protocol: Target Capture Reagent (TCR) Preparation. A stock suspension of magnetic beads was mixed at room temperature for 30 minutes. An aliquot of about 150.micro.L of the magnetic bead suspension was added to 5 mL of TCR diluent (15.micro.g beads/reaction when using 50.micro.L/sample), and then slowly mixed at room temperature for 30 minutes. Next, the non-specific capture oligonucleotide was added to 5 mL of the TCR mixture to yield a final concentration of 0.12 pmol/.micro.L. The prepared TCR was mixed gently at room temperature until needed. Sample Preparation. Amplification solution was prepared using primerless amplification reagent, promoter oligonucleotide and tag-specific priming oligonucleotide. The prepared amplification solution was mixed by vortexing and then maintained at 2-8.deg.C. until needed. Enzyme reagent containing the molecular torch detection probe was next prepared and maintained at 2-8.deg.C. until needed. Dilutions of the template rRNA were prepared in 0.2% LLS (lithium lauryl sulfate). Aliquots (50.micro.L) of the magnetic bead target capture solution were transferred into the wells of a microtiter plate for a KINGFISHER 96 (Thermo Fisher Scientific, Inc.; Waltham, Mass.) magnetic particle processor. Samples of diluted template, tagged priming oligonucleotide and terminating oligonucleotide were then added to 1.5 mL of 50% transport medium diluted with water. The target-containing sample mixture was vortexed, and 150.micro.L aliquots transferred into the microtiter plate (Plate 1) wells containing 50.micro.L target capture solution (each well contained 0, 10.sup.3 or 10.sup.5 copies of the E. coli transcript and the appropriate amount of tagged priming oligonucleotide and terminating oligonucleotide). Target Capture Protocol. First there was prepared a microtiter plate containing 200.micro.L of wash reagent (Plate 2). Another microtiter plate (Plate 3) for conducting amplification reactions was prepared, with each well to be used for a reaction containing 30.micro.L of amplification reagent. All three plates (Plates 1-3) were loaded into the magnetic particle processor unit. Magnetic beads harboring nucleic acid complexes were isolated from Plate 1, washed in Plate 2, and then transferred into Plate 3 using standard procedures familiar to those having an ordinary level of skill in the art. Plate 3 was removed from the magnetic particle processor unit, covered with an adhesive tape seal, and then placed into the temperature-controlled real-time instrument.

Real-Time Amplification Protocol. Plate 3 was incubated at 42.deg.C. for 5 minutes in the real-time instrument. The microtiter plate was removed from the real-time instrument and placed onto a 42.deg.C. thermomixer. Each reaction well received a 10.micro.L aliquot of enzyme reagent containing detection probe, and was then covered with an adhesive tape seal. The plate was shaken gently for 60 seconds on the thermomixer, and then placed back into the real-time instrument at 42.deg.C. where real time assay monitoring was commenced. TTime values, which served as indicators of the amount of amplicon synthesized, were determined from the monitored fluorescence signals.

Results and Conclusion.

Figure 21:
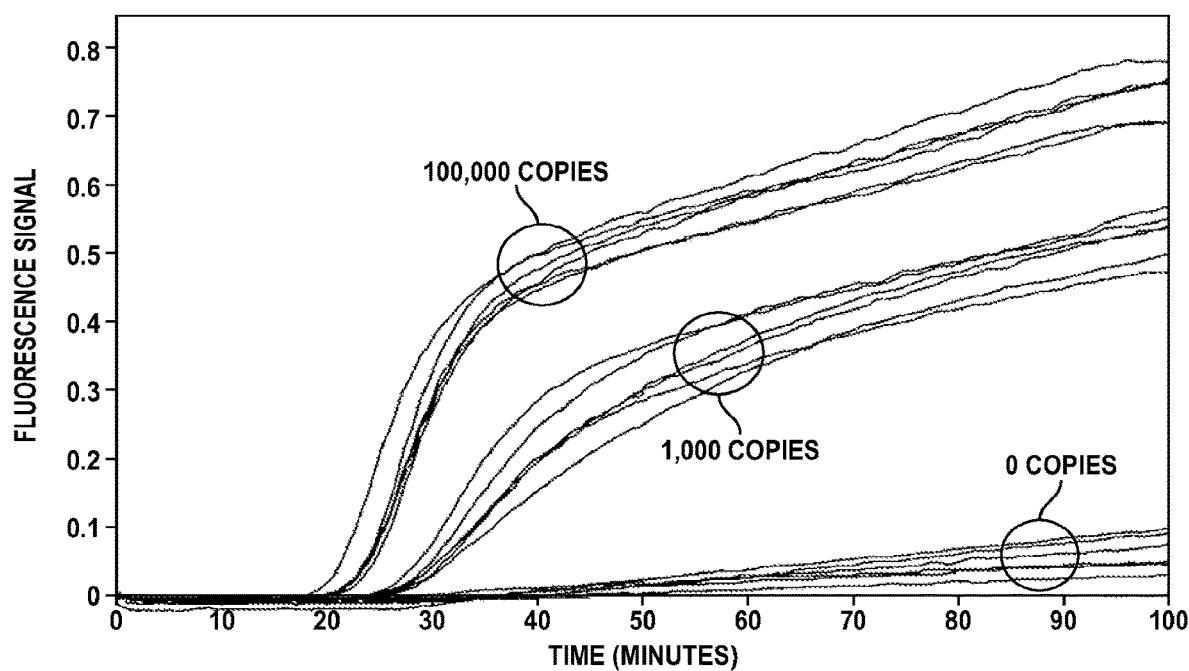

FIG. 21 graphically illustrates the benefits of the disclosed approach to nucleic acid amplification. Procedures that employed a tagged priming oligonucleotide complementary to a target of interest, a target capture step, and a tag-specific priming oligonucleotide that was not complementary to the target of interest (i.e., the E. coli rRNA) yielded dramatically reduced background amplification levels, and so easily permitted discrimination between 0 and 1×10.sup.3 copies of the bacterial template nucleic acid. More specifically, the average TTime values determined for reactions carried out using 1×10.sup.5 copies, 1×10.sup.3 copies, and 0 copies of the E. coli template were 24.7 minutes, 30.6 minutes and 37.5 minutes, respectively. Taken together with the results presented above, these findings were consistent with the presence of bacteria-derived nucleic acids in common reagents used for conducting in vitro nucleic acid amplification reactions. Despite this fact, the procedure employing a tagged priming oligonucleotide was useful for detecting E. coli nucleic acids contained in a test sample without interference from exogenous template nucleic acids contributed by the amplification reagents. For example, a qualitative assay for detecting E. coli nucleic acids at a level of 10.sup.3 copies or greater in a test sample could depend on achieving a threshold fluorescence signal, or TTime value after a predetermined reaction time (e.g., 35 minutes).

The following Example presents comparative results showing how two different detection probes influenced the profiles of real-time amplification run curves. The results further showed how the tagged priming oligonucleotide approach could be used for discriminating 0 and 10.sup.3 copies of the synthetic *E. coli* template nucleic acid—a level approximating the number of copies of 16S rRNA present in a single bacterium.

Example 6 describes detection of *E. coli* rRNA templates in real-time amplification reactions using three different detection probes.

Example 6

Alternative Torch Designs can Improve Assay Results

Amplification reactions were conducted and monitored in a real-time format using one of three different detection probes. The synthetic template nucleic acid, non-specific capture oligonucleotide, tagged priming oligonucleotide, termination oligonucleotide, promoter oligonucleotide and tag-specific priming oligonucleotide used for performing the reactions were identical to those used in the second procedure of the preceding Example. SEQ ID NO:14 is an exemplary tagged primer oligomer comprising a target hybridizing region and a tag region. The target hybridizing region hybridizes to nucleobases 497 to 524 of the synthetic *E. coli* fragment of SEQ ID NO:13. This target hybridizing region is also illustrated in SEQ ID NO:19. SEQ ID NO:10 is a promoter-based oligomer comprising a promoter region and a target hybridizing region. For the instant example, the 3'-end of this oligomer is blocked, thus SEQ ID NO:10 is a promoter provider oligomer. The target hybridizing region for SEQ ID NO:10 hybridizes with nucleobases 413 to 433 of the synthetic *E. coli* fragment of SEQ ID NO:13. This target hybridizing region is also illustrated in SEQ ID NO:20. Four replicates were run for each condition. As before, detection probe was added with the enzyme reagent. Reagents and protocols for non-specific target capture, sample preparation, and real-time amplification also were essentially as described in the second procedure of the preceding Example. Notably, reactions were conducted using 0, 1×10$^3$ or 1×10$^5$ copies of the synthetic *E. coli* template. As above, 2'-O-methyl ribose (2'-O-Me) modifications of the polynucleotide backbone in the sequences presented below are indicated by lower case "m." Blocking moieties at the 3' termini of the promoter oligonucleotide and terminating oligonucleotide comprised a 3'-to-3' linkage that was prepared using 3'-dimethyltrityl-N-benzoyl-2'-deoxycytidine, 5'-succinoyl-long chain alkylamino-CPG (Glen Research Corporation, Sterling, Va.; Cat. No. 20-0102-01). Oligonucleotides, reagents and essential methods used in the procedure were as follows.

TABLE 11

Oligonucleotides

| SEQ ID NO: | Sequence 5' → 3' | Comment |
|---|---|---|
| 14 | GTTTGTATGTCTGTTGCTATTAT GTCTACCTGCTGGCACGGAGTTA GCCGGTGCTTC | |
| 15 | GTTTGTATGTCTGTTGCTATTAT | |
| 10 | ATTTAATACGACTCACTATAGGG AGAGAAGGCCTTCGGGTTGTAAA G-block | |
| 11 | GmCmCmUmUmCmUmCmAmUmA mCmAmCmGmCmGm-block | m = 2'-Ome |
| 16 | KmKmKmKmKmKmKmKmKmKmK mKmKmKmKmKmTTTAAAAAAA AAAAAAAAAAAAAAAAAAAAAAA | m = 2'Ome K = g or t/u |
| 17 | $^1$CmGmAmGmCmAmAmAmGmGmUm AmUmUmAmAmCm$^2$GmCmUmCmGm$^3$ | m = 2'-Ome 1 = fluorescein 2 = C9 linker 3 = DABCYL |
| 18 | $^1$CmGmAmGmCmAmAmAmGmGmUm AmUmUmAmAmCmUmUmAmCm UmCm$^2$GmCmUmCmGm$^3$ | m = 2'-Ome 1 = fluorescein 2 = C9 linker 3 = DABCYL |
| 13 | See sequence listing | Synthetic *E. coli* fragment |

Reagents and Other Protocol Information: Reagents and experimental protocols were essentially as described under Example 5, with a slight change to the conditions used for target capture. Non-Specific Target Capture Protocol: Target Capture Reagent (TCR) Preparation. A stock suspension of magnetic beads was mixed at room temperature for 25 minutes. A 150.micro.L aliquot of the magnetic bead suspension was added to 5 mL of TCR diluent (15.micro.g beads/reaction when using 50.micro.L/sample), and then slowly mixed at room temperature for 25 minutes. Next, the non-specific capture oligonucleotide was added to 5 mL of the TCR mixture to yield a final concentration of 0.12 pmol/.micro.L. The prepared TCR was mixed gently at room temperature until needed. Sample Preparation. Amplification solutions were prepared using primerless AMP Reagent, promoter oligonucleotide and tag-specific priming oligonucleotide. The prepared amplification solutions were mixed by vortexing and then maintained at 2-8.deg.C. until needed. Enzyme Reagents containing the molecular torch detection probes were next prepared and maintained at 2-8.deg.C. until needed. Dilutions of the template rRNA were prepared in 0.2% LLS, as described above. Aliquots (50.micro.L) of the magnetic bead target capture solution were transferred into the wells of a microtiter plate for a KINGFISHER 96 (Thermo Fisher Scientific, Inc.; Waltham, Mass.) magnetic particle processor. Samples of diluted template, tagged priming oligonucleotide and terminating oligonucleotide were then added to 1.5 mL of 50% Transport Medium diluted with water. The target-containing sample mixture was vortexed, and 150.micro.L aliquots transferred into the microtiter plate (Plate 1) wells containing 50.micro.L target capture solution (each well contained 0, 1×10.sup.3 or 1×10.sup.5 copies of the *E. coli* transcript and the appropriate amount of tagged priming oligonucleotide and terminating oligonucleotide).

Target Capture Protocol. The microtiter plate (Plate 1) was incubated at 60.deg.C. for 15 minutes using a SOLO HT incubator (Thermo Labsystems; Franklin, Mass.). The microtiter plate was then placed on the bench at room temperature and allowed to equilibrate for 5 minutes (Plate 1). Next, there was prepared a second microtiter plate containing 200.micro.L of Wash Reagent (Plate 2). A third microtiter plate (Plate 3) for conducting amplification reactions was prepared, with each well to be used for a reaction containing 30.micro.L of amplification reagent. All three plates were loaded into the magnetic particle processor unit. Magnetic beads harboring nucleic acid complexes were isolated from Plate 1, washed in Plate 2, and then transferred into Plate 3 using standard procedures familiar to those having an ordinary level of skill in the art. Plate 3 was removed from the magnetic particle processor unit, covered with an adhesive tape seal, and then placed into the temperature-controlled real-time instrument.

Real-Time Amplification Protocol. Plate 3 was incubated in the real-time instrument at 42.deg.C. for 5 minutes. The microtiter plate was removed from the real-time instrument and placed onto the 42.deg.C. thermomixer. Each reaction well received a 10.micro.L aliquot of Enzyme Reagent containing detection probe, and was then covered with an adhesive tape seal. The plate was shaken gently for 60 seconds on the thermomixer, and then placed back into the real-time instrument at 42.deg.C. where real-time assay monitoring was commenced. TTime values, which served as indicators of the amount of amplicon synthesized, were determined from the monitored fluorescence signals.

Results and Conclusion: The results presented in Table 12 summarize the average TTime values (column 3), and the standard deviations of the average TTime values (column 4) for reactions conducted using the different detection probes. The tabular summary confirmed that all of the tested detection probes yielded very good results in the real-time assays. Each probe advantageously gave a very low signal at the 0 copy level of input target. More specifically, amplicon detected in reactions carried out using 0 copies of input synthetic template was essentially undetectable when the reactions included the detection probes of SEQ ID NO:17 and SEQ ID NO:18. These detection probes have target hybridizing regions configured to respectively hybridize to residues 462 to 477 and residues 455 to 477 of SEQ ID NO:13. Reactions that included one of the detection probes identified by SEQ ID NO:17 and SEQ ID NO:18 gave outstanding results that easily permitted detection of template nucleic acids corresponding roughly to the amount contained in a single bacterium.

TABLE 12

Use of Alternative Detection Probes for Improved Assay Discrimination

| Template Amount | Detection Probe | AvgTTime (min) | SDTTime (min) |
|---|---|---|---|
| 0 copies | SEQ ID NO: 17 | N/A | N/A |
| 10.sup.3 copies | | 38.2 | 2.81 |
| 10.sup.5 copies | | 26.4 | 0.32 |
| 0 copies | SEQ ID NO: 18 | N/A | N/A |
| 10.sup.3 copies | | 35.9 | 2.33 |
| 10.sup.5 copies | | 28.8 | 0.45 |

Taken in view of the results presented Examples 5 and 6, each of SEQ ID NOS:12, and 17-18 represent preferred molecular torches for detecting E. coli using the methods described herein. Highly preferred probes useful for detecting E. coli nucleic acids will have target-complementary sequences corresponding to nucleotide positions 2-24 contained within the probe of SEQ ID NO:12 (i.e., a target hybridizing sequence substantially corresponding to SEQ ID NO:21), or nucleotide positions 2-17 contained within the probe of SEQ ID NO:17 (i.e., a target hybridizing sequence substantially corresponding to SEQ ID NO:22), or nucleotide positions 2-24 contained within the probe of SEQ ID NO:18 (i.e., a target hybridizing sequence substantially corresponding to SEQ ID NO:23). Generally speaking, probes useful for detecting E. coli nucleic acids will have target hybridizing sequences of at least 16 contiguous nucleotides contained within the sequence of TGCGGG-TAACGTCAATGAGCAAAGGTATTAACTTTACTC (SEQ ID NO:24). Overall preferred lengths of desirable probes will be up to 39 nucleotides, more preferably up to 29 nucleotides, more preferably up to 23 nucleotides, or still more preferably up to 16 nucleotides. Of course, useful probes may include RNA and DNA equivalent bases, and include the complements of the foregoing described probes.

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

We claim:

1. A preannealing reaction mixture consisting essentially of a target nucleic acid, an inactivatable target capture oligomer comprising at least a binding pair member, a target hybridizing region comprising a nucleotide sequence of 15 to 30 nucleobases in length complementary to the target nucleic acid and a tag-closing region comprising a nucleotide sequence of 3 to 20 nucleobases in length, wherein said binding pair member, said target hybridizing region and said tag-closing region are joined as a single molecule with said target hybridizing region joined at its 3' end to the 5' end of the tag-closing region and the tag-closing region is joined at its 3' end to the binding pair member, wherein said binding pair member comprises a homopolymeric region that allows capture of the target capture oligomer by hybridizing to a complementary sequence of the other member of the binding pair linked to a support, and wherein at least 80% of nucleotides of said tag-closing region nucleotide sequence are complementary to corresponding nucleotides of a sequence contained within said target hybridizing region.

2. The reaction mixture of claim 1, wherein said tag-closing region comprises a nucleotide sequence that contains one or more nucleotide residues selected from the group consisting of: an abasic nucleotide residue, a wobble nucleotide residue, a mismatched nucleotide residue relative to said residue's corresponding position in said sequence contained within said target hybridizing region, and combinations thereof.

3. The reaction mixture of claim 1, wherein said tag-closing region comprises a nucleotide sequence of at least 6 to 14 nucleobases in length.

4. The reaction mixture of claim 1, wherein said tag-closing region comprises a nucleotide sequence of at least 6 to 9 nucleobases in length.

5. The reaction mixture of claim 1, wherein said tag-closing region comprises a nucleotide sequence of 7 nucleobases in length.

6. The reaction mixture of claim 1, wherein said tag-closing region comprises a nucleotide sequence of at least 6 to 9 nucleobases in length and said target hybridizing regions comprises a nucleotide sequence of 17 nucleobases in length.

7. The reaction mixture of claim 1, wherein said target hybridizing region is joined to said end of said tag-closing region using a nucleotide linker thereby forming a contiguous nucleotide sequence consisting essentially of said target hybridizing region and said tag-closing region.

8. The reaction mixture of claim 7, wherein said binding pair member is joined to said end of said tag-closing region using a nucleotide linker thereby forming a contiguous nucleotide sequence consisting essentially of said binding pair member, said tag-closing region and said target hybridizing region.

9. The reaction mixture of claim 1, further comprising at least one amplification oligomer.

10. The reaction mixture of claim 9, wherein said at least one amplification oligomer is a heterologous amplification oligomer.

11. The reaction mixture of claim 1, under conditions biasing said target hybridizing region towards hybridizing with the target nucleic acid and not towards hybridizing with said tag-closing region.

12. The reaction mixture of claim 1, under conditions biasing said target hybridizing region towards hybridizing with said tag-closing region and not towards hybridizing with a non-target nucleic acid.

13. The reaction mixture of claim 1, wherein the target capture oligomer lacks a detectable label.

14. The reaction mixture of claim 9 further comprising a terminating oligonucleotide to terminate extension from the amplification oligomer.

\* \* \* \* \*

SEQUENCE LISTING

<160> NUMBER OF SEQ ID NOS: 39

<210> SEQ ID NO 1
<211> LENGTH: 60
<212> TYPE: DNA
<213> ORGANISM: Artificial Sequence
<220> FEATURE:
<223> OTHER INFORMATION: Synthetic Oligomer

<400> SEQUENCE: 1
gtttgtatgt ctgttgctat tatgtctaca ggcattgagc gggttgatcc aagaaaggac    60

<210> SEQ ID NO 2
<211> LENGTH: 23
<212> TYPE: DNA
<213> ORGANISM: Artificial Sequence
<220> FEATURE:

<223> OTHER INFORMATION: Synthetic Oligomer

<400> SEQUENCE: 2
gtttgtatgt ctgttgctat tat                                   23

<210> SEQ ID NO 3
<211> LENGTH: 60
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(26)

<400> SEQUENCE: 3
atttaatacg actcactata gggagaccac aacggtttct agccatggcg ttagtatgag    60

<210> SEQ ID NO 4
<211> LENGTH: 26
<212> TYPE: RNA
<213> ORGANISM: Artificial Sequence
<220> FEATURE:
<223> OTHER INFORMATION: Synthetic Oligomer

<400> SEQUENCE: 4
auggcuagac gcuuucugcg ugaaga                                26

<210> SEQ ID NO 5
<211> LENGTH: 42
<212> TYPE: DNA
<213> ORGANISM: Artificial Sequence
<220> FEATURE:
<223> OTHER INFORMATION: Synthetic Oligomer

<400> SEQUENCE: 5
tgtcgtgcag cctccaggac cccccctccc gggagagcca ta              42

<210> SEQ ID NO 6
<211> LENGTH: 52
<212> TYPE: DNA
<213> ORGANISM: Artificial Sequence
<220> FEATURE:
<223> OTHER INFORMATION: Synthetic Oligomer

<400> SEQUENCE: 6
gggcacucgc aagcacccut ttaaaaaaaa aaaaaaaaaa aaaaaaaaaa aa    52

<210> SEQ ID NO 7
<211> LENGTH: 51
<212> TYPE: DNA
<213> ORGANISM: Artificial Sequence
<220> FEATURE:
<223> OTHER INFORMATION: Synthetic Oligomer

<400> SEQUENCE: 7
cauggugcac ggucuacgtt taaaaaaaaa aaaaaaaaa aaaaaaaaaa a      51

<210> SEQ ID NO 8
<211> LENGTH: 23
<212> TYPE: RNA
<213> ORGANISM: Artificial Sequence
<220> FEATURE:
<223> OTHER INFORMATION: Synthetic Oligomer

<400> SEQUENCE: 8
cguuccgcag accacuauga acg                                          23

<210> SEQ ID NO 9
<211> LENGTH: 28
<212> TYPE: DNA
<213> ORGANISM: Artificial Sequence
<220> FEATURE:
<223> OTHER INFORMATION: Synthetic Oligomer

<400> SEQUENCE: 9
cugcuggcac ggaguuagcc ggugcuuc                                     28

<210> SEQ ID NO 10
<211> LENGTH: 47
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(26)

<400> SEQUENCE: 10
atttaatacg actcactata gggagagaag gccttcgggt tgtaaag                47

<210> SEQ ID NO 11
<211> LENGTH: 18
<212> TYPE: RNA
<213> ORGANISM: Artificial Sequence
<220> FEATURE:
<223> OTHER INFORMATION: Synthetic Oligomer

<400> SEQUENCE: 11
gccuucuuca uacacgcg                                                18

<210> SEQ ID NO 12
<211> LENGTH: 29
<212> TYPE: RNA
<213> ORGANISM: Artificial Sequence
<220> FEATURE:
<223> OTHER INFORMATION: Synthetic Oligomer

<400> SEQUENCE: 12
cugcggguaa cgucaaugag caaacgcag                                    29

<210> SEQ ID NO 13
<211> LENGTH: 1542
<212> TYPE: DNA
<213> ORGANISM: Artificial Sequence
<220> FEATURE:
<223> OTHER INFORMATION: Synthetic E.coli template

<400> SEQUENCE: 13
aaattgaaga gtttgatcat ggctcagatt gaacgctggc ggcaggccta acacatgcaa    60
gtcgaacggt aacaggaaga agcttgcttc tttgctgacg agtggcggac gggtgagtaa   120
tgtctgggaa actgcctgat ggagggggat aactactgga aacggtagct aataccgcat   180
aacgtcgcaa gaccaaagag ggggaccttc gggcctcttg ccatcggatg tgcccagatg   240
ggattagcta gtaggtgggg taacggctca cctaggcgac gatccctagc tggtctgaga   300
ggatgaccag ccacactgga actgagacac ggtccagact cctacgggag gcagcagtgg   360
ggaatattgc acaatgggcg caagcctgat gcagccatgc cgcgtgtatg aagaaggcct   420
tcgggttgta aagtactttc agcggggagg aagggagtaa agttaatacc tttgctcatt   480

-continued

```
gacgttaccc gcagaagaag caccggctaa ctccgtgcca gcagccgcgg taatacggag    540
ggtgcaagcg ttaatcggaa ttactgggcg taaagcgcac gcaggcggtt tgttaagtca    600
gatgtgaaat ccccgggctc aacctgggaa ctgcatctga tactggcaag cttgagtctc    660 gtagagggg gtagaattcc aggtgtagcg gtgaaatgcg tagagatctg gaggaatacc    720
ggtggcgaag gcggcccct ggacgaagac tgacgctcag gtgcgaaagc gtggggagca    780
aacaggatta gataccctgg tagtccacgc cgtaaacgat gtcgacttgg aggttgtgcc    840
cttgaggcgt ggcttccgga gctaacgcgt taagtcgacc gcctgggag tacggccgca    900 aggttaaaac tcaaatgaat tgacggggc ccgcacaagc ggtggagcat gtggtttaat    960
tcgatgcaac gcgaagaacc ttacctggtc ttgacatcca cggaagtttt cagagatgag   1020
aatgtgcctt cgggaaccgt gagacaggtg ctgcatggct gtcgtcagct cgtgttgtga   1080
aatgttgggt taagtcccgc aacgagcgca acccttatcc tttgttgcca gcggtccggc   1140
cgggaactca aaggagactg ccagtgataa actggaggaa ggtggggatg acgtcaagtc   1200
atcatggccc ttacgaccag ggctacacac gtgctacaat ggcgcataca agagaaagcg   1260
acctcgcgag agcaagcgga cctcataaag tgcgtcgtag tccggattgg agtctgcaac   1320
tcgactccat gaagtcggaa tcgctagtaa tcgtggatca gaatgccacg gtgaatacgt   1380
tcccgggcct tgtacacacc gcccgtcaca ccatgggagt gggttgcaaa gaagtaggt    1440 agcttaacct tcgggagggc gcttaccact ttgtgattca tgactggggt gaagtcgtaa   1500
caaggtaacc gtaggggaac ctgcggttgg atcacctcct ta                      1542
```

<210> SEQ ID NO 14
<211> LENGTH: 57
<212> TYPE: DNA
<213> ORGANISM: Artificial Sequence
<220> FEATURE:
<223> OTHER INFORMATION: Synthetic Oligomer

<400> SEQUENCE: 14

```
gtttgtatgt ctgttgctat tatgtctacc tgctggcacg gagttagccg gtgcttc       57
```

<210> SEQ ID NO 15
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 15

```
gtttgtatgt ctgttgctat tat                                            23
```

<210> SEQ ID NO 16
<211> LENGTH: 51
<212> TYPE: DNA
<213> ORGANISM: Artificial Sequence
<220> FEATURE:
<223> OTHER INFORMATION: Synthetic Oligomer

<400> SEQUENCE: 16

```
kkkkkkkkkk kkkkkkkktt taaaaaaaaa aaaaaaaaa aaaaaaaaaa a              51
```

<210> SEQ ID NO 17
<211> LENGTH: 22
<212> TYPE: RNA
<213> ORGANISM: Artificial Sequence
<220> FEATURE:
<223> OTHER INFORMATION: Synthetic Oligomer -continued

```
<400> SEQUENCE: 17
cgagcaaagg uauuaacgcu cg                                        22

<210> SEQ ID NO 18
<211> LENGTH: 29
<212> TYPE: RNA
<213> ORGANISM: Artificial Sequence
<220> FEATURE:
<223> OTHER INFORMATION: Synthetic Oligomer

<400> SEQUENCE: 18
cgagcaaagg uauuaacuuu acucgcucg                                 29

<210> SEQ ID NO 19
<211> LENGTH: 28
<212> TYPE: DNA
<213> ORGANISM: Artificial Sequence
<220> FEATURE:
<223> OTHER INFORMATION: synthetic oligomer

<400> SEQUENCE: 19
gaagcaccgg ctaactccgt gccagcag                                  28

<210> SEQ ID NO 20
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 20
gaaggccttc gggttgtaaa g                                         21

<210> SEQ ID NO 21
<211> LENGTH: 23
<212> TYPE: RNA
<213> ORGANISM: Artificial Sequence
<220> FEATURE:
<223> OTHER INFORMATION: Synthetic Oligomer

<400> SEQUENCE: 21
ugcggguaac gucaaugagc aaa                                       23

<210> SEQ ID NO 22
<211> LENGTH: 16
<212> TYPE: RNA
<213> ORGANISM: Artificial Sequence
<220> FEATURE:
<223> OTHER INFORMATION: Synthetic Oligomer

<400> SEQUENCE: 22
gagcaaaggu auuaac                                               16

<210> SEQ ID NO 23
<211> LENGTH: 23
<212> TYPE: RNA
<213> ORGANISM: Artificial Sequence
<220> FEATURE:
<223> OTHER INFORMATION: Synthetic Oligomer

<400> SEQUENCE: 23
gagcaaaggu auuaacuuua cuc                                       23

<210> SEQ ID NO 24
```

```
<211> LENGTH: 39
<212> TYPE: DNA
<213> ORGANISM: Artificial Sequence
<220> FEATURE:
<223> OTHER INFORMATION: Consensus Sequence of Probe Binding Regions

<400> SEQUENCE: 24
tgcgggtaac gtcaatgagc aaaggtatta actttactc                            39

<210> SEQ ID NO 25
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 25
gcugauaagc cgcgaguauc agctttaaaa aaaaaaaaa aaaaaaaaaa aaaaaa          56

<210> SEQ ID NO 26
<211> LENGTH: 57
<212> TYPE: DNA
<213> ORGANISM: Artificial Sequence
<220> FEATURE:
<223> OTHER INFORMATION: Synthetic Oligomer

<400> SEQUENCE: 26
gcugauaagc cgcgaguuau cagctttaaa aaaaaaaaa aaaaaaaaaa aaaaaaa         57

<210> SEQ ID NO 27
<211> LENGTH: 58
<212> TYPE: DNA
<213> ORGANISM: Artificial Sequence
<220> FEATURE:
<223> OTHER INFORMATION: Synthetic Oligomer

<400> SEQUENCE: 27
gcugauaagc cgcgaguuua ucagctttaa aaaaaaaaa aaaaaaaaaa aaaaaaaa        58

<210> SEQ ID NO 28
<211> LENGTH: 59
<212> TYPE: DNA
<213> ORGANISM: Artificial Sequence
<220> FEATURE:
<223> OTHER INFORMATION: Synthetic Oligomer

<400> SEQUENCE: 28
gcugauaagc cgcgagucuu aucagcttta aaaaaaaaa aaaaaaaaaa aaaaaaaaa       59

<210> SEQ ID NO 29
<211> LENGTH: 60
<212> TYPE: DNA
<213> ORGANISM: Artificial Sequence
<220> FEATURE:
<223> OTHER INFORMATION: Synthetic Oligomer

<400> SEQUENCE: 29
gcugauaagc cgcgagugcu uaucagcttt aaaaaaaaa aaaaaaaaaa aaaaaaaaaa      60

<210> SEQ ID NO 30
<211> LENGTH: 62
<212> TYPE: DNA
<213> ORGANISM: Artificial Sequence
<220> FEATURE:
<223> OTHER INFORMATION: Synthetic Oligomer

<400> SEQUENCE: 30
```

```
gcugauaagc cgcgagucgg cuuaucagct uuaaaaaaaa aaaaaaaaaa aaaaaaaaaa    60
aa                                                                 62

<210> SEQ ID NO 31
<211> LENGTH: 64
<212> TYPE: DNA
<213> ORGANISM: Artificial Sequence
<220> FEATURE:
<223> OTHER INFORMATION: Synthetic Oligomer

<400> SEQUENCE: 31
gcugauaagc cgcgagucgc ggcuuaucag cuuuaaaaaa aaaaaaaaaa aaaaaaaaaa    60
aaaa                                                               64

<210> SEQ ID NO 32
<211> LENGTH: 50
<212> TYPE: DNA
<213> ORGANISM: Artificial Sequence
<220> FEATURE:
<223> OTHER INFORMATION: Synthetic Oligomer

<400> SEQUENCE: 32
gcugauaagc cgcgaguuuu aaaaaaaaaa aaaaaaaaaa aaaaaaaaaa              50

<210> SEQ ID NO 33
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 33
aatttaatac gactcactat agggagacga acgctggcgg cgtgcttaac acatgc       56

<210> SEQ ID NO 34
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 34
gtgacccaat gatctaaca                                               19

<210> SEQ ID NO 35
<211> LENGTH: 23
<212> TYPE: RNA
<213> ORGANISM: Artificial Sequence
<220> FEATURE:
<223> OTHER INFORMATION: Synthetic Oligomer

<400> SEQUENCE: 35
ccagggccuu uccguucgcc ugg                                          23

<210> SEQ ID NO 36
<211> LENGTH: 55
<212> TYPE: DNA
<213> ORGANISM: Artificial Sequence
<220> FEATURE:
<223> OTHER INFORMATION: Synthetic Oligomer

<400> SEQUENCE: 36
ctgcttttgt gggggtgacc caatgatcta acactcgagc accccacaaa agcag        55
```

<210> SEQ ID NO 37
<211> LENGTH: 17
<212> TYPE: RNA
<213> ORGANISM: Artificial Sequence
<220> FEATURE:
<223> OTHER INFORMATION: Synthetic Oligomer

<400> SEQUENCE: 37
agcguucguc cugagcc                                                  17

<210> SEQ ID NO 38
<211> LENGTH: 1486
<212> TYPE: DNA
<213> ORGANISM: Propionibacterium acnes
<300> PUBLICATION INFORMATION:
<308> DATABASE ACCESSION NUMBER: AB042288.1 gi:7707831
<309> DATABASE ENTRY DATE: 2000-05-05
<313> RELEVANT RESIDUES IN SEQ ID NO: (1)..(1486)

<400> SEQUENCE: 38
agagtttgat cctggctcag gacgaacgct ggcggcgtgc ttaacacatg caagtcgaac      60
ggaaaggccc tgcttttgtg gggtgctcga gtggcgaacg ggtgagtaac acgtgagtaa     120
cctgcccttg actttgggat aacttcagga aactgggggc aataccggat aggagctcct    180
gctgcatggt gggggttgga aagtttcggc ggttggggat ggactcgcgg cttatcagct    240
tgttggtggg gtagtggctt accaaggctt tgacgggtag ccggcctgag agggtgaccg    300
gccacattgg gactgagata cggcccagac tcctacggga ggcagcagtg gggaatattg    360
cacaatgggc ggaagcctga tgcagcaacg ccgcgtgcgg gatgacggcc ttcgggttgt    420
aaaccgcttt cgcctgtgac gaagcgtgag tgacggtaat gggtaaagaa gcaccggcta    480
actacgtgcc agcagccgcg gtgatacgta gggtgcgagc gttgtccgga tttattgggc    540
gtaaagggct cgtaggtggt tgatcgcgtc ggaagtgtaa tcttgggggct taaccctgag    600 cgtgctttcg atacggggttg acttgaggaa ggtaggggga aatggaattc ctggtggagc    660
ggtggaatgc gcagatatca ggaggaacac cagtggcgaa ggcggttctc tgggcctttc    720
ctgacgctga ggagcgaaag cgtggggagc gaacaggctt agataccctg gtagtccacg    780
ctgtaaacgg tgggtactag gtgtggggtc cattccacgg gttccgtgcc gtagctaacg    840
ctttaagtac cccgcctggg gagtacggcc gcaaggctaa aactcaaagg aattgacggg    900
gccccgcaca agcggcggag catgcggatt aattcgatgc aacgcgtaga accttacctg    960
ggtttgacat ggatcgggag tgctcagaga tgggtgtgcc tcttttgggg tcggttcaca   1020
ggtggtgcat ggctgtcgtc agctcgtgtc gtgagatgtt gggttaagtc ccgcaacgag   1080 cgcaacccctt gttcactgtt gccagcacgt tatggtgggg actcagtgga gaccgccggg   1140
gtcaactcgg aggaaggtgg ggatgacgtc aagtcatcat gccccttatg tccagggctt   1200
cacgcatgct acaatggctg gtacagagag tggcagcct gtgagggtga gcgaatctcg   1260
gaaagccggt ctcagttcgg attggggtct gcaactcgac ctcatgaagt cggagtcgct   1320
agtaatcgca gatcagcaac gctgcggtga atacgttccc ggggcttgta cacaccgccc   1380
gtcaagtcat gaaagttggt aacacccgaa gccgtggcc taaccgttgt gggggagccg   1440
tcgaaggtgg gactggtgat taggactaag tcgtaacaag gtaacc                  1486

<210> SEQ ID NO 39
<211> LENGTH: 38
<212> TYPE: DNA
<213> ORGANISM: Artificial Sequence

```
<220> FEATURE:
<223> OTHER INFORMATION: Synthetic Oligomer

<400> SEQUENCE: 39
gtgacccaat gatctaacag agcaccccac aaaagcag                              38
```